United States Patent
Novak et al.

(10) Patent No.: US 11,807,871 B2
(45) Date of Patent: Nov. 7, 2023

(54) COMPLEX HUMAN GUT MICROBIOME CULTURED IN AN ANAEROBIC HUMAN GUT-ON-A-CHIP

(71) Applicant: President and Fellows of Harvard College, Cambridge, MA (US)

(72) Inventors: Richard Novak, Boston, MA (US); Sasan Jalili-Firoozinezhad, Cambridge, MA (US); Francesca S. Gazzaniga, Jamaica Plain, MA (US); Elizabeth L. Calamari, Ashland, MA (US); Diogo M. Camacho, Framingham, MA (US); Bret A. Nestor, Regina (CA); Cicely Fadel, Brookline, MA (US); Michael L. Cronce, Roxbury, MA (US); Dennis L. Kasper, Boston, MA (US); Donald E. Ingber, Boston, MA (US); Amir Bein, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 578 days.

(21) Appl. No.: 15/733,716

(22) PCT Filed: Apr. 2, 2019

(86) PCT No.: PCT/US2019/025460
§ 371 (c)(1),
(2) Date: Oct. 2, 2020

(87) PCT Pub. No.: WO2019/195344
PCT Pub. Date: Oct. 10, 2019

(65) Prior Publication Data
US 2021/0079356 A1     Mar. 18, 2021

Related U.S. Application Data

(60) Provisional application No. 62/722,658, filed on Aug. 24, 2018, provisional application No. 62/651,438, filed on Apr. 2, 2018.

(51) Int. Cl.
| | |
|---|---|
| *C12N 5/071* | (2010.01) |
| *C12M 3/06* | (2006.01) |
| *C12N 1/20* | (2006.01) |
| *C12M 3/00* | (2006.01) |

(52) U.S. Cl.
CPC ........... *C12N 5/0679* (2013.01); *C12M 21/08* (2013.01); *C12M 23/16* (2013.01); *C12N 1/20* (2013.01)

(58) Field of Classification Search
None
See application file for complete search history.

(56) References Cited

U.S. PATENT DOCUMENTS

| | | |
|---|---|---|
| 2006/0199260 A1 | 9/2006 | Zhang |
| 2017/0306278 A1 | 10/2017 | Nguyen |
| 2017/0349871 A1 | 12/2017 | Ingber |

FOREIGN PATENT DOCUMENTS

| | | |
|---|---|---|
| WO | WO 2011/157984 A1 | 12/2001 |
| WO | WO 2017/131839 A2 | 8/2017 |

OTHER PUBLICATIONS

Bein et al. "Microfluidic Organ-on-a-Chip Models of Human Intestine" (2018) Cellular Molecular Gastroenterology Hepatology, vol. 5; 659-668. (Year: 2018).*
Lee et al. "Human gut-on-a-chip technology: will this revolutionize our understanding of IBD and future treatments?" (2016) Expert Rev Gastroenterology & Hepatology, vol. 10, issue 8: 883-885. (Year: 2016).*
Trujillo-de Santiago et al. "Gut-microbiota-on-a-chip: an enabling field for physiological research" (Oct. 2018) Microphysiol Syst, vol. 2: 1-35. (Year: 2018).*
Combined Search Report and Examination Report for United Kingdom Application No. GB 22182539, dated Feb. 20, 2023 (7 pages).
Von Martels, Julius J .H. et al.; "The role of the gut microbiota in health and disease: In vitro modeling of host-microbe interactions at the aerobe-anaerobe interphase of the human gut"; *Anaerobe* 44, pp. 3-12; Jan. 3, 2017 , retrieved from http://dx.doi.org/10.1016/j.anaerobe.2017.01.001 (10 pages).
Examination Report for United Kingdom Application No. GB 20169801, dated Jan. 27, 2023 (1 page).
International Search Report and Written Opinion of International Searching Authority for Application No. PCT/US2019/025460, dated Jul. 18, 2019 (10 pages).
Kim et al.; "Co-culture of Living Microbiome with Microengineered Human Intestinal Villi in a Gut-on-a-Chip Microfluidic Device"; Journal of Visualized Experiments, Iss. 114; Aug. 30, 2016 (7 pages).
Cho, I. & Blaser, M. J.; "The human microbiome: at the interface of health and disease"; *Nat. Rev. Genet.* 13, 260 (2012) (11 pages).
Donaldson, G. P. et al.; "Gut biogeography of the bacterial microbiota"; *Nat. Rev. Microbial.* 14, 20-32 (2016) (13 pages).
Pickard, J. M. et al.; "Gut microbiota: Role in pathogen colonization, immune responses, and inflammatory disease"; *Immunol. Rev.* 279, 70-89 (2017) (20 pages).

(Continued)

*Primary Examiner* — Teresa E Knight
(74) *Attorney, Agent, or Firm* — NIXON PEABODY LLP

(57) ABSTRACT

A microfluidic device is directed to sustaining a complex microbial community in direct and indirect contact with living human intestinal cells in vitro. The device includes a first microchannel having cultured cells of a human intestinal epithelium and microbiota, the first microchannel further having a first level of oxygen. The device further includes a second microchannel having cultured cells of a vascular endothelium, the second microchannel further having a second level of oxygen. The device also includes a membrane located at an interface region between the first microchannel and the second microchannel, the membrane being composed of an oxygen-permeable material or further having pores via which oxygen flows between the first microchannel and the second microchannel to form a physiologically-relevant oxygen gradient.

11 Claims, 33 Drawing Sheets

(56) References Cited

OTHER PUBLICATIONS

Sommer, F. et al.; "The gut microbiota—masters of host development and physiology"; *Nat. Rev. Microbiol.* 11, 227; Feb. 25, 2013 (12 pages).
Walter, J. et al.; "The human gut microbiome: ecology and recent evolutionary changes"; *Annu. Rev. Microbiol.* 65, 411-429; Jun. 16, 2011 (19 pages).
Sommer, M. O.; "Advancing gut microbiome research using cultivation"; *Curr. Opin. Microbiol.* 27, pp. 127-132 (2015) (6 pages).
Eain, M. M. G. et al.; "Engineering Solutions for Representative Models of the Gastrointestinal Human-Microbe Interface"; *Engineering* 3, 60-65 (2017) (6 pages).
Fritz, J. V. et al. "From meta-omics to causality: experimental models for human microbiome research"; *Microbiome* 1, 14 (2013) (15 pages).
Arrieta, M.-C. et al.; "Human Microbiota-Associated Mice: A Model with Challenges"; *Cell Host Microbe* 19, 575-578 (2016) (4 pages).
Nguyen, T. L. A. et al.; "How informative is the mouse for human gut microbiota research?"; *Dis. Model. Mech.* 8, 1-16 (2015) (16 pages).
Sadabad, M. S. et al.; "A simple coculture system shows mutualism between anaerobic faecalibacteria and epithelial Caco-2 cells"; *Sci. Rep.* 5, 17906; Dec. 15, 2015 (9 pages).
Dutta, D. et al.; "Organoid culture systems to study host-patho gen interactions"; *Curr. Opin. Immunol.* 48, 15-22 (2017) (8 pages).
Fatehullah, A. et al.; "Organoids as an in vitro model of human development and disease"; *Nat. Cell Biol.* 18, 246-254 (2016) (9 pages).
Shah, P. et al.; "A microfluidics-based in vitro model of the gastrointestinal human-microbe interface"; *Nat. Commun.* 7, 11535; May 11, 2016 (15 pages).
Kim, H. J. et al.; "Human gut-on-a-chip inhabited by microbial flora that experiences intestinal peristalsis-like motions and flow"; *Lab. Chip* 12, 2165-2174 (2012) (10 pages).
Kim, H. J. et al.; "Contributions of microbiome and mechanical deformation to intestinal bacterial overgrowth and inflammation in a human gut-on-a-chip"; *Proc. Natl. Acad. Sci.* 113, E7-E15 (2016) (9 pages).
Park, G.-S. et al.; "Emulating Host-Microbiome Ecosystem of Human Gastrointestinal Tract in Vitro"; *Stem Cell Rev.* 13, 321-334; May 10, 2017 (14 pages).
Chung, H. et al.; "Gut immune maturation depends on colonization with a host-specific microbiota"; *Cell* 149, 1578-1593 (2012) (16 pages).
Surana, N. K. et al.; "Moving beyond microbiome-wide associations to causal microbe identification"; *Nature* 552, 244-247 (2017) (15 pages).
Jalili-Firoozinezhad, S. et al.; "Modeling radiation injury-induced cell death and countermeasure drug responses in a human Gut-on-a-Chip"; *Cell Death Dis.* 9, 223 (2018) (14 pages).
Zheng, L. et al.; "Physiologic hypoxia and oxygen homeostasis in the healthy intestine. A Review in the Theme: Cellular Responses to Hypoxia"; *Am. J. Physiol. Cell Physiol.* 309, C350-C360 (2015) (11 pages).
Jiang, B. H. et al.; "Hypoxia-inducible factor 1 levels vary exponentially over a physiologically relevant range of O2 tension"; *Am. J. Physiol.* 271, C1172-1180 (1996) (9 pages).
Surana, N. K. et al.; "The yin yang of bacterial polysaccharides: lessons learned from B. fragilis PSA"; *Immunol. Rev.* vol. 245, pp. 13-26 (2012) (14 pages).
Patrick, S. et al.; "The growth and survival of capsulate and non-capsulate Bacteroides fragilis in vivo and in vitro"; *J. Med. Microbiol.* 17, 237-246 (1984) (10 pages).
Hudak, J. E. et al.; "Illuminating vital surface molecules of symbionts in health and disease"; *Nat. Microbiol.* 2, 17099 (2017) (8 pages).
The Human Microbiome Project Consortium et al.; "Structure, function and diversity of the healthy human microbiome"; *Nature* 486, pp. 207-214 (Jun. 4, 2012) (8 pages).
Fujio-Vejar, S. et al.; "The Gut Microbiota of Healthy Chilean Subjects Reveals a High Abundance of the Phylum Verrucomicrobia"; *Front. Microbiol.* 8, 1221 (2017) (11 pages).
Schneeberger, M. et al.; "Akkermansia muciniphila inversely correlates with the onset of inflammation, altered adipose tissue metabolism and metabolic disorders during obesity in mice"; *Sci. Rep.* 5, 16643; Nov. 13, 2015 (14 pages).
Everard, A. et al.; "Cross-talk between Akkermansia muciniphila and intestinal epithelium controls diet-induced obesity"; *Proc. Natl. Acad. Sci.* 110, 9066-9071 (2013) (6 pages).
Sheridan, W. G. et al.; "Intraoperative tissue oximetry in the human gastrointestinal tract"; *Am. J. Surg.* vol. 159, pp. 314-319; Mar. 1990 (6 pages).
He, G. et al.; "Noninvasive measurement of anatomic structure and intraluminal oxygenation in the gastrointestinal tract of living mice with spatial and spectral EPR imaging"; *Proc. Natl. Acad. Sci.* 96, 4586-4591 (1999) (6 pages).
Ohland, C. L. et al.; "Microbial Activities and Intestinal Homeostasis: A Delicate Balance Between Health and Disease"; *Cell. Mol. Gastroenterol. Hepatol.* vol. 1, No. 1, pp. 28-40; Jan. 2015 (13 pages).
Flint, H. J. et al.; "The role of the gut microbiota in nutrition and health"; *Nat. Rev. Gastroenterol. Hepatol.* 9, 577 (2012) (13 pages).
Albenberg, L. et al.; "Correlation Between Intraluminal Oxygen Gradient and Radial Partitioning of Intestinal Microbiota in Humans and Mice"; *Gastroenterology* 147, 1055-1063.e8 (2014) (17 pages).
Bauglm, A. D. et al.; "The strict anaerobe Bacteroides fragilis grows in and benefits from nanomolar concentrations of oxygen", *Nature* 427, 441-444 (2004) (4 pages).
Hsiao, E. Y. et al.; "Microbiota modulate behavioral and physiological abnormalities associated with neurodevelopmental disorders"; *Cell* 155, 1451-1463 (2013) (13 pages).
Clemente, J. C. et al.; "The Impact of the Gut Microbiota on Human Health: An Integrative View"; *Cell* 148, 1258-1270 (2012) (13 pages).
Shin, N.-R.net al.; "Proteobacteria: microbial signature of dysbiosis in gut microbiota"; *Trends Biotechnol.* 33, 496-503 (2015) (8 pages).
Cirstea, M. et al.; "Good Bug, Bad Bug: Breaking through Microbial Stereotypes"; *Cell Host Microbe* 23, 10-13 (2018) (4 pages).
Karhausen, J. et al.; "Epithelial hypoxia-inducible factor-1 is protective in murine experimental colitis"; *J. Clin. Invest.* 114, 1098-1106 (2004) (10 pages).
Manresa, M. C. et al.; "Hypoxia Inducible Factor (HIF) Hydroxylases as Regulators of Intestinal Epithelial Barrier Function"; *Cell. Mol. Gastroenterol. Hepatol.* vol. 3, No. 3, pp. 303-315 (2017) (13 pages).
Pedicord, V. A. et al.; "Exploiting a host-commensal interaction to promote intestinal barrier function and enteric pathogen tolerance"; *Sci. Immunol.* vol. 1; Sep. 22, 2016 (14 pages).
Goodman, A. L. et al.; "Extensive personal human gut microbiota culture collections characterized and manipulated in gnotobiotic mice"; *Proc. Natl. Acad. Sci.* 108, 6252-6257 (2011) (6 pages).
Kasendra, M. et al.; "Development of a primary human Small Intestine-on-a-Chip using biopsy-derived organoids"; *Sci. Rep.* 8, 2871 (2018) (14 pages).
Workman, M. J. et al.; "Enhanced Utilization of Induced Pluripotent Stem Cell-Derived Human Intestinal Organoids Using Microengineered Chips"; *Cell. Mol. Gastroenterol. Hepatol.* vol. 5, No. 4, pp. 669-677 (2017); doi:10.1016/j.jcmgh.2017.12.008 (11 pages).
Hooper, L. V. et al.; "Interactions Between the Microbiota and the Immune System"; *Science* 336, 1268-1273 (2012) (6 pages).
Rimoldi, M. et al. Intestinal immune homeostasis is regulated by the crosstalk between epithelial cells and dendritic cells. *Nat. Immunol.* vol. 6, No. 5, pp. 507-514; May 2005 (9 pages).
Huh, D. et al.; "Microfabrication of human organs-on-chips"; *Nat. Protoc.* vol. 8, No. 11, pp. 2135-2157; Oct. 10, 2013 (23 pages).
Otsu, N.; "A Threshold Selection Method from Gray-Level Histograms"; *IEEE Trans. Syst. Man Cybern.* vol. SMC-9, No. 1, pp. 62-66; Jan. 1979 (5 pages).
McMurdie, P. J. et al.; "phyloseq: An R Package for Reproducible Interactive Analysis and Graphics of Microbiome Census Data"; *PLOS ONE* vol. 8, Issue 4, e61217; Apr. 2013 (11 pages).

(56) References Cited

OTHER PUBLICATIONS

Love, M. I. et al.; "Moderated estimation of fold change and dispersion for RNA-seq data with DESeq2"; *Genome Biol.* 15, 550 (2014) (21 pages).

\* cited by examiner

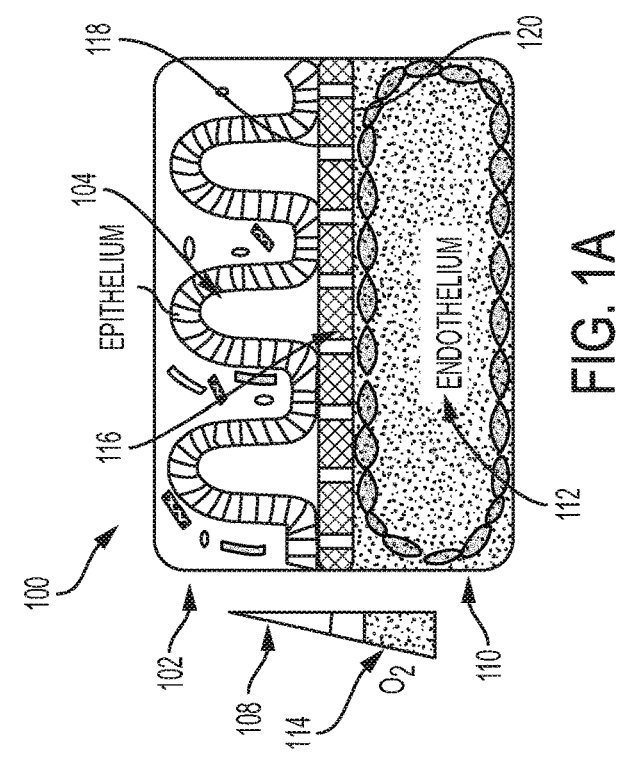
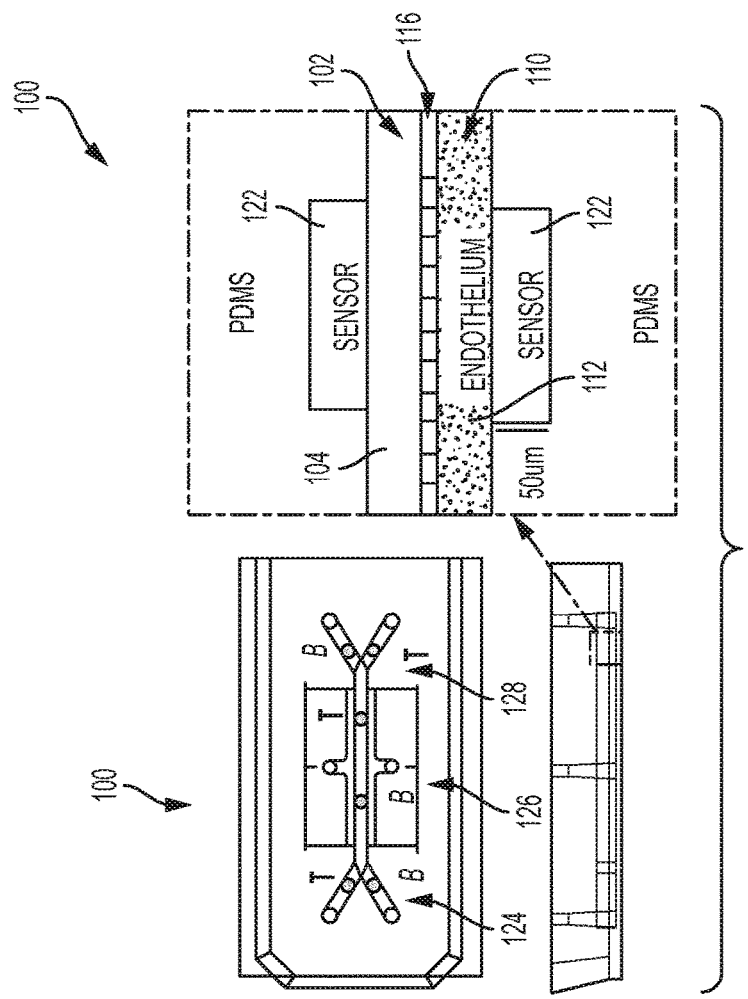
FIG. 1A
FIG. 1B

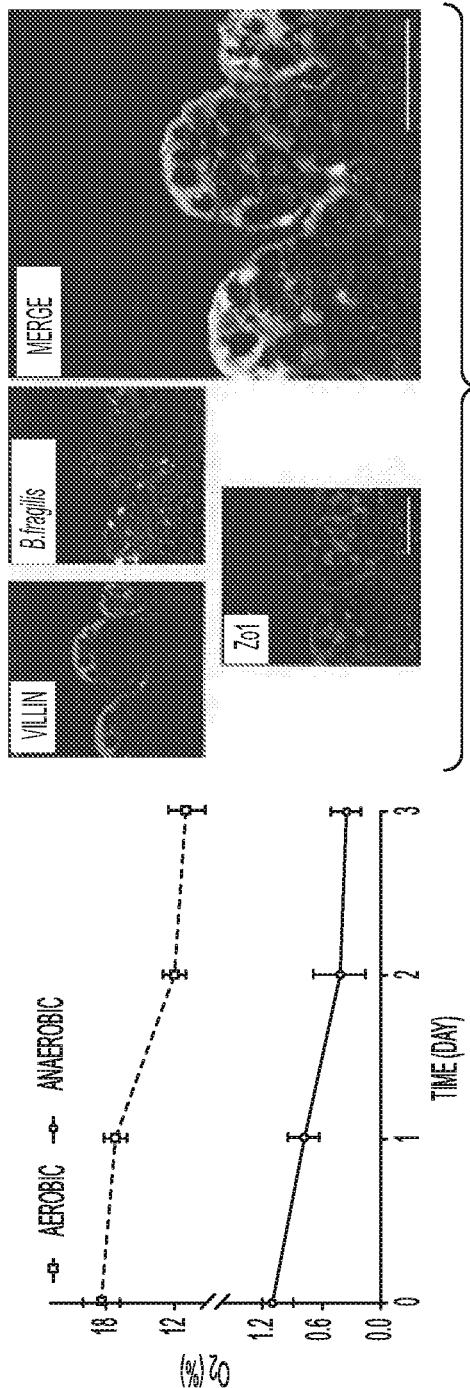
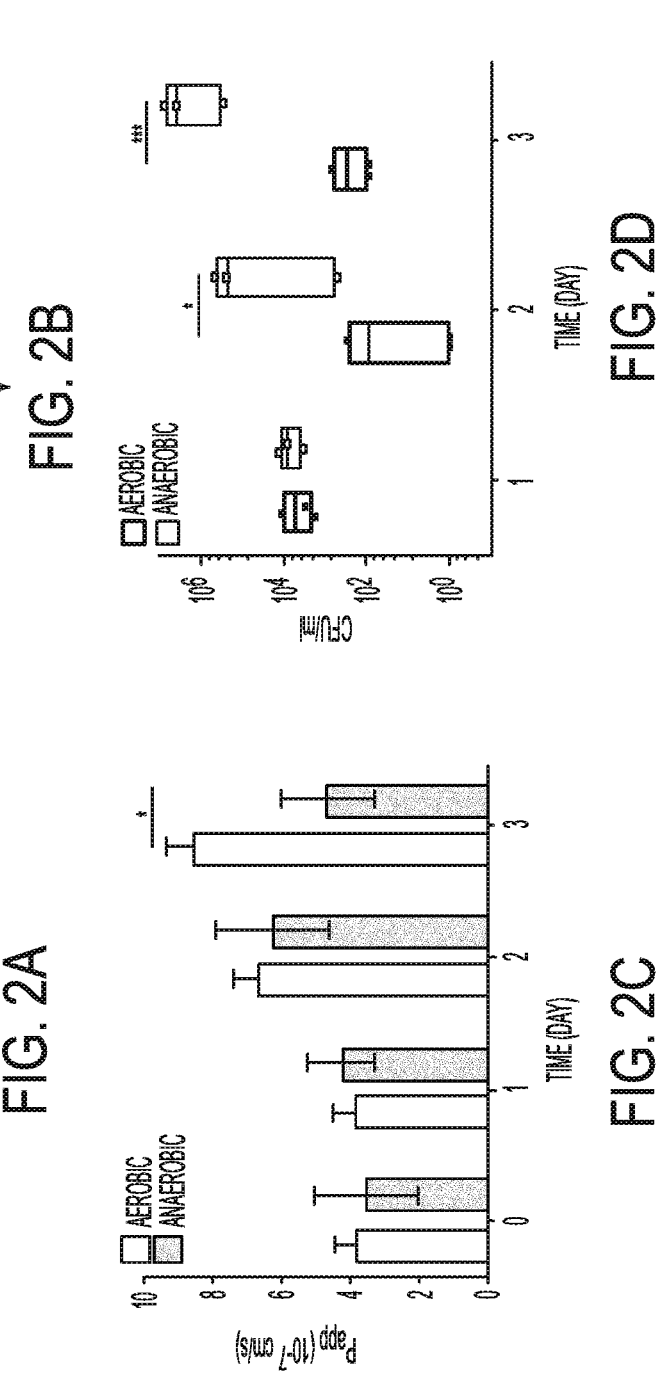
FIG. 2A FIG. 2B FIG. 2C FIG. 2D

| SAMPLE NUMBER (Hmb OR Mmb) | MEDIA TESTED* |
|---|---|
| 1 | STOCK |
| 2 | BRAIN HEART INFUSION |
| 3 | BRUCELLA |
| 4 | $GMM^{40}$ |
| 5 | HEMIN 5 μg/ml |
| 6 | HEMIN 5 μg/ml, VITAMIN K1 0.5 μg/ml |
| 7 | VITAMIN K1 0.5 μg/ml |
| 8 | PORCINE MUCIN 1 mg/ml |
| 9 | PORCINE MUCIN 1 mg/ml, APPLE PECTIN 1 mg/ml |

FIG. 12

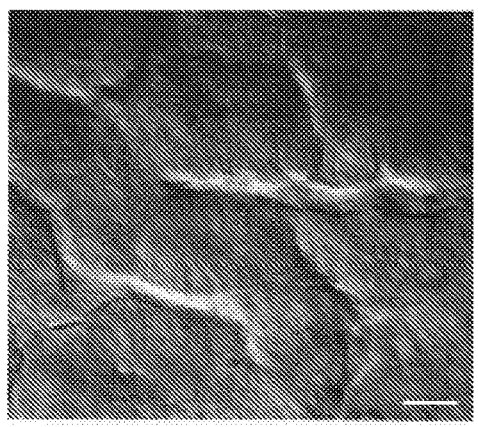
FIG. 16A
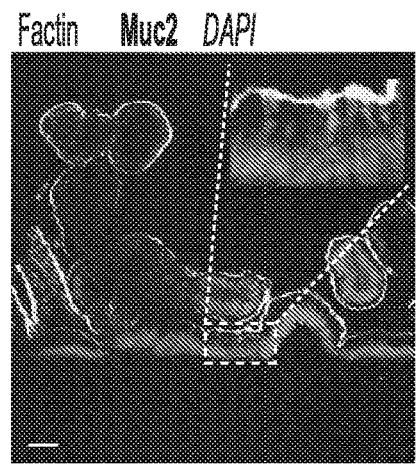
FIG. 16B
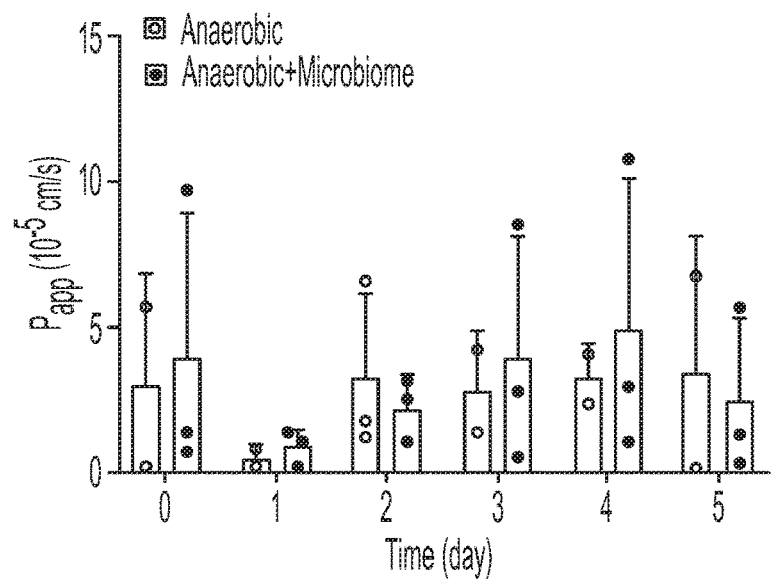
FIG. 16C
| Ileum sample (day 5) | Observed richness | Shannon diversity |
|---|---|---|
| 36 wk infant | 122 | 0.32 |
| 36 wk infant | 118 | 0.34 |
| 36 wk infant | 121 | 0.31 |
| 30 wk infant | 135 | 1.10 |
FIG. 16D Hmm + EHEC Mmm + EHEC

COMPLEX HUMAN GUT MICROBIOME CULTURED IN AN ANAEROBIC HUMAN GUT-ON-A-CHIP

CROSS-REFERENCE TO RELATED APPLICATIONS

This application is a national stage of International Application No. PCT/US2019/025460, filed Apr. 2, 2019, which claims priority to U.S. Provisional Patent Application No. 62/722,658, filed Aug. 24, 2018, and U.S. Provisional Patent Application No. 62/651,438, filed Apr. 2, 2018, each of which is hereby incorporated by reference herein in its entirety.

STATEMENT REGARDING FEDERALLY SPONSORED RESEARCH

This invention was made with government support under W911NF-16-C-0050 awarded by the U.S. Army/ARO and HHSF223201310079C awarded by the U.S. Food & Drug Administration (FDA). The Government has certain rights in this invention.

FIELD OF THE INVENTION

The present invention relates generally to supporting dynamic interactions between living human intestinal epithelium and a directly opposed complex community of living human aerobic and anaerobic commensal gut microbes with a population diversity similar to that observed in a living human intestine.

BACKGROUND OF THE INVENTION

The diverse bacterial populations that comprise the commensal microbiota of the human intestine play a central role in health and disease, yet no method is available to sustain these complex microbial communities in direct contact with living human intestinal cells in vitro. The present disclosure describes a human Gut-on-a-Chip (Gut Chip) microfluidic platform that permits control and real-time assessment of physiologically-relevant oxygen gradients, and which enables co-culture of living human intestinal epithelium in direct contact with stable communities of aerobic and anaerobic microbiota derived from human stool specimens. When compared to aerobic co-culture conditions, establishment of a transluminal hypoxia gradient sustained higher microbial diversity with over 200 unique operational taxonomic units (OTUs) from 11 different genera, and an abundance of obligate anaerobic bacteria with ratios of Firmicutes and Bacteroidetes similar to those observed in human feces, in addition to increasing intestinal barrier function. The ability to culture human intestinal epithelium overlaid by complex human gut microbial communities may enable investigations of host-microbiome interactions that were not possible previously, and serve as a discovery tool for development of new microbiome-related therapeutics, probiotics, and nutraceuticals.

One of the major recent paradigm shifts in medicine relates to the recognition of the central role that the microbiome composed of host-specific communities of commensal microbes plays in human health and disease. Although human microbiota colonize mucosal surfaces of various tissues, the gastrointestinal (GI) tract supports the greatest mass and diversity of microorganisms. Aerobic and anaerobic commensal gut microbiota are essential for maintenance of normal nutrient absorption, drug metabolism, and immune responses, as well as for protection against infectious pathogens. Conversely, changes or imbalances in the microbial community within the intestine can contribute to development of a broad range of pathological disorders within and beyond the GI system, including inflammatory bowel disease, colorectal cancer, radiation enteropathy, diabetes, hepatic steatosis, obesity, and rheumatoid arthritis. Thus, the establishment and preservation of balanced host-intestinal microbiome interactions are key requirements for maintaining gut homeostasis and human health.

Analysis of gut-microbiome crosstalk has almost exclusively relied on genomic or metagenomic analysis of samples collected in vivo because no method exists to establish stable complex communities of gut commensal microbes in direct contact with intestinal epithelium in vitro. Although animal models have been used to analyze host-microbiome interactions and their contributions to pathophysiology, microbiota differ between different species.

Existing in vitro models, such as Transwell inserts, have been used to study human host-microbe interactions; however, these studies can only be carried out over a period hours before bacterial overgrowth leads to cell injury and death. More advanced models, such as organoid cultures, have shown great promise for studying host-microbiome interactions, but they are limited in providing a vascular interface and oxygen gradients with below 1% luminal oxygen levels required for co-culture of certain strict anaerobes. Human intestinal epithelial cells have been grown in a microfluidic culture device separated by a nanoporous membrane from a single facultative anaerobic bacterium (*Lactobacillus rhamnosus* GG) and an obligate anaerobe (*Bacteroides caccae*) cultured under anaerobic conditions in a parallel channel, which can permit analysis of the effects of soluble mediators, but not the impact of direct contact between host cells and a complex community of commensal microbes. A 2-channel, microfluidic, human Gut Chip device has been previously described as being lined by human Caco-2 intestinal epithelial cells culture under dynamic fluid flow and peristalsis-like mechanical deformations, which enabled establishment of stable co-cultures of a human villus intestinal epithelium in direct contact with up to 8 different strains of human commensal gut microbes for weeks in vitro under oxygenated conditions[1], but the living intestinal microbiome contains hundreds of different types of bacteria that are anaerobes as well as aerobes.

Thus, there is a great need for experimental models that can sustain complex populations of human aerobic and anaerobic microbiota in contact with living human tissues to analyze dynamic and physiologically relevant human host-microbiome interactions. According to another need, an experimental system is required that can support dynamic interactions between living human intestinal epithelium and a directly apposed complex community of living human aerobic and anaerobic commensal gut microbes with a population diversity similar to that observed in living human intestine.

SUMMARY OF THE INVENTION

Embodiment A1. According to one embodiment of the present disclosure, a microfluidic device is directed to sustaining a complex microbial community in direct and indirect contact with living human intestinal cells in vitro. The device includes a first microchannel having cultured cells of a human intestinal epithelium and microbiota, the first microchannel further having a first level of oxygen. The device further includes a second microchannel having cultured cells of a vascular endothelium, the second microchannel further having a second level of oxygen. The device also includes a membrane located at an interface region between the first microchannel and the second microchannel, the membrane being composed of an oxygen-permeable material or further having pores via which oxygen flows between the first microchannel and the second microchannel to form a physiologically-relevant oxygen gradient.

Embodiment A2. The microfluidic device of embodiment A1, further comprising a plurality of microscale oxygen sensors embedded in the first microchannel and the second microchannel, the plurality of microscale oxygen sensors providing real-time oxygen measurements based on non-invasive monitoring of the physiologically-relevant oxygen gradient.

Embodiment A3. The microfluidic device of embodiment A2, wherein the plurality of microscale oxygen sensors contain oxygen-quenched fluorescent particles.

Embodiment A4. The microfluidic device of embodiment A3, wherein the oxygen-quenched fluorescent particles are suspended in a polydimethylsiloxane (PDMS) polymer or other gas-permeable polymer.

Embodiment A5. The microfluidic device of embodiment A3, wherein the oxygen-quenched fluorescent particles are cured in a film having a thickness of between about 50 and 1,000 micrometers ($\mu$m).

Embodiment A6. The microfluidic device of embodiment A3, wherein the oxygen-quenched fluorescent particles are in the form of discs having a diameter of about 0.1-5 millimeters (mm).

Embodiment A7. The microfluidic device of embodiment A2, wherein the plurality of microscale oxygen sensors are placed directly on an interior surface of at least one of the first microchannel and the second microchannel.

Embodiment A8. The microfluidic device of embodiment A2, wherein the plurality of microscale oxygen sensors of are placed at an inlet region, a middle region, and an outlet region of each of the first microchannel and the second microchannel.

Embodiment A9. The microfluidic device of embodiment A2, wherein changes in fluorescent intensities of the plurality of microscale oxygen sensors are caused by oxygen tension, the changes being indicative of oxygen concentrations.

Embodiment A10. The microfluidic device of embodiment A1, wherein the first microchannel is a top microchannel and the second microchannel is a bottom microchannel.

Embodiment A11. The microfluidic device of embodiment A1, wherein the cultured cells of the vascular endothelium are human intestinal microvascular endothelia cells (HIMECs).

Embodiment A12. The microfluidic device of embodiment A1, wherein the physiologically-relevant oxygen gradient is a hypoxia gradient.

Embodiment B1. According to another embodiment of the present disclosure, an in vitro system is directed to emulating a living human intestine. The system includes a hypoxic chamber containing living human commensal gut microbes and cultured cells of a human intestinal epithelium in which the microbes are in direct and indirect contact with the cultured cells. The hypoxic chamber is configured to establish a physiologically-relevant oxygen gradient across the layer of microbes and cultured cells.

Embodiment B2. The in vitro system of embodiment B1, further comprising a plurality of microscale oxygen sensors providing real-time oxygen measurements based on non-invasive monitoring of the oxygen gradient.

Embodiment B3. The in vitro system of embodiment B1, wherein the cultured cells include one or more of mammalian cells, gut cells of insects, and gut cells of amphibians.

Embodiment B4. The in vitro system of embodiment B1, further comprising a mucus layer in contact with the cultured cells, the mucus layer being secreted by the cultured cells or separately provided.

Embodiment B5. The in vitro system of embodiment B1, wherein the microbes are contained in a layer.

Embodiment B6. The in vitro system of embodiment B5, wherein the layer of microbes and the cultured cells are placed within a microchannel.

Embodiment B7. The in vitro system of embodiment B6, wherein the microchannel is a top microchannel that is separated from a bottom microchannel via a membrane located at an interface region, the membrane being oxygen permeable or having a plurality of pores via which oxygen flows between the top microchannel and the bottom microchannel to achieve the oxygen gradient.

Embodiment B8. The in vitro system of embodiment B7, further comprising a plurality of microscale oxygen sensors providing real-time oxygen measurements based on non-invasive monitoring of the oxygen gradient, the plurality of microscale oxygen sensors being embedded in at least one of the top microchannel and the bottom microchannel.

Embodiment B9. The in vitro system of embodiment B7, wherein the oxygen gradient is based on top oxygen permeability through a device body to an external environment maintained at about 0 percent oxygen.

Embodiment B10. The in vitro system of embodiment B1, further comprising a Charge-Coupled Device (CCD) camera, a photodiode, or other light-sensing modality via which fluorescence read-out measurements provide the real-time oxygen measurements in a non-invasive manner.

Embodiment C1. According to another embodiment of the present disclosure, a method is directed to establishing a stable complex community of gut commensal microbes in vitro. The method includes providing cultured cells of an intestinal epithelium and microbiota in an environment having a first level of oxygen, the microbiota being in direct and indirect contact with the intestinal epithelium. The method also includes providing cultured cells of a vascular endothelium in an environment having a second level of oxygen, the second level of oxygen having a greater oxygen concentration than the first level of oxygen. The method further includes facilitating the flux of oxygen between the first level of oxygen and the second level of oxygen to form a physiologically-relevant oxygen gradient.

Embodiment C2. The method of embodiment C1, further comprising monitoring the oxygen gradient in a non-invasive manner, and measuring values of the oxygen gradient.

Embodiment C3. The method of embodiment C1, further comprising measuring the values of the oxygen gradient via a non-invasive fluorescence read-out.

Embodiment C4. The method of embodiment C1, further comprising providing oxygenation of the cultured cells of the intestinal epithelium and the cultured cells of the vascular endothelium while simultaneously providing an anaerobic environment for growth of obligate anaerobes.

Embodiment C5. The method of embodiment C1, further comprising achieving an oxygen concentration of less than approximately 0.5-2.0% in the first level of oxygen.

Embodiment C6. The method of embodiment C1, wherein the non-invasive manner includes positioning a camera directly beneath the cultured cells of the intestinal epithelium, the camera providing images of the cultured cells of the intestinal epithelium and microbiota.

Embodiment C7. The method of embodiment C1, wherein the cultured cells include one or more cells of non-gut organs with low oxygen tension.

Embodiment C8. The method of embodiment C7, wherein the non-gut organs include one or more of an oral mucosa, urinary tract, and genital mucosa.

Embodiment D1. According to yet another embodiment of the present disclosure, a microfluidic device has a first microchannel comprising a plurality of living parenchyma cells in direct contact with a plurality of living microbes, wherein the microbes are derived from a mammalian fecal sample.

Embodiment D2. The microfluidic device of embodiment D1, wherein the parenchyma cells are selected from the group consisting of cells of the small intestine, ilea, duodenum, lung, alveolar, and skin.

Embodiment D3. The microfluidic device of embodiment D1, wherein the mammal is a human.

Embodiment D4. The microfluidic device of embodiment D1, further comprising a second microchannel.

Embodiment D5. The microfluidic device of embodiment D4, wherein the first and second microchannels comprise media.

Embodiment D6. The microfluidic device of embodiment D4, wherein the media in the second microchannel is oxygenated.

Embodiment D7. The microfluidic device of embodiment D4, wherein the device has a gas gradient.

Embodiment D8. The microfluidic device of embodiment D7, wherein the gas in the first microchannel is at a lower concentration than the gas in the second microchannel.

Embodiment D9. The microfluidic device of embodiment D8, wherein the gas is selected from the group consisting of oxygen, nitrogen and carbon dioxide.

Embodiment D10. The microfluidic device of embodiment D4, wherein the second microchannel comprises living endothelial cells.

Embodiment D11. The microfluidic device of embodiment D1, wherein the plurality of microbes comprises both anaerobic bacteria and aerobic bacteria.

Embodiment D12. The microfluidic device of embodiment D1, wherein the plurality of microbes comprises both Firmicutes phyla and Bacteroidetes phyla.

Embodiment D13. The microfluidic device of embodiment D1, wherein the Firmicutes species are selected from the group consisting of *Akkermansia, Oscillospira, Blautia* and *Suterella* species.

Embodiment D14. The microfluidic device of embodiment D1, wherein the plurality of microbes comprises *Coprococcus, Anaerobacillus, Bifidobacterium*, and *Peptoniphilus* species.

Embodiment D15. The microfluidic device of embodiment D1, wherein the plurality of microbes comprises at least 8 different genera of bacteria found in human feces.

Embodiment D16. The microfluidic device of embodiment D15, wherein the plurality of microbes comprises at least 11 different genera of bacteria found in human feces.

Embodiment E1. According to yet another embodiment of the present disclosure, a method includes a) providing, i) a mammalian fecal sample comprising living microbes, and ii) a solution of fluid; b) suspending at least a portion of the fecal sample in the solution so as to create a fecal slurry comprising living microbes; c) filtering the slurry so as to generate a microbiome stock derived directly from a fecal sample; d) diluting the microbiome stock so as to create a diluted stock; e) introducing the diluted stock into a microfluidic device; and f) culturing the diluted stock in the microfluidic device so as to create a cultured microbiome of living microbes.

Embodiment E2. The method of embodiment E1, wherein one or more steps of the method take place in an anaerobic chamber.

Embodiment E3. The method of embodiment E2, wherein the suspending takes place inside the anaerobic chamber.

Embodiment E4. The method of embodiment E1, wherein the mammalian fecal sample is from a human.

Embodiment E5. The method of embodiment E4, wherein the human is selected from the group consisting of a preterm infant, infant, child, teen, and an adult.

Embodiment E6. The method of embodiment E4, wherein the fecal sample is from a diaper.

Embodiment E7. The method of embodiment E4, wherein the fecal sample is a stool sample.

Embodiment E8. The method of embodiment E4, wherein the fecal sample was obtained during a medical procedure.

Embodiment E9. The method of embodiment E1, wherein the fecal portion is suspended at 100 mg·ml$^{-1}$ for creating the fecal slurry.

Embodiment E10. The method of embodiment E4, wherein the fecal sample of step a) was not passed through another mammal.

Embodiment E10. The method of embodiment E4, wherein the fecal sample of step a) was not cultured in vitro.

Embodiment E11. The method of embodiment E4, wherein the fecal sample comprises both anaerobic bacteria and aerobic bacteria.

Embodiment E12. The method of embodiment E1, wherein the diluting of the microbiome stock generates a concentration of microbes of approximately $1 \times 10^7$ CFU ml$^{-1}$.

Embodiment E13. The method of embodiment E1, wherein the filtering of step c) is done with a filter that has a 40 μm pore size or less.

Embodiment E14. The method of embodiment E1, wherein the cultured microbiome comprises organisms from both the Firmicutes phyla and the Bacteroidetes phyla.

Embodiment E15. The method of embodiment E1, wherein the cultured microbiome comprises species selected from the group consisting of *Akkermansia, Oscillospira, Blautia* and *Suterella* species.

Embodiment E16. The method of embodiment E1, wherein the cultured microbiome comprises *Coprococcus*, *Anaerobacillus*, *Bifidobacterium*, and *Peptoniphilus* species.

Embodiment E17. The method of embodiment E1, wherein the cultured microbiome comprises at least 8 different genera of bacteria found in human feces.

Embodiment E18. The method of embodiment E1, wherein the cultured microbiome comprises at least 11 different genera of bacteria found in human feces.

Embodiment E19. The method of embodiment E13, further comprising g) flushing media through the cultured microbiome in the microfluidic device.

Embodiment E20. The method of embodiment E19, wherein the flushing provides a sample of cultured living microbes.

Embodiment E21. The method of embodiment E1, wherein the microfluidic device comprises a first microchannel comprising a plurality of living parenchyma cells.

Embodiment E22. The method of embodiment E21, wherein the introducing of step e) results in the parenchyma cells being in direct contact with a plurality of living microbes.

Embodiment E23. The method of embodiment E22, wherein the parenchyma cells are selected from the group consisting of cells of the small intestine, ilea, duodenum, lung, alveolar, and skin.

Embodiment E24. The method of embodiment E23, wherein the cells are intestinal epithelial cells.

Embodiment E25. The method of embodiment E21, wherein the microfluidic device further comprises a second microchannel.

Embodiment E26. The method of embodiment E25, wherein the first and second microchannels comprise media.

Embodiment E27. The method of embodiment E26, wherein the media in the second microchannel is oxygenated.

Embodiment E28. The method of embodiment E26, wherein the microfluidic device has a gas gradient.

Embodiment E29. The method of embodiment E28, wherein the gas in the first microchannel is at a lower concentration than the gas in the second microchannel.

Embodiment E30. The method of embodiment E29, wherein the gas is selected from the group consisting of oxygen, nitrogen and carbon dioxide.

Embodiment E31. The method of embodiment E25, wherein the second microchannel comprises living endothelial cells.

Embodiment E32. The method of embodiment E28, wherein the gas gradient provides at least one hypoxic region in the first microchannel.

Embodiment E33. The method of embodiment E26, wherein the culturing comprises flowing media at a flow rate.

Embodiment E34. The method of embodiment E26, wherein the second microchannel is positioned below the first microchannel and separated from the first microchannel by a membrane.

Embodiment E35. The method of embodiment E34, wherein oxygenated medium flows through the second microchannel from external oxygenated medium reservoirs.

Embodiment E36. The method of embodiment E35, wherein parenchyma cells in the first microchannel get oxygen from the second microchannel.

Embodiment E37. The method of embodiment E1, wherein the culturing takes place for at least 2 days.

Embodiment E38. The method of embodiment E1, wherein the culturing takes place for at least 3 days.

Embodiment E39. The method of embodiment E1, wherein the culturing takes place for at least 5 days.

Embodiment E40. The method of embodiment E38, wherein cultured microbiome comprises both anaerobic bacteria and aerobic bacteria.

Embodiment E41. The method of embodiment E40, wherein the cultured microbiome comprises at least 2 anaerobic species found in the fecal sample.

Embodiment E42. The method of embodiment E40, wherein the cultured microbiome comprises microbes from at least 2 genera found in the fecal sample.

Embodiment F1. According to yet another embodiment of the present disclosure, a method includes a) providing a microfluidic device and a portion of a mammalian fecal sample, the portion comprising living microbes; b) introducing the portion into the microfluidic device; and c) culturing the living microbes in the microfluidic device so as to create a cultured microbiome.

Embodiment F2. The method of embodiment F1, wherein, prior to the introducing of step b) the portion of the fecal sample is suspended in a sterile solution so as to create a fecal slurry.

Embodiment F3. The method of embodiment F2, wherein the suspending takes place inside an anaerobic chamber.

Embodiment F4. The method of embodiment F2, wherein, after the suspending, the slurry is passed through a filter, so as to generate a microbiome stock derived directly from a fecal sample.

Embodiment F5. The method of embodiment F4, wherein the filter has a 40 μm pore size or less.

Embodiment F6. The method of embodiment F4, further comprising diluting the microbiome stock so as to create a diluted stock, the diluted stock being introduced in step b).

Embodiment F7. The method of embodiment F6, wherein the diluting the microbiome stock generates a concentration of microbes of approximately $1 \times 10^7$ CFU ml$^{-1}$.

Embodiment F8. The method of embodiment F1, wherein the mammalian fecal sample is from a human.

Embodiment F9. The method of embodiment F8, wherein the human is selected from the group consisting of a preterm infant, infant, child, teen, and an adult.

Embodiment F10. The method of embodiment F8, wherein the fecal sample is from a diaper.

Embodiment F11. The method of embodiment F8, wherein the fecal sample is a stool sample.

Embodiment F12. The method of embodiment F8, wherein the fecal sample was obtained during a medical procedure.

Embodiment F13. The method of embodiment F2, wherein the fecal portion is suspended at 100 mg·ml$^{-1}$.

Embodiment F14. The method of embodiment F8, wherein the fecal sample of step a) was not passed through another mammal.

Embodiment F15. The method of embodiment F8, wherein the fecal sample of step a) was not cultured in vitro.

Embodiment F16. The method of embodiment F1, wherein the fecal sample comprises both anaerobic bacteria and aerobic bacteria.

Embodiment F17. The method of embodiment F16, wherein the cultured microbiome comprises at least one of the same anaerobic bacteria types and aerobic bacteria types of the fecal sample.

Embodiment F18. The method of embodiment F1, wherein the cultured microbiome comprises both Firmicutes phyla and Bacteroidetes phyla.

Embodiment F19. The method of embodiment F1, wherein the cultured microbiome comprises species selected from the group consisting of *Akkermansia, Oscillospira, Blautia* and *Suterella* species.

Embodiment F20. The method of embodiment F1, wherein the cultured microbiome comprises *Coprococcus, Anaerobacillus, Bifidobacterium*, and *Peptoniphilus* species.

Embodiment F21. The method of embodiment F1, wherein the cultured microbiome comprises at least 8 different genera of bacteria found in human feces.

Embodiment F22. The method of embodiment F1, wherein the cultured microbiome comprises at least 11 different genera of bacteria found in human feces.

Embodiment F23. The method of embodiment F1, further comprising d) flushing media through the cultured microbiome in the microfluidic device.

Embodiment F24. The method of embodiment F23, wherein the flushing provides a sample of cultured living microbes.

Embodiment F25. The method of embodiment F1, wherein the microfluidic device comprises a first microchannel comprising a plurality of living parenchyma cells.

Embodiment F26. The method of embodiment F25, wherein the introducing of step b) results in the parenchyma cells being in direct contact with a plurality of living microbes.

Embodiment F27. The method of embodiment F25, wherein the parenchyma cells are selected from the group consisting of cells of the small intestine, ilea, duodenum, lung, alveolar, and skin.

Embodiment F28. The method of embodiment F27, wherein the cells are intestinal epithelial cells.

Embodiment F29. The method of embodiment F25, wherein the microfluidic device further comprises a second microchannel.

Embodiment F30. The method of embodiment F29, wherein the first and second microchannels comprise media.

Embodiment F31. The method of embodiment F30, wherein the media in the second microchannel is oxygenated.

Embodiment F32. The method of embodiment F29, wherein the microfluidic device has a gas gradient.

Embodiment F33. The method of embodiment F32, wherein the gas in the first microchannel is at a lower concentration than the gas in the second microchannel.

Embodiment F34. The method of embodiment F33, wherein the gas is selected from the group consisting of oxygen, nitrogen and carbon dioxide.

Embodiment F35. The method of embodiment F29, wherein the second microchannel comprises living endothelial cells.

Embodiment F36. The method of embodiment F32, wherein the gas gradient provides anaerobic conditions in the first microchannel.

Embodiment F37. The method of embodiment F25, wherein the introducing of step b) results in the parenchyma cells being in direct contact with living obligate anaerobes.

Embodiment F38. The method of embodiment F1, wherein the culturing comprises flowing media at a flow rate.

Embodiment F39. The method of embodiment F29, wherein the second microchannel is positioned below the first microchannel and separated from the first microchannel by a membrane.

Embodiment F40. The method of embodiment F39, wherein oxygenated medium flows through the second microchannel from external oxygenated medium reservoirs.

Embodiment F41. The method of embodiment F40, wherein parenchyma cells in the first microchannel get oxygen from the second microchannel.

Embodiment F42. The method of embodiment F1, wherein the culturing takes place for at least 2 days.

Embodiment F43. The method of embodiment F1, wherein the culturing takes place for at least 3 days.

Embodiment F44. The method of embodiment F1, wherein the culturing takes place for at least 5 days.

Embodiment F45. The method of embodiment F43, wherein cultured microbiome comprises both anaerobic bacteria and aerobic bacteria.

Embodiment F46. The method of embodiment F43, wherein the cultured microbiome comprises at least 2 anaerobic species found in the fecal sample.

Embodiment F47. The method of embodiment F43, wherein the cultured microbiome comprises microbes from at least 2 genera found in the fecal sample.

Embodiment G1. According to yet another embodiment of the present disclosure, a method includes a) providing a microfluidic device and living microbes from the surface or contents of a body, orifice or cavity; b) introducing at least a portion of the living microbes into the microfluidic device; and c) culturing the living microbes in the microfluidic device so as to create a cultured microbiome.

Embodiment G2. The method of embodiment G1, where the surface of a body is skin.

Embodiment G3. The method of embodiment G1, wherein the content of a body is saliva.

Embodiment G4. The method of embodiment G1, wherein the body is the body of a mammal.

Embodiment G5. The method of embodiment G1, wherein the body is the body of a non-mammal.

Embodiment G6. The method of embodiment G5, wherein the non-mammal is a bird.

Embodiment G7. The method of embodiment G1, wherein the culturing comprises flowing media at a flow rate.

Embodiment G8. The method of embodiment G7, wherein the microfluidic device comprises a second microchannel positioned below a first microchannel and separated from the first microchannel by a membrane.

Embodiment G9. The method of embodiment G8, wherein oxygenated medium flows through the second microchannel from external oxygenated medium reservoirs.

Embodiment G10. The method of embodiment G9, wherein living parenchyma cells are in the first microchannel.

Embodiment G11. The method of embodiment G10, wherein the living parenchyma cells get oxygen from the second microchannel.

Embodiment H1. According to yet another embodiment of the present disclosure, a method includes a) providing a microfluidic device, a source of microbes comprising living obligate anaerobes and living parenchyma cells; and b) culturing the obligate anaerobes and the parenchyma cells in the microfluidic device such that at least a portion of the obligate anaerobes and at least a portion of the parenchyma cells are in direct contact.

Embodiment H2. The method of embodiment H1, wherein the living obligate anaerobes are from the surface or contents of a body, orifice or cavity.

Embodiment H3. The method of embodiment H1, wherein the parenchyma cells are human intestinal epithelial cells.

Embodiment H4. The method of embodiment H1, wherein, after the culturing, unknown microbes are identified.

Embodiment H5. The method of embodiment H1, wherein the culturing comprises flowing media at a flow rate.

Embodiment H6. The method of embodiment H1, wherein the microfluidic device comprises a second microchannel positioned below a first microchannel and separated from the first microchannel by a membrane.

Embodiment H7. The method of embodiment H6, wherein oxygenated medium flows through the second microchannel from external oxygenated medium reservoirs.

Embodiment H8. The method of embodiment H7, wherein parenchyma cells in the first microchannel get oxygen from the second microchannel.

Embodiment H9. The method of embodiment H1, wherein the culturing takes place for at least 2 days.

Embodiment H10. The method of embodiment H1, wherein the culturing takes place for at least 3 days.

Embodiment H11. The method of embodiment H1, wherein the culturing takes place for at least 5 days.

Embodiment H12. The method of embodiment H10, wherein cultured microbiome comprises both anaerobic bacteria and aerobic bacteria.

Embodiment H13. The method of embodiment H10, wherein the cultured microbiome comprises at least 2 anaerobic species found in the fecal sample.

Embodiment H14. The method of embodiment H10, wherein the cultured microbiome comprises microbes from at least 2 genera found in the fecal sample.

Embodiment I1. According to yet another embodiment of the present disclosure, a method includes a) providing, i) a liquid sample derived from a culture of a plurality of microbes of different types, and ii) a first microfluidic device capable of undergoing fluid flow, comprising living parenchymal cells in a first microchannel; and b) flowing said liquid sample into said first microchannel so that at least a portion of said sample contacts said living parenchymal cells.

Embodiment I2. The method of embodiment I1, further comprising c) detecting an effect of said liquid sample on said living parenchymal cells.

Embodiment I3. The method embodiment I1, wherein said parenchymal cells are intestinal epithelial cells.

Embodiment I4. The method of embodiment I1, wherein said liquid sample is derived from a second microfluidic device comprising a microbiome.

Embodiment I5. The method of embodiment I4, wherein said microbiome was created by inoculating said second microfluidic device with a plurality of microbes derived from a fecal sample.

Embodiment I6. The method of embodiment 14, wherein said second microfluidic device has an outlet and said liquid sample was collected from said outlet as an effluent.

Embodiment I7. The method of embodiment 14, wherein said microbiome comprises anaerobic and aerobic bacteria.

Embodiment I8. The method of embodiment 17, wherein said microbiome was inoculated with a plurality of enterohemorrhagic *Escherichia coli* (EHEC).

Embodiment I9. The method of embodiment I1, wherein said first microfluidic device was inoculated with a plurality of enterohemorrhagic *Escherichia coli* (EHEC).

Embodiment I10. The method of embodiment I1, wherein said liquid sample comprises one or more metabolite compounds generated by said microbes.

Embodiment I11. The method of embodiment I1, wherein said liquid sample does not contain a living microbe.

Embodiment I12. The method of embodiment 13, wherein said intestinal epithelial cells are derived from a patent biopsy.

Embodiment I13. The method of claim 3, wherein said intestinal epithelial cells have a plurality of microvilli.

Embodiment I14. The method of embodiment I1, further comprising: i) providing a test compound, and ii) flowing said test substance into said first microchannel.

Embodiment I15. The method of embodiment I1, wherein said first microfluidic device further comprises a second microfluidic channel, separated by a membrane from said first microfluidic channel.

Embodiment I16. The method of embodiment 115, wherein said second microfluidic channel comprises endothelial cells.

Embodiment I17. The method of embodiment 116, further comprising: i) providing a test compound, and ii) flowing said test substance into said second microchannel.

Embodiment I18. The method of embodiment I10, wherein said one or more metabolites are selected from the group consisting of 4-methyl benzoic acid, 3,4-dimethylbenzoic acid, hexanoic acid, and heptanoic acid.

Embodiment J1. According to yet another embodiment of the present disclosure, a method includes a) providing a microfluidic device capable of undergoing fluid flow, comprising living parenchymal cells in contact with a plurality of diverse microbes in a first microchannel or chamber, wherein said microfluidic device has an outlet at the end of said first microchannel or chamber; b) flowing liquid into said first microchannel or chamber; and c) collecting effluent at said outlet.

Embodiment J2. The method of embodiment J1, further comprising d) testing said effluent.

Embodiment J3. The method of embodiment J2, wherein said testing comprises flowing at least a portion of said effluent into a second microfluidic device comprising cells.

Additional aspects of the disclosure will be apparent to those of ordinary skill in the art in view of the detailed description of various embodiments, which is made with reference to the drawings, a brief description of which is provided below.

BRIEF DESCRIPTION OF THE DRAWINGS

FIG. 1A is a schematic representation showing the position of a human intestinal epithelium and microbiota on top.

FIG. 1B is a schematic representation of a Gut Chip with 6 oxygen quenched fluorescent particles embed in inlet, middle and outlet of top and bottom channels (T, top channel; B, bottom channel).

FIG. 2A is a graph showing oxygen concentration profiles in aerobic and anaerobic Gut Chips co-cultured with *Bacteroides fragilis*.

FIG. 2B shows representative vertical cross-sectional, confocal micrographic views through the intestinal epithelium-microbiome interface within the Gut Chip.

FIG. 2C is a graph showing changes in apparent paracellular permeability ($P_{app}$).

FIG. 2D is a graph showing CFU counts of *Bacteroides fragilis* co-cultured in Gut Chip under aerobic and anaerobic conditions (n=3; *P<0.05, ***P<0.001).

FIG. 12 is a table showing media tested for microbial diversity.

FIG. 16A shows a differential interference contract (DIC) microscopic image of primary human ileum chips.

FIG. 16B shows a confocal fluorescence microscopic image of primary human ileum chips.

FIG. 16C is a graph showing a co-culture stably maintained for up to at least five days on-chip.

FIG. 16D is a table showing observed richness of various ileum samples.

Figure 1C:
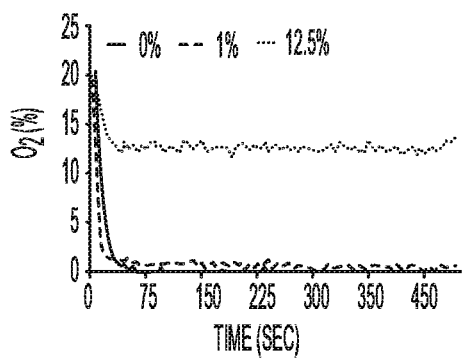
FIG. 1C is a graph showing sensitivity analysis of oxygen spots located in the Gut Chip in response to defined, standard oxygen concentrations.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION

As used herein, the phrases "linked," "connected to," "coupled to," "in contact with" and "in communication with" refer to any form of interaction between two or more entities, including mechanical, electrical, magnetic, electromagnetic, fluidic, and thermal interaction. For example, in one embodiment, channels in a microfluidic device are in fluidic communication with cells and (optionally) a fluid reservoir (or other components). Two components may be coupled to each other even though they are not in direct contact with each other. For example, two components may be coupled to each other through an intermediate component (e.g. tubing or other conduit).

"Channels" are pathways (whether straight, curved, single, multiple, in a network, etc.) through a medium (e.g., silicon, plastic, etc.) that allow for movement of liquids and gasses. Channels thus can connect other components, i.e., keep components "in communication" and more particularly, "in fluidic communication" and still more particularly, "in liquid communication." Such components include, but are not limited to, liquid-intake ports and gas vents.

"Microchannels" are channels with dimensions less than 1 millimeter and greater than 1 micron. Additionally, the term "microfluidic" as used herein relates to components where moving fluid is constrained in or directed through one or more channels wherein one or more dimensions are 1 mm or smaller (microscale). Microfluidic channels may be larger than microscale in one or more directions, though the channel(s) will be on the microscale in at least one direction. In some instances the geometry of a microfluidic channel may be configured to control the fluid flow rate through the channel (e.g. increase channel height to reduce shear). Microfluidic channels can be formed of various geometries to facilitate a wide range of flow rates through the channels.

The present invention contemplates a variety of "microfluidic devices," including but not limited to microfluidic chips (such as that shown in FIGS. 1A and 1B). Some microfluidic devices comprise one or more microchannels with cells and culture media. For example, in one embodiment, the present invention contemplates oxygenated medium flowing through the lower endothelium-lined vascular channel from external oxygenated medium reservoirs. In this embodiment, epithelial cells in the upper channel get oxygen from the lower channel (e.g. through a porous membrane, gel, pillars etc. or a combination thereof).

A "hypoxic chip" or "hypoxic microfluidic device" comprises a device with one or more hypoxic regions. Such regions have low levels of oxygen, i.e. 5% or lower, more preferably 4% or lower, 3% or lower, 2% or lower, 1% or lower, 0.5% or lower, or 0.1% or lower. That is to say, the entire device need not be hypoxic. Moreover, it is not intended that the present invention be limited to how a hypoxic region is generated. Hypoxic conditions can be generated with a chamber (as shown in FIG. 6) or without a chamber. Hypoxic conditions can be generated in a microfluidic device that is not gas permeable, or that has a region that is not gas permeable. Hypoxic conditions can be generated using deoxygenated media. Of course, these different approaches can be combined, if desired.

An "aerobic chip" is a microfluidic device where steps have not been taken to create hypoxic conditions (e.g. no hypoxic chamber, no deoxygenated media, etc.). Nonetheless, system components in an aerobic chip may regulate oxygen to support co-culture of anaerobes with mammalian cells. In particular, and without being bound by theory, the mammalian cells consume oxygen that is predominantly delivered to them from their basal side; this reduces the concentration of oxygen on the anaerobes. In addition, and without being bound by theory, other elements of the complex microbiome, for example aerobes present, also consume remaining oxygen that may otherwise poison or inhibit growth of the anaerobes.

While a microbiome is exemplified herein using a fecal sample, the present invention contemplates other sources for generating a microbiome in a microfluidic device, including but not limited to skin, saliva, lung, armpit, toes, feet, etc. (e.g. any surface or contents of a body, orifice or cavity). Moreover, sources from both mammals and non-mammals can be used.

According to the present disclosure, an experimental system has been developed that can support dynamic interactions between living human intestinal epithelium and a directly apposed complex community of living human aerobic and anaerobic commensal gut microbes with a population diversity similar to that observed in living human intestine. To meet this challenge, a human Gut Chip was modified by culturing human intestinal microvascular endothelial cells (HIMECs) in a lower channel, integrating microscale oxygen sensors into the device for in situ oxygen measurements, and placing the Gut Chip within an engineered hypoxic chamber to establish a physiologically relevant oxygen gradient across the Gut Chip vascular and epithelium channels. To emulate the physiological human intestinal gut-microbiota interface on-chip, complex microbiota was derived from healthy human stool specimens, which have been maintained stably in gnotobiotic mice for multiple years. The disclosure below describes how to establish a hypoxia gradient across engineered tissue-tissue (endothelium-epithelium) interface of the Gut Chip, which allows stably co-culturing of complex communities of anaerobic and aerobic human commensal gut bacteria in direct contact with human villus intestinal epithelium while simultaneously monitoring oxygen levels for multiple days in vitro.

Referring to FIGS. 1A-1F, schematics and data illustrate an oxygen-sensitive human Gut chip microfluidic device. FIG. 1A a schematic representation showing the position of a human intestinal epithelium and microbiota on top and further shows a vascular endothelium on a bottom side of the matrix-coated porous membrane within a 2-channel microfluidic device in presence of oxygen gradients. High and low levels of oxygen concentration are also illustrated, with high levels being generally towards the bottom and high levels being generally towards the top. By way of example, Further referring to FIG. 1A, and by way of example, a microfluidic device 100 is configured to sustain a complex microbial community in direct and indirect contact with living human intestinal cells in vitro. The microfluidic device 100 includes a first microchannel 102 that has within cultured cells 104 of a human intestinal epithelium and microbiota. The first microchannel 102 has a first level of oxygen 108. The microfluidic device 100 further includes a second microchannel 110 that has within cultured cells 112 of a vascular endothelium. The second microchannel 110 has a second level of oxygen 114 that has a greater oxygen concentration than the first level of oxygen 108. In this example, the first microchannel 102 is a top microchannel and the second microchannel 110 is a bottom microchannel.

The microfluidic device 100 further includes a membrane 116 that is located at an interface region between the first microchannel 102 and the second microchannel 110. The membrane 116 has a first surface 118 facing the first microchannel 102 and a second surface 120 facing the second microchannel 110. The membrane is composed of an oxygen-permeable material or has a plurality of pores via which oxygen flows between the first microchannel 102 and the second microchannel 110 to form a physiologically-relevant oxygen gradient across the first microchannel 102 and the second microchannel 110.

The microfluidic device 100 optionally includes a plurality of microscale oxygen sensors 122 that contain oxygen-quenched fluorescent particles. The plurality of microscale oxygen sensors 122 are optionally placed directly on an interior surface of at least one of the first microchannel 102 and the second microchannel 110. The plurality of microscale oxygen sensors 122 are optionally placed at an inlet region 124, a middle region 126, and an outlet region 128 of each of the first microchannel 102 and the second microchannel 110. The oxygen-quenched fluorescent particles are optionally suspended in a polydimethylsiloxane (PDMS) polymer or other gas-permeable polymer. Optionally yet, the oxygen-quenched fluorescent particles are cured in a film having a thickness of between about 50 and 1,000 micrometers (µm). In another alternative embodiment, the oxygen-quenched fluorescent particles are in the form of discs having a diameter of about 0.1-5 millimeters (mm). Optionally yet, changes in fluorescent intensities of the plurality of microscale oxygen sensors 122 are caused by oxygen tension, the changes being indicative of oxygen concentrations. Other features or configurations of the microfluidic device 100 are described below in accordance with applicable experimental studies and data.

Figure 1D:
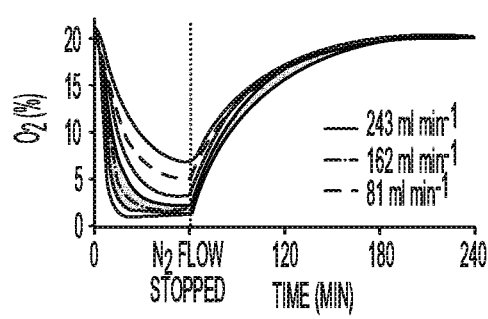
FIG. 1D is a graph showing hypoxic chamber validation at various $N_2$ inflow pressures.
Figure 1E:
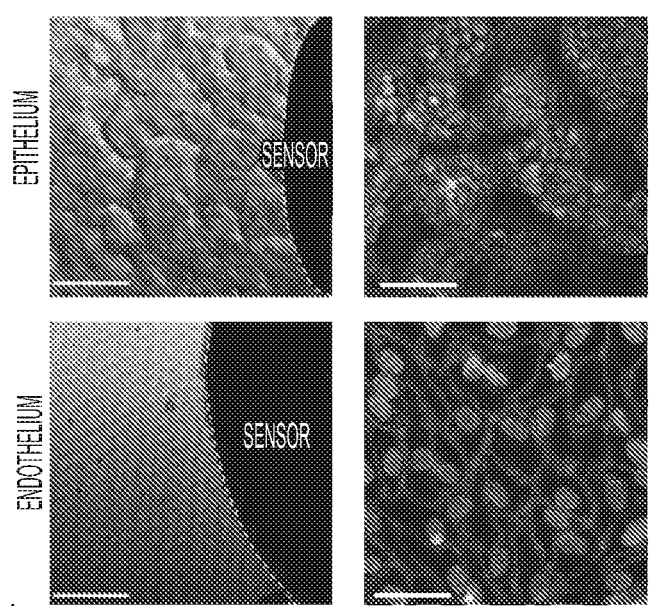
FIG. 1E shows microscopic views of villus morphology of the human Caco-2 intestinal epithelium (bar, 100 µm) and vascular endothelium (bottom left; bar, 100 µm).
Figure 1F:
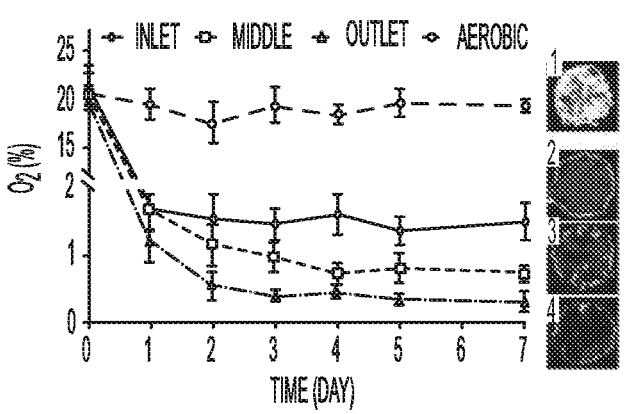
FIG. 1F is a graph showing oxygen concentration profiles within aerobically- and anaerobically-cultured Gut Chips.

FIG. 1B shows a Gut Chip with 6 oxygen quenched fluorescent particles embed in inlet, middle and outlet of top and bottom channels (T, top channel; B, bottom channel). FIG. 1C shows sensitivity analysis of oxygen spots located in the Gut Chip in response to defined, standard oxygen concentrations. FIG. 1D hypoxic chamber validation at various $N_2$ inflow pressures and further shows $N_2$ introduced into the chamber at 81 mL min$^{-1}$, 162 mL min$^{-1}$, or 243 mL min' for 1 h when gas flow was stopped and chamber was allowed to recover (n=3, shaded regions are standard deviation). FIG. 1E shows villus morphology of the human Caco-2 intestinal epithelium (bar, 100 µm) and vascular endothelium (bottom left; bar, 100 µm), and further shows the human Caco-2 intestinal epithelium and vascular endothelium cultured for 6 days in the Gut Chip under anaerobic condition, when viewed from above by DIC and phase contrast imaging, respectively, or by immunofluorescence staining for the tight junction protein, ZO-1 (red, top right; bar, 100 µm) and endothelial cell junction-associated protein, VE-cadherin (red, bottom right; bar, 20 µm). Gray indicates DAPI-stained nuclei. White dashed lines indicate borders of oxygen sensor spots). FIG. 1F shows oxygen concentration profiles within aerobically- and anaerobically-cultured Gut Chips, and further shows representative pseudocolor insets that indicate average oxygen concentration in aerobic chip (1), and inlet (2), middle (3) and outlet (4) of anaerobically-cultured epithelium channel at day 7 of culture.

Figure 2F:
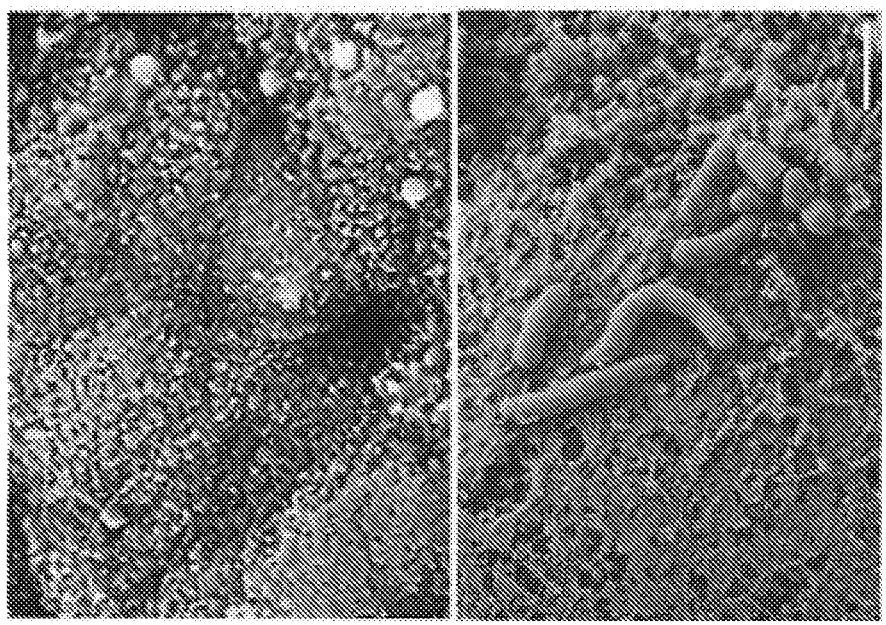
FIG. 2F shows representative images illustrating a continuous and dense mucus blanket after a number of culture days.
Figure 2E:
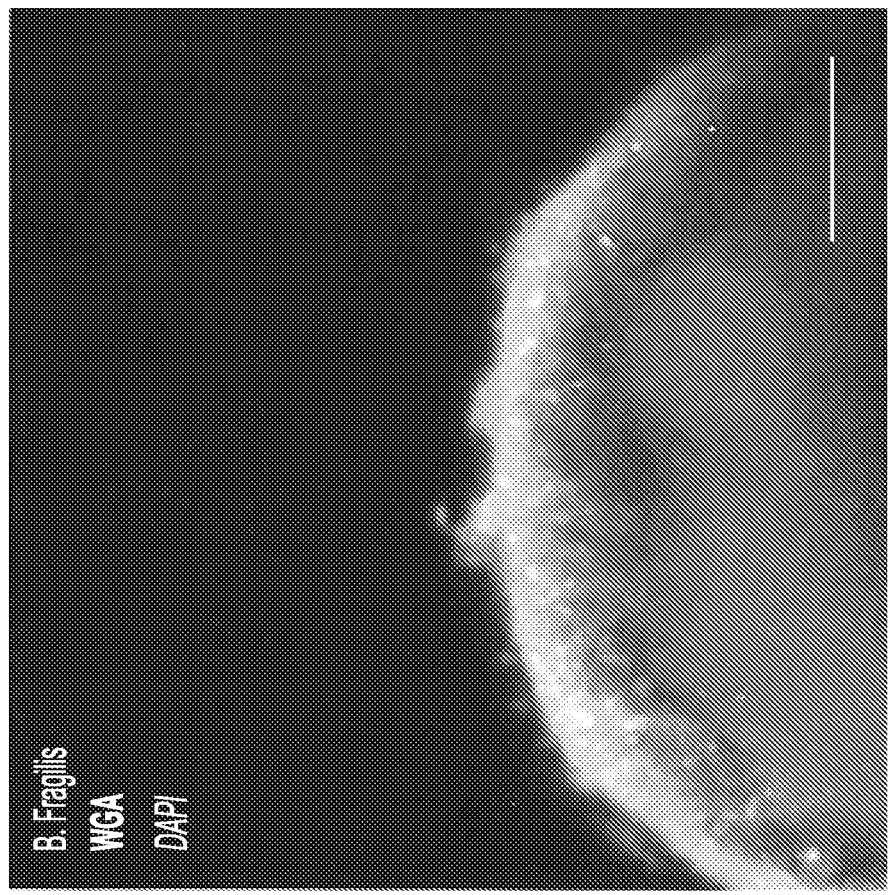
FIG. 2E is a representative image confirming that *Bacteroides fragilis* resides on top of a mucus layer.

Referring to FIGS. 2A-2F, representative images and data show co-culture of human intestinal epithelium and obligate anaerobe, Bacteroides fragilis, on-chip. FIG. 2A shows oxygen concentration profiles in aerobic and anaerobic Gut Chips co-cultured with Bacteroides fragilis. FIG. 2B shows vertical cross-sectional, confocal micrographic views through the intestinal epithelium-microbiome interface within the Gut Chip, and further shows the Gut Chip cultured under anaerobic condition, when immunostained for villin, ZO-1 nuclei with DAPI (bar, 50 µm). B. fragilis is HADA labeled. FIG. 2C shows changes in apparent paracellular permeability ($P_{app}$), which is measured by quantitating cascade blue transport across the tissue-tissue interface within the Gut Chip microdevices co-cultured with Bacteroides fragilis under aerobic and anaerobic conditions (n=4; *P<0.05). FIG. 2D shows CFU counts of Bacteroides fragilis co-cultured in Gut Chip under aerobic and anaerobic conditions (n=3; *P<0.05, ***P<0.001). FIG. 2E shows cross-sectional fluorescence microscopic view of the Caco2 epithelium (nuclei stained in blue with DAPI), overlying mucus layer stained with Alexa Fluor 488-conjugated WGA (yellow), and B. fragilis bacteria (GalCCP labelled, white) when co-cultured in the intestine chip (scale bar, 10 µm). FIG. 2F shows SEM views of the apical surface of the Caco2 epithelium in the intestine chip comparing the morphology on day 4 of culture before it accumulates a mucus layer and when the surface microvilli are visible (top) versus when Bacteroides fragilis have been added on day 12 after the mucus layer has accumulated, which can be seen as a dense mat that separates the bacteria from the epithelial cell surface (bottom) (scale bar, 2 µm).

Figure 3A:
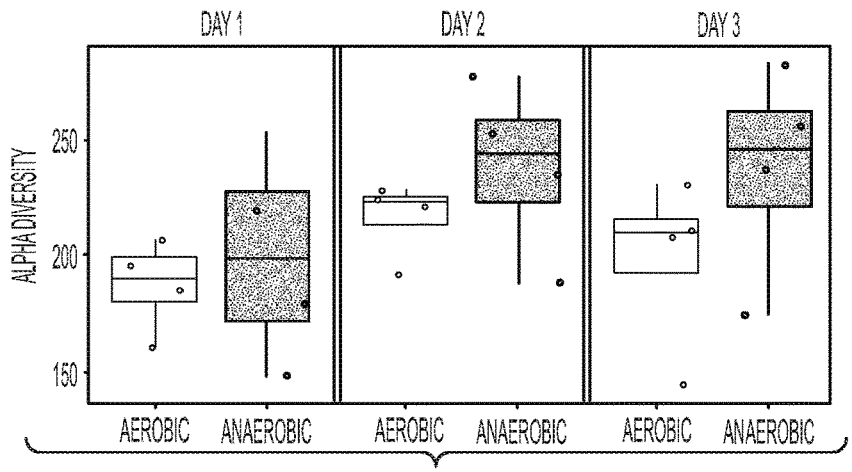
FIG. 3A is a graph showing observed alpha diversity in microbiome samples.
Figure 3B:
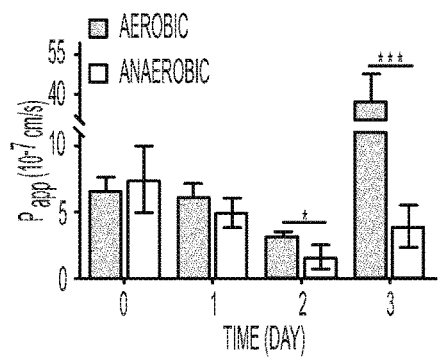
FIG. 3B is a graph showing changes in apparent paracellular permeability (Papp).
Figure 3C:
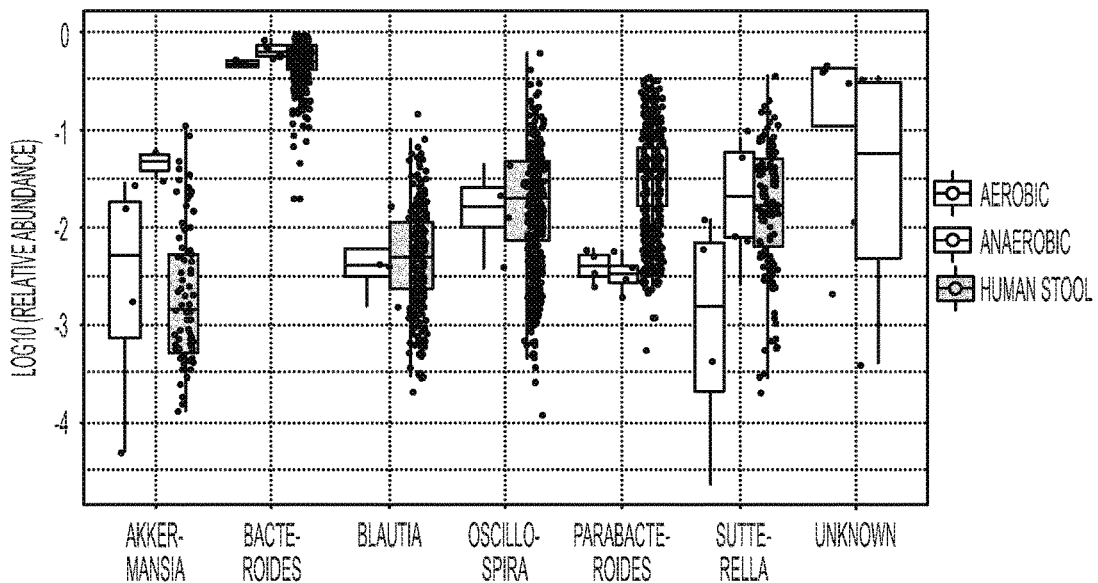
FIG. 3C is a graph showing aerobic, anaerobic, and human stool data.

Referring to FIGS. 3A-3C, representative graphs are generally directed to the analysis of the diversity and relative abundance of microbiota co-cultured in gut Chips under aerobic and anaerobic conditions. FIG. 3A shows observed alpha diversity in microbiome samples in both anaerobic and aerobic conditions, across 3 days of co-culturing of a microbiome sample with human intestinal epithelium. FIG. 3B shows changes in apparent paracellular permeability (Papp) measured by quantitating cascade blue transport across the tissue-tissue interface within the Gut Chip microdevices after diverse microbiome co-culture, under aerobic and anaerobic conditions (n=4; *P<0.05, ***P<0.001). FIG. 3C shows aerobic, anaerobic, and human stool data.

Figure 4A:
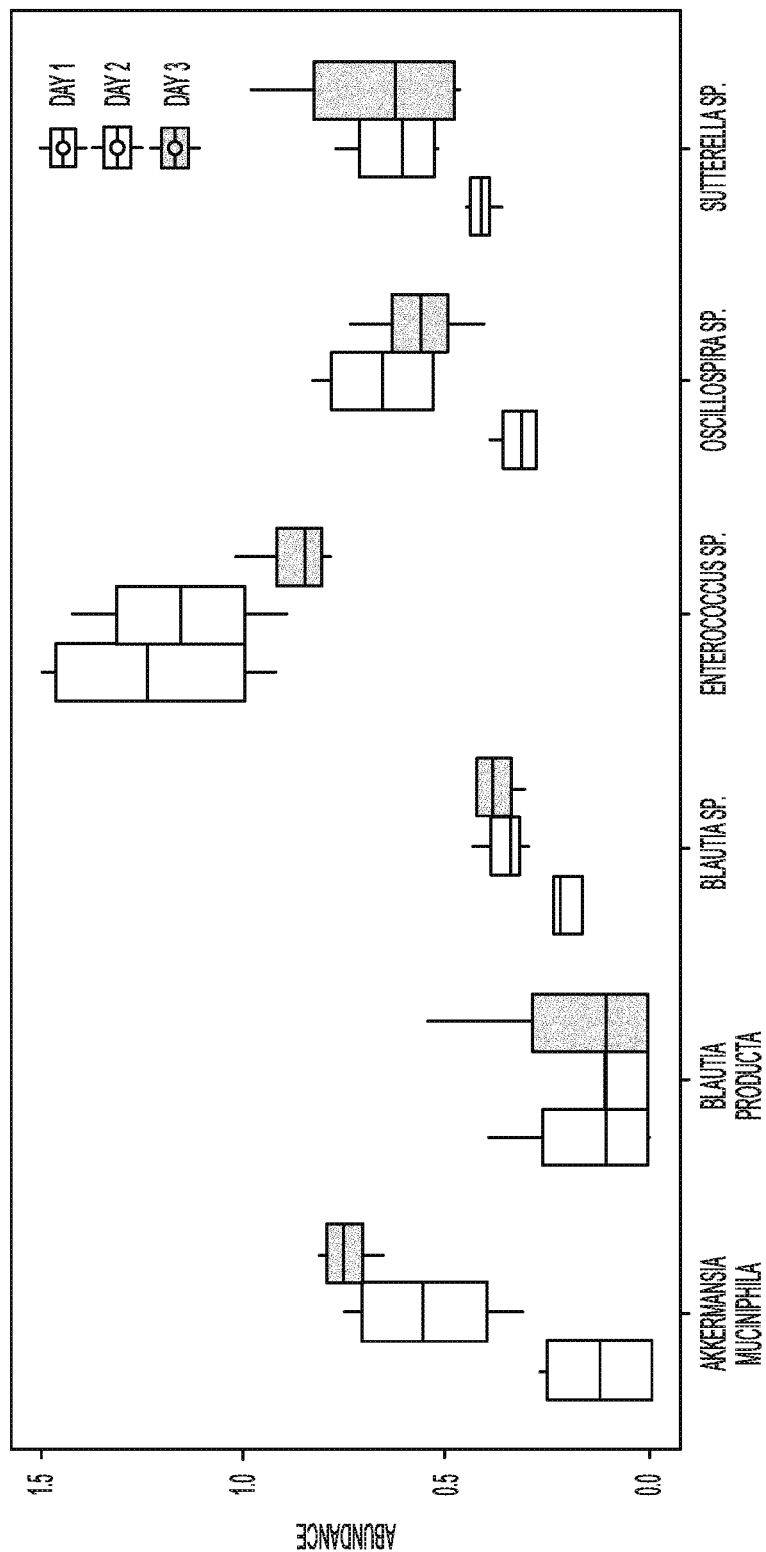
FIG. 4A is a graph showing genera growing or maintained in the anaerobic system over time.
Figure 4B:
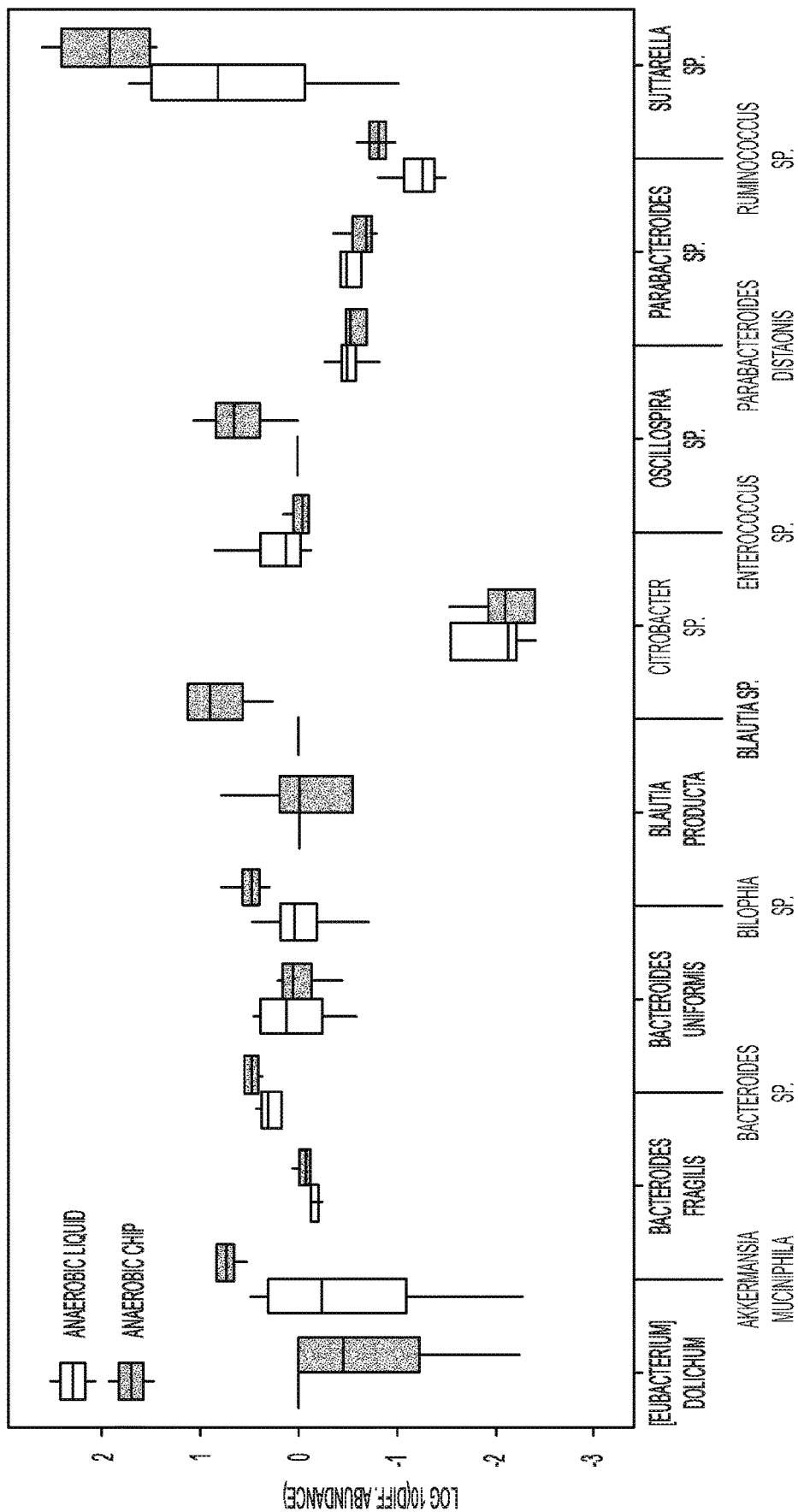
FIG. 4B is a graph showing a difference in abundance of bacteria in aerobic or anaerobic) when compared to a liquid culture, comparing growth at 3 days.
Figure 4C:
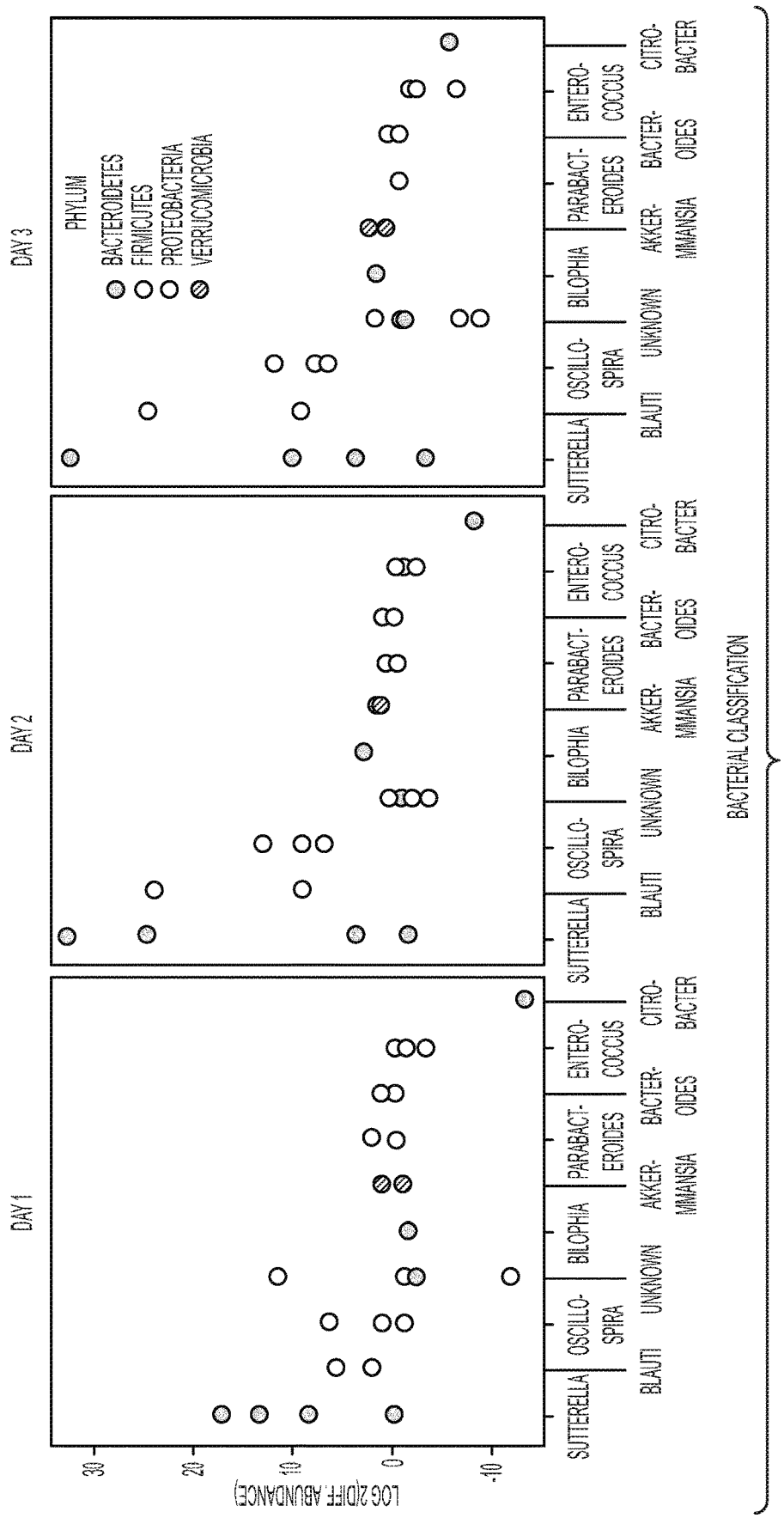
FIG. 4C is a graph showing a differential abundance in quantified genera across 3 days of co-culture.

Referring to FIGS. 4A-4C, representative graphs are generally directed to showing hypoxic Gut Chip-microbiome co-culture that enhances the growth of multiple genera compared to conventional liquid culture or aerobic chip system. FIG. 4A shows genera growing or maintained in the anaerobic system over time. FIG. 4B shows a difference in abundance of bacteria in aerobic or anaerobic) when compared to a liquid culture, comparing growth at 3 days. In FIG. 4C, which shows a differential abundance in quantified genera across 3 days of co-culture, the differential abundance was determined using DESeq2 comparing the anaerobic read counts with the aerobic ones (as disclosed in the methods of the present disclosure).

Figure 5B:
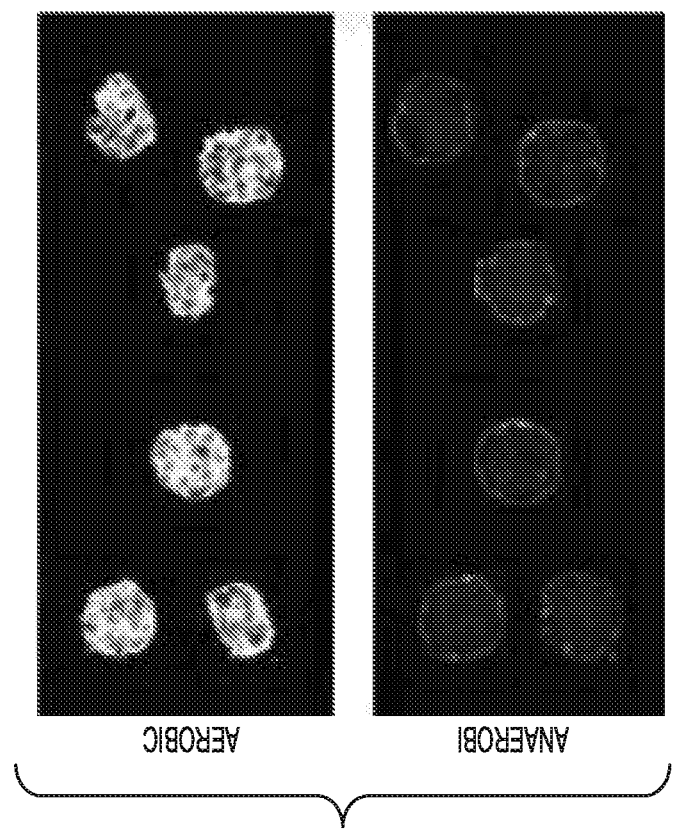
FIG. 5B is an image of the Gut Chip oxygen distribution in aerobic and anaerobic culture conditions.
Figure 5A:
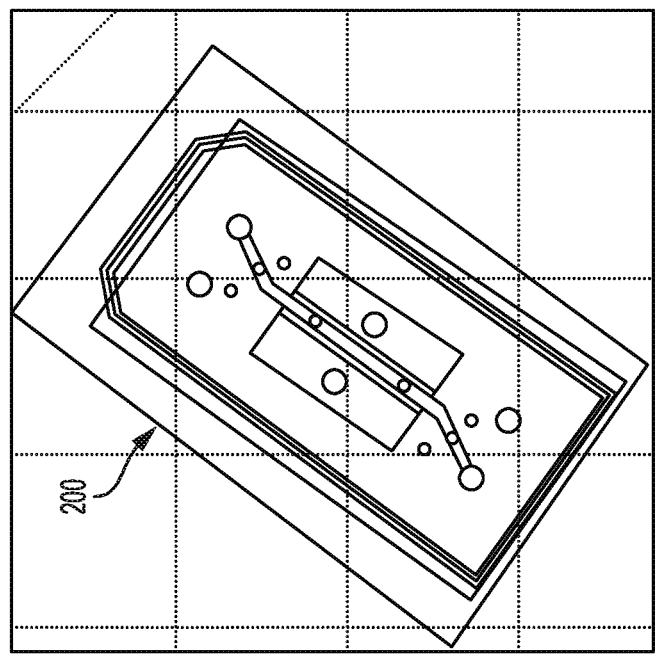
FIG. 5A is a representative optical image of an oxygen-sensing Gut Chip.
Figure 5C:
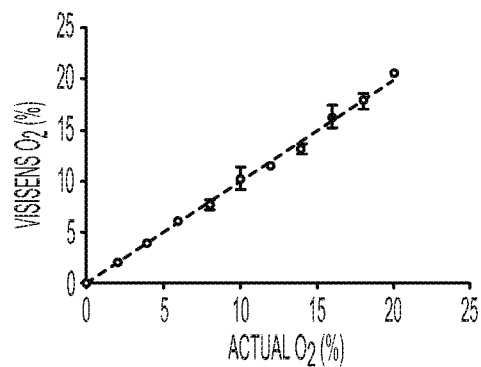
FIG. 5C is a graph showing an accuracy analysis of oxygen spots located in the Gut Chip in response to defined, standard oxygen concentrations.
Figure 5D:
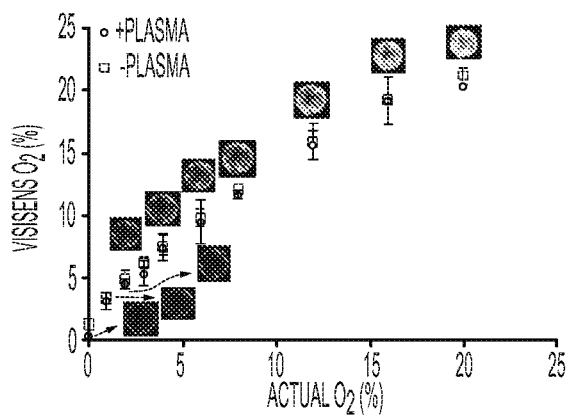
FIG. 5D is a graph representative of before and after plasma treatment.
Figure 5E:
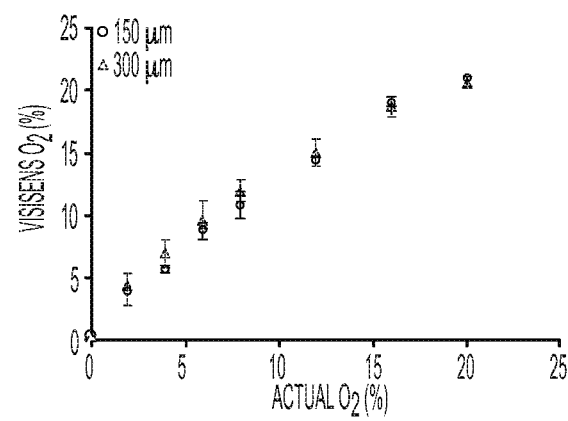
FIG. 5E is a graph showing an altered thickness (150 µm vs. µ300 m) of the spot.
Figure 5F:
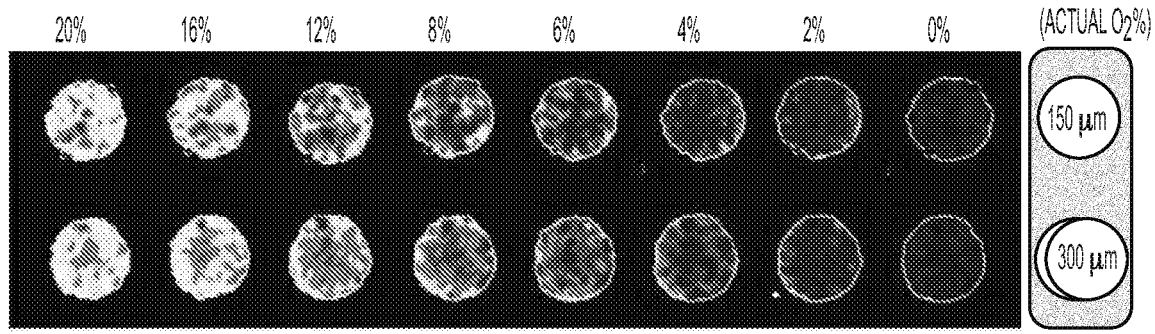
FIG. 5F shows representative images of the oxygen distribution from aerobic to anaerobic conditions.

Referring to FIGS. 5A-5F, images and graphs represent an oxygen-sensing Gut Chip 200. FIG. 5A shows the oxygen-sensing Gut Chip 200, and FIG. 5B shows the Gut Chip oxygen distribution in aerobic and anaerobic culture conditions. FIG. 5C shows an accuracy analysis of oxygen spots located in the Gut Chip 200 in response to defined, standard oxygen concentrations. FIG. 5D shows before and after plasma treatment of the Gut Chip 200. FIG. 5E shows an altered thickness (150 µm vs. 000 m) of the spot. FIG. 5F shows the oxygen distribution from aerobic to anaerobic conditions.

Figure 6A:
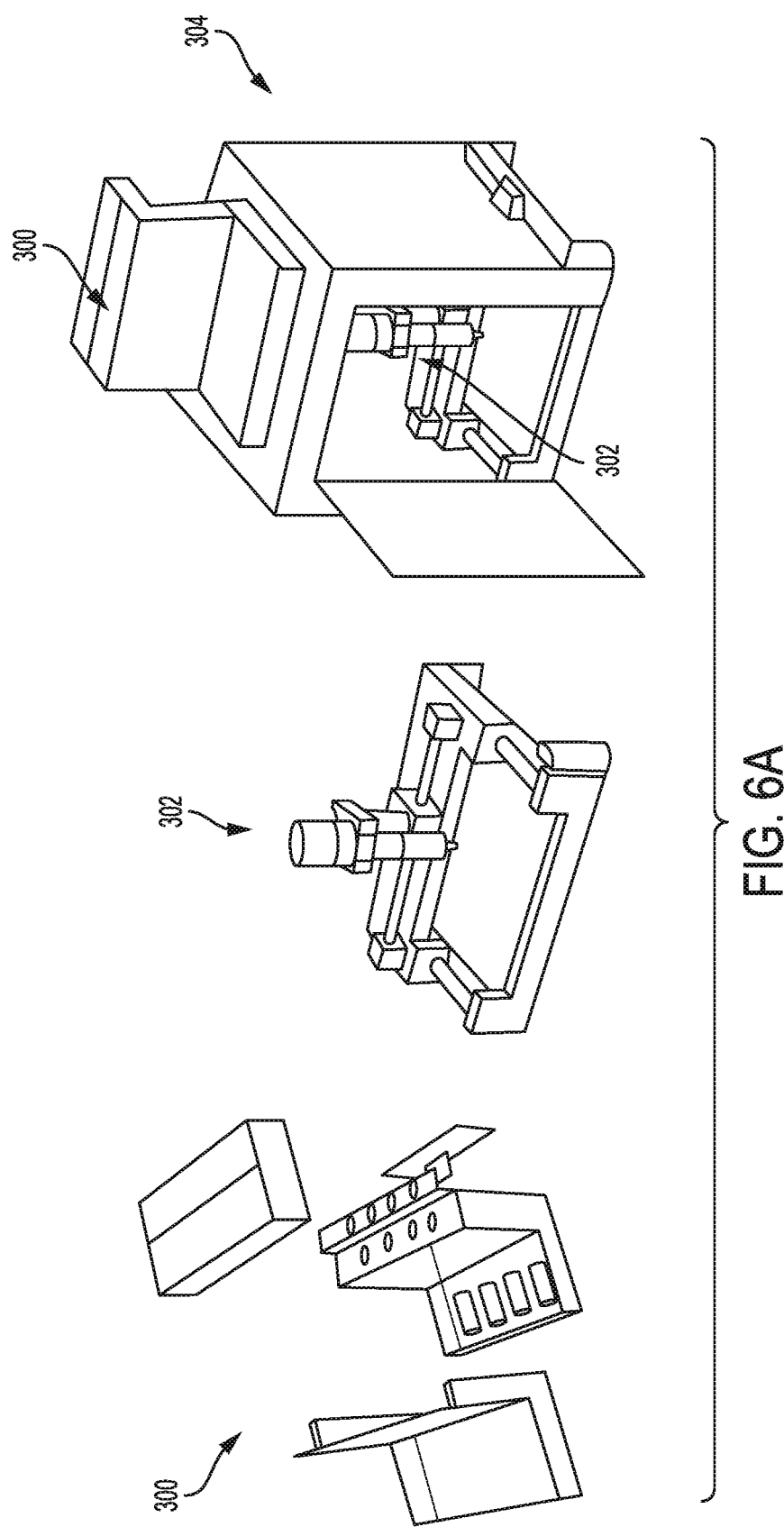
FIG. 6A is a schematic representation of a hypoxic chamber.
Figure 6B:
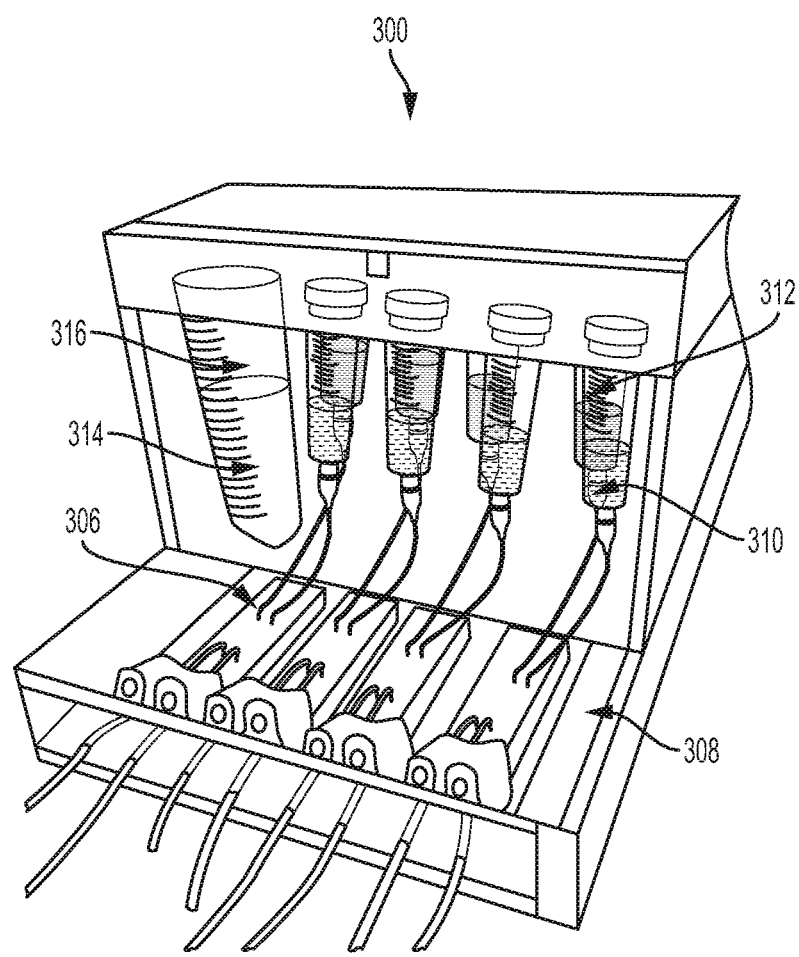
FIG. 6B is an image of the hypoxic chamber of FIG. 6A in use.

Referring to FIGS. 6A and 6B, representative images show a hypoxic chamber 300. In FIG. 6A, which is a schematic representation of a hypoxic chamber 300, a left image shows an exploded view of the hypoxic chamber 300, a middle image shows a linear positioning system 302 for indexed motions of the camera to any sensor spot along the chip or between the chips, and a right image shows rendering of a hypoxic farm 304 on imaging stand for monitoring of sensors without removing chips from hypoxic chamber 300. In FIG. 6B, which is an image of the hypoxic chamber 300 of FIG. 6A in use, chips 306 are placed in a hypoxic region 308 of the chamber 300 with media for the epithelium channel 310 (exposed to oxygen). Media reservoirs for the vascular channels 312 (inside the anaerobic chamber) are maintained at normoxia. The chamber 300 is purged with $N_2$ flow 314 through a bubbler 316.

Figure 7A:
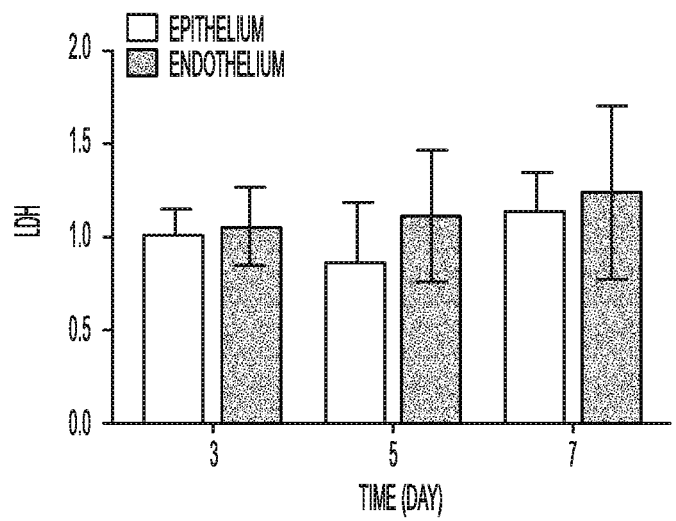
FIG. 7A is a graph showing effects on anaerobic culture of intestinal epithelium and vascular endothelium.
Figure 7B:
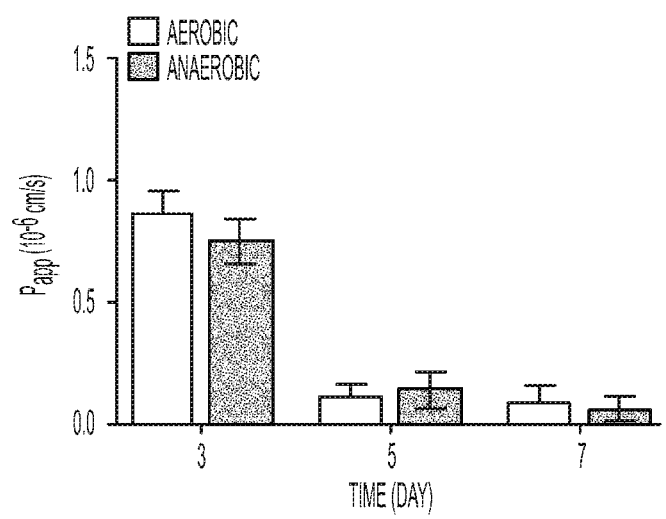
FIG. 7B is a graph showing changes in apparent paracellular permeability (Papp).

Referring to FIGS. 7A and 7B, graphs show effects on anaerobic culture and changes in apparent paracellular permeability. In FIG. 7A, effects on anaerobic culture of intestinal epithelium and vascular endothelium are assessed by quantifying LDH release from cells (data are presented as fold change in LDH levels relative to the aerobic control chips; n=4). In FIG. 7B, changes in apparent paracellular permeability (Papp) are measured by quantitating cascade blue transport across the tissue-tissue interface within the Gut Chip microdevices culture aerobically and anaerobically (n=4).

Figure 8A:
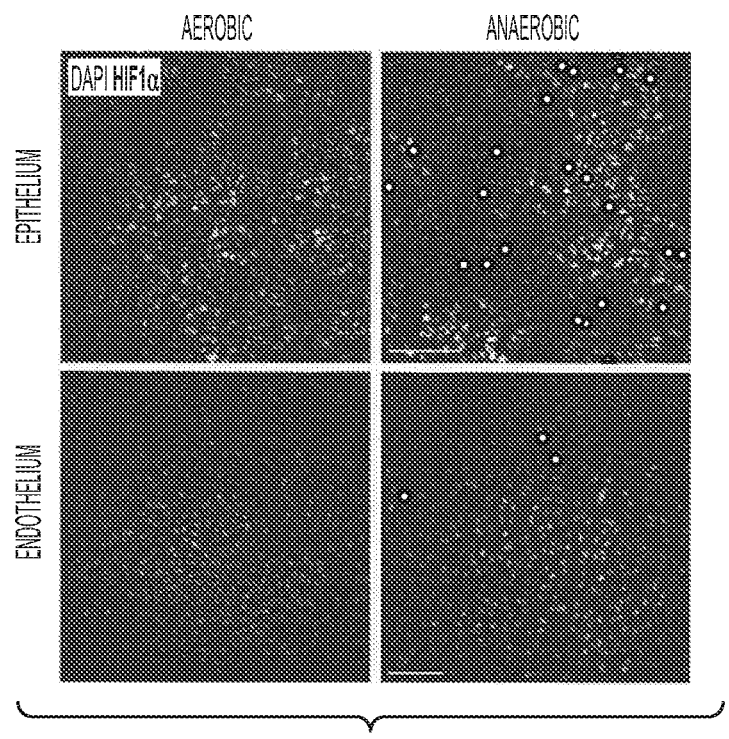
FIG. 8A shows representative images of immunofluorescence staining of nuclei.
Figure 8B:
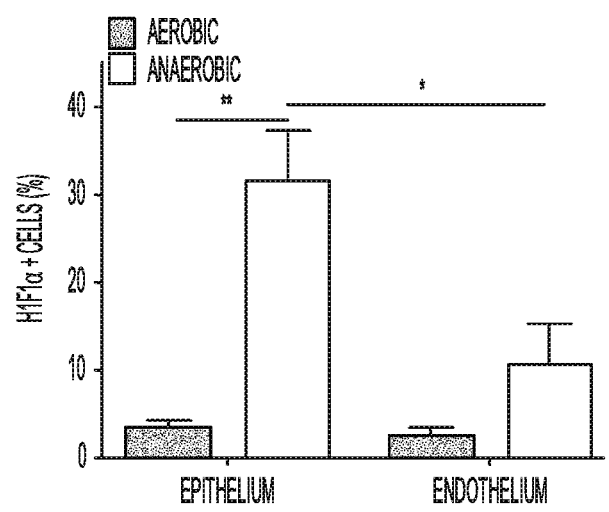
FIG. 8B is a graph showing the quantification of the percentage of epithelial and endothelial cells that expressed HIF1-α (HIF1-α$^+$ cells) after exposure to the conditions shown in a (n=3; *P<0.05, **P<0.01).

Referring to FIGS. 8A and 8B, representative images and a graph represent immunofluorescence staining of nuclei and a quantification of the percentage of epithelial and endothelial cells. In FIG. 8A, the staining of nuclei is with DAPI and HIF1-α in human intestinal epithelial cells and endothelial cells cultured aerobically and anaerobically (bar, 100 µm). In FIG. 8B, the graph shows the quantification of the percentage of epithelial and endothelial cells that expressed HIF1-α (HIF1-α$^+$ cells) after exposure to the conditions shown in a (n=3; *P<0.05, **P<0.01).

Figure 9B:
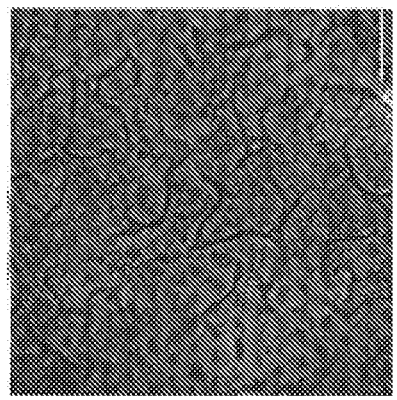
FIG. 9B shows representative immunofluorescence micrographs of HADA labeled *Bacteroides fragilis*.
Figure 9A:
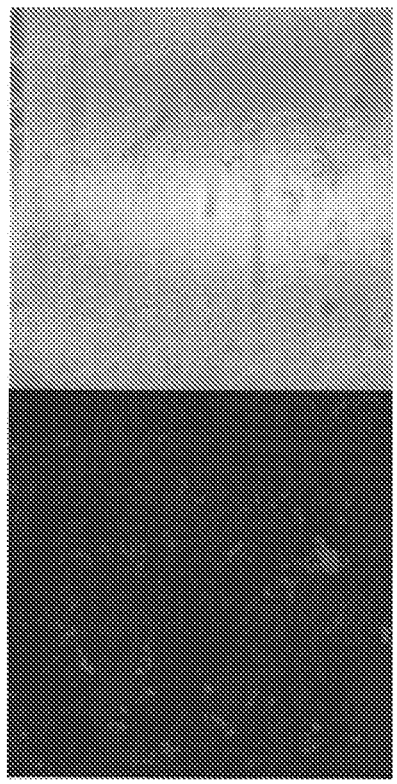
FIG. 9A shows a *fragilis* labeled with HADA.

Referring to FIGS. 9A and 9B, images show a *fragilis* labeled with HADA and representative immunofluorescence micrographs of HADA. In FIG. 9A, a corresponding brightfield image (right) represent the *fragilis* labeled with HADA before adding to chips. In FIG. 9B, the immunofluorescence micrographs show HADA labeled *Bacteorides fragilis* located on top of villus structures when viewed from above by phase contrast imaging (bar, 50 µm).

Figure 10A:
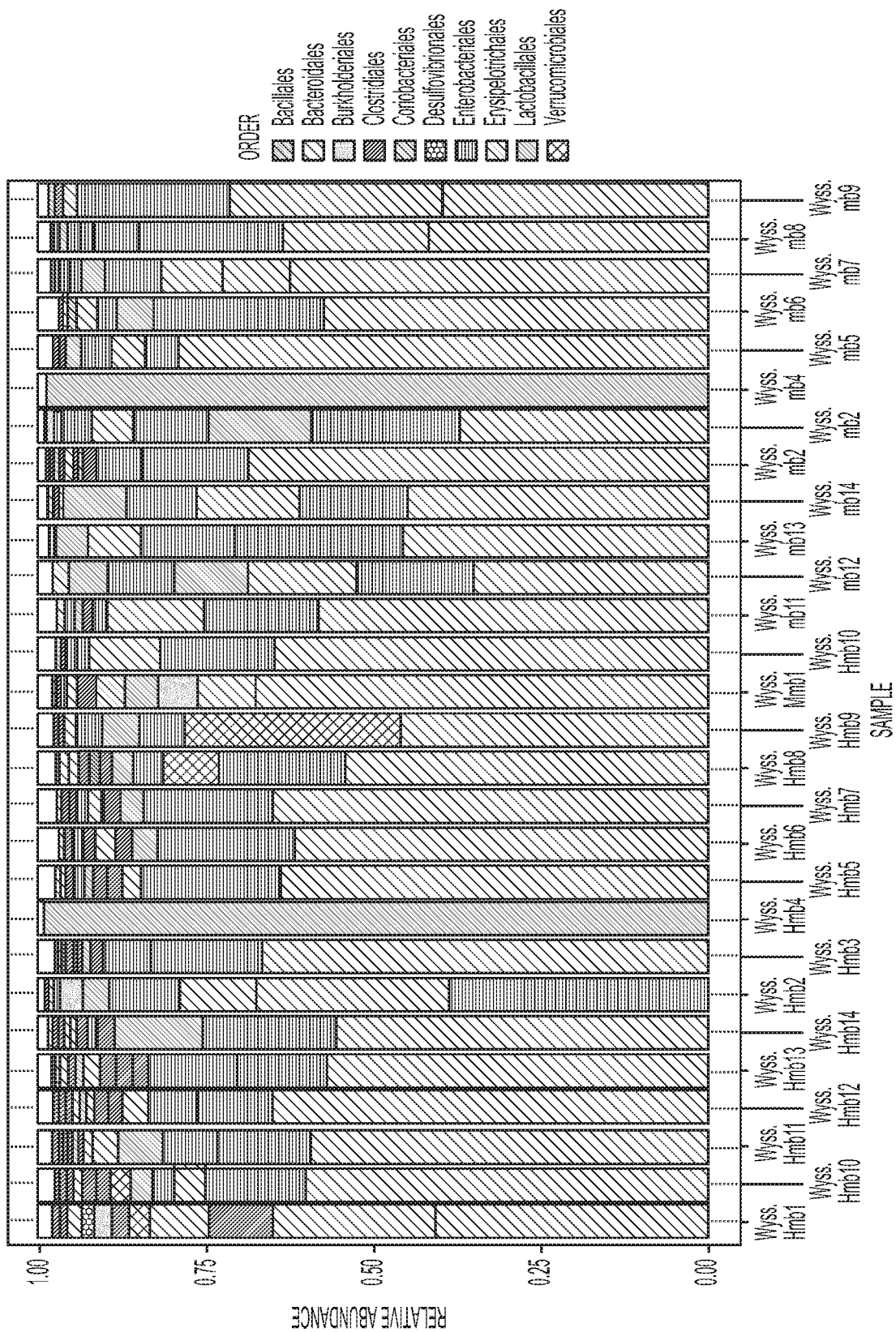
FIG. 10A is a graph showing Caco-2 viability.
Figure 10B:
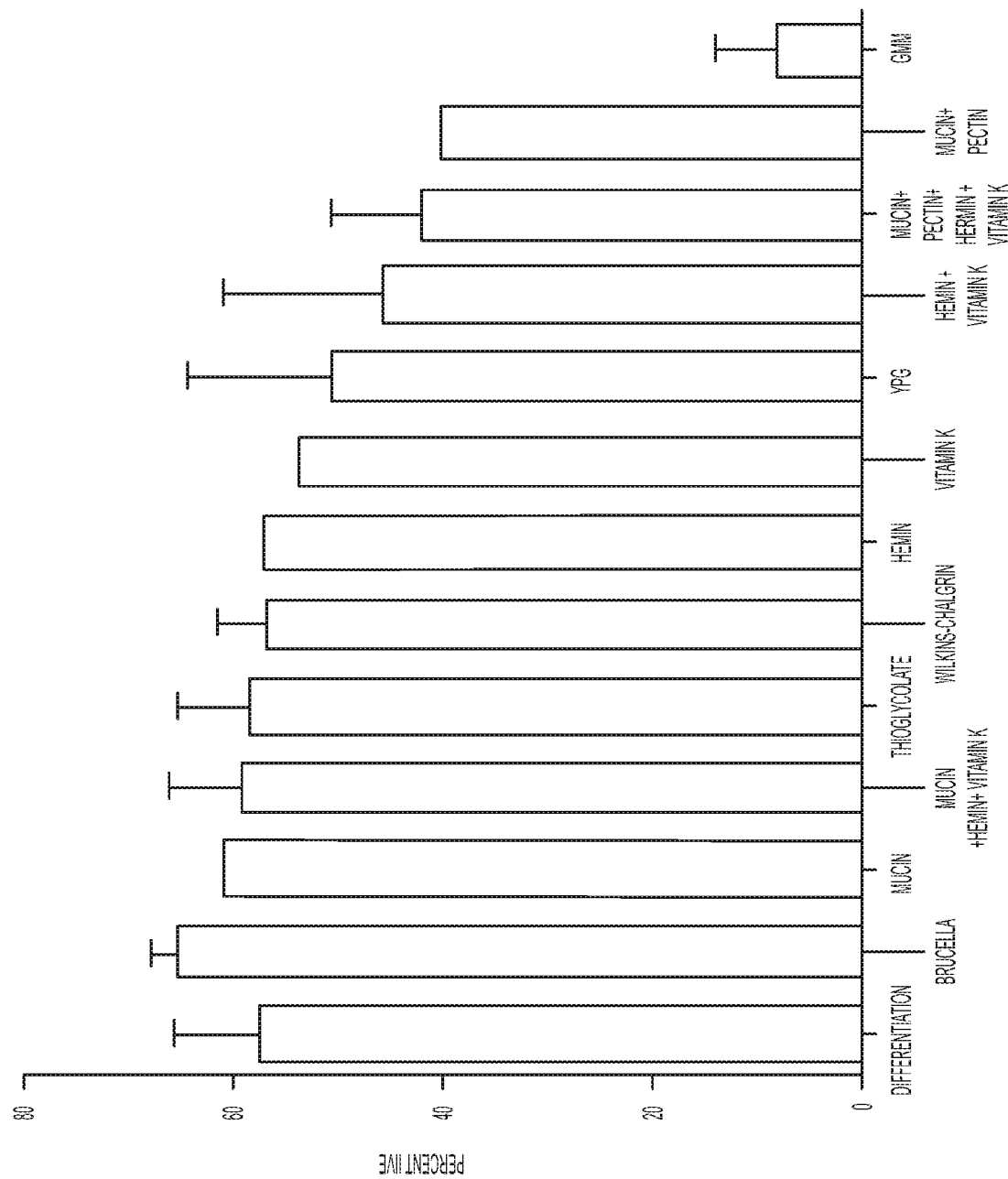
FIG. 10B is a graph showing changes in relative abundance of quantified microbial genera.

Referring to FIGS. 10A and 10B, graphs show Caco-2 viability and changes in relative abundance of quantified microbial genera. In FIG. 10A, Caco-2 viability is represented in 13 different types of media used for defining optimized microbiota growth. In FIG. 10B, the changes are representative of day 3 microbial cultures in cultured in 13 defined media composition. Relative abundance is determined per sample per day as (genus read counts)/(total read counts).

Figure 10C:
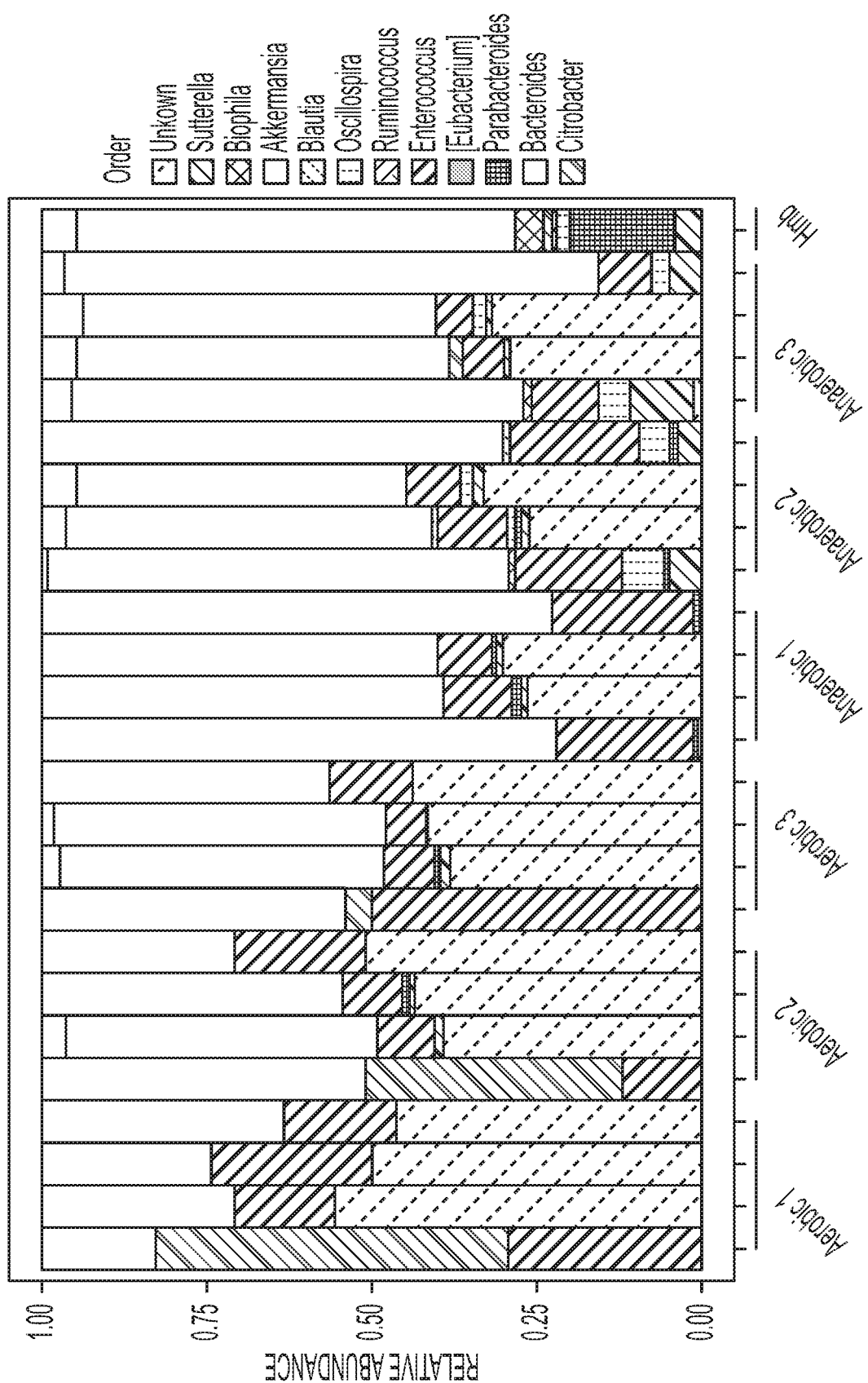
FIG. 10C is a graph showing genera abundance in a human microbiome stock.

Referring to FIG. 10C, a graph shows genera abundance in an originally human microbiome stock derived from gnotobiotic mice (HMB) at time 0. The general abundance is significantly different than what grew out of the human microbiome stock derived from the gnotobiotic mice. The graph is further representative of an analysis of the diversity and relative abundance of microbiota co-cultured in intestine chips under aerobic and aerobic conditions. Relative abundance of genera measured across all samples highlights changes in the abundance of the different genera observed over time, with data points representing each of three replicate chips cultured under aerobic or anaerobic conditions at 0, 1, 2 or 3 days of culture (left to right, respectively) in direct contact with human Caco2 intestinal epithelium. Hmb indicates genera abundance in the complex microbiome stock derived from gnotobiotic mice at time 0.

Although the observed diversity and Shannon Index are lower than what is observed in human stool samples, the graph shows an increase in richness that is observed compared to a starting inoculum (human biome cultured in mice) over the course of the three-day experiment. More specifically, 11 well-characterized genera are identified, including *Eubacterium, Oscillospira, Blautia, Sutterella, Biophila, Akkermansia, Ruminococcus, Bacteroides, Parabacteroides, Enterococcus* and *Citrobacter*, with an additional 8 OTUs of unknown genera from Firmicutes (5 OTUs) and Proteobacteria (3 OTUs) phyla, that are present in the chips. An observed features indicates that some gut microbial species may grow better under conditions that more closely mimic regions of the living intestine than in stool. A further beneficial, important feature is that unknown genera were present when the microbiome derived from stool was cultured on the microfluidic devices. This beneficial features indicates that this platform can permit the growth of species/genera that other culture systems cannot.

Figure 10D:
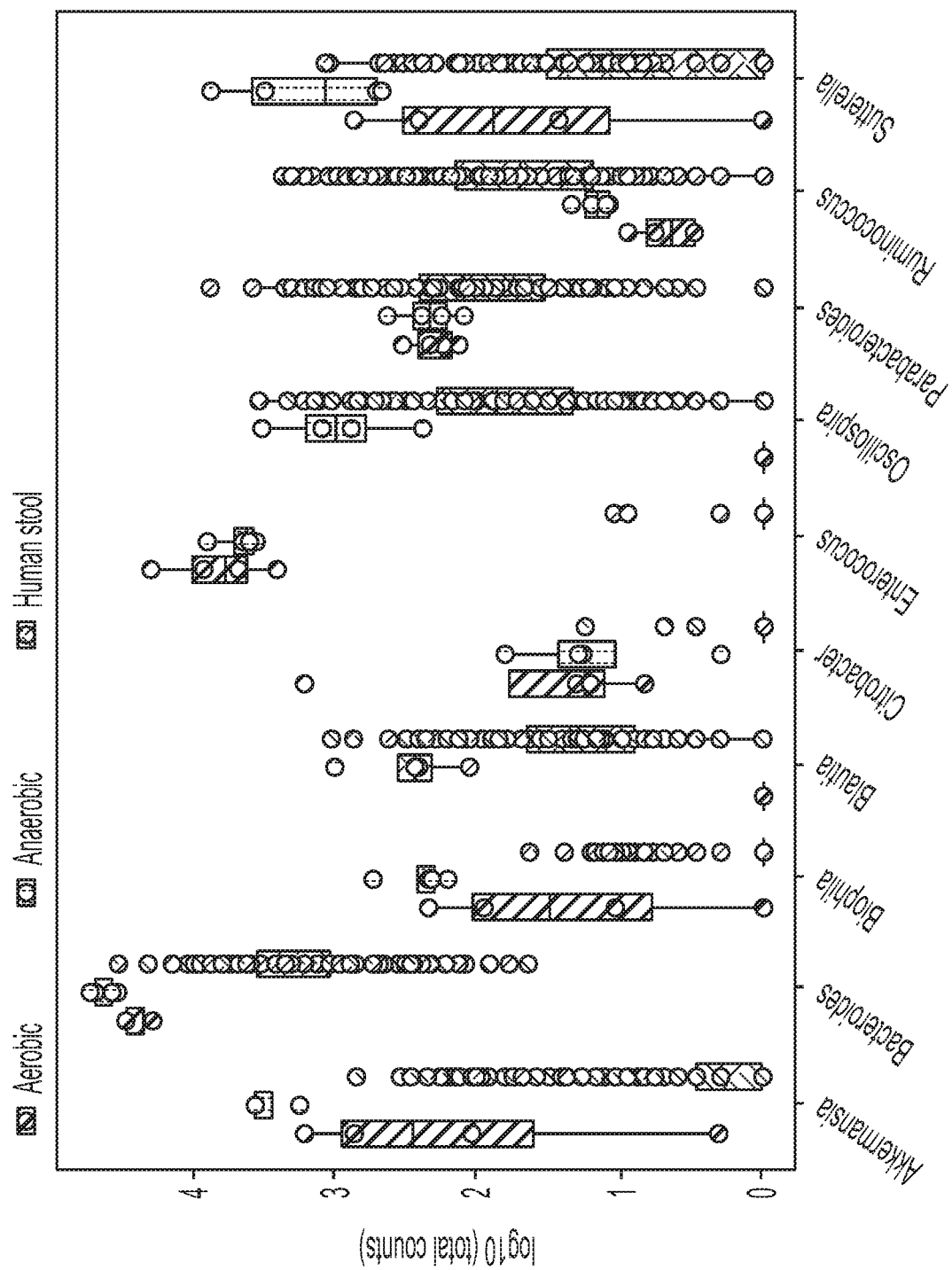
FIG. 10D is a graph showing a comparison between identified genera and publicly available data.

Referring to FIG. 10D, a graph represents a further assessment of the physiological mimicry obtained using the anaerobic intestine chip lined by Caco2 epithelium. Specifically, the genera identified in this particular study was compared with publicly available data from studies of human stool generated by the Human Microbiome Project 34. It was not initially expected that the composition of the microbiome grown on chip would precisely recapitulate that of stool because the microbiome of the small intestine is known to show regional differences. Nevertheless, the results show that the anaerobic culture system provides an environment for complex gut microbiota that sustains a diverse bacterial community, which falls into the range of abundances reported in the Human Microbiome Project. Furthermore, the relative abundances of the phyla that dominate the human gut, Bacteroidetes (Bacteroidetes and Parabacteroides genera) and Firmicutes (*Blautia, Enterococcus, Ruminococcus*, and *Oscillospira* genera), were higher in the anaerobic chips than in the aerobic chips with some genera (*Blautia* and *Oscillospira*) missing in the aerobic chips altogether.

Oxygen sensor readouts in aerobic and anaerobic chips cultured with a viable microbiome or sterilely (microbe-free) confirmed that the oxygen concentration was maintained below 1% throughout 5-day co-culture period in anaerobic co-cultures. Moreover, these results showed a decrease in oxygen concentration in aerobic chips cultured with microbiome over time, which is similar to what we observed in the co-culture with *B. fragilis*. This was likely due to the increased vertical growth of villi observed in these chips relative to anaerobic chips, as well as to concomitant oxygen utilization by the bacteria, which increased in numbers by day 1 in both aerobic and anaerobic chips.

Although the oxygen concentration in the aerobic chip never reached the low levels obtained in anaerobic chips, this decrease in oxygen likely explains the presence of some obligate anaerobes, such as *Akkermansia*, that is observed in the aerobic chips. This is surprising because mammalian cells require oxygen while strict anaerobes find it toxic. However, it is a unique feature of the disclosed system that the system components regulate oxygen to support this co-culture. In particular, and without being bound by theory, the mammalian cells consume oxygen that is predominantly delivered to them from their basal side to reduce the concentration on the anaerobes. In addition, and without being bound by theory, other elements of the complex microbiome, for example aerobes present, also consume remaining oxygen that may otherwise poison the anaerobes. This is an exciting capability of the disclosed system because it allows the study of the interaction of anaerobes with the mammalian tissue.

Interestingly, the genus *Akkermansia*, which has been recently implicated as an enhancer of gut barrier function, shows a considerably higher number of total counts in the anaerobic culture system compared to human stool. Additionally, the genus *Enterococcus* is found to be present at higher levels in both chip culture systems compared to the stool samples, suggesting that some gut microbial species may grow better under conditions that more closely mimic regions of the living intestine than in stool. Taken together, this data confirms that this anaerobic human intestine chip system enables living human intestinal epithelium to be co-cultured in the same channel as a complex human gut microbiome containing a range of bacterial genera that come much closer to what is observed in healthy human donors than has ever been possible before.

Figure 11:
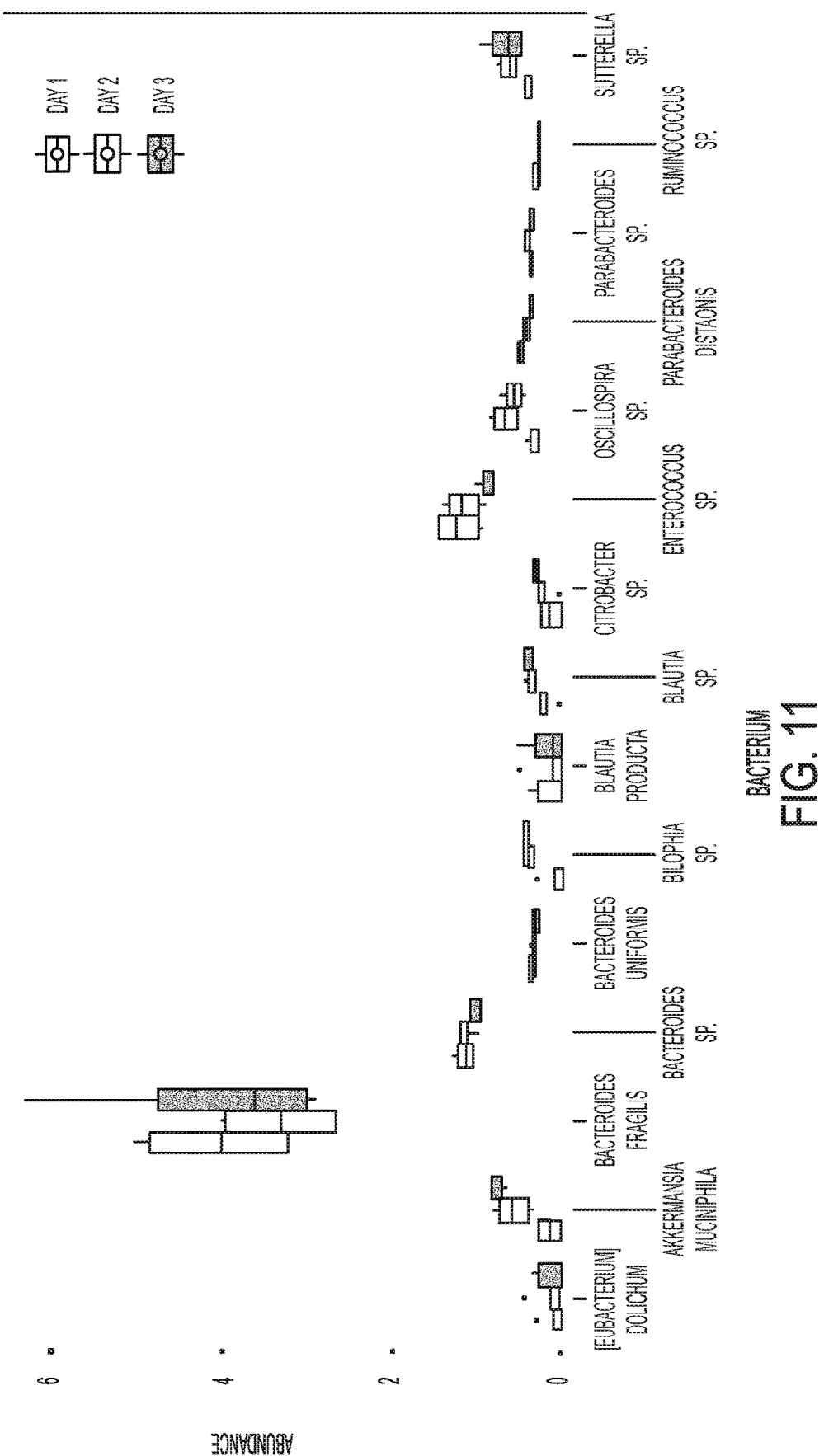
FIG. 11 is a graph showing Genera growing or maintained in the anaerobic chip over time.

Referring to FIG. 11, a graph shows data representative of genera growing or maintained in the anaerobic chip over time.

Referring to FIG. 12, results show media tested for microbial diversity.

Figure 13:
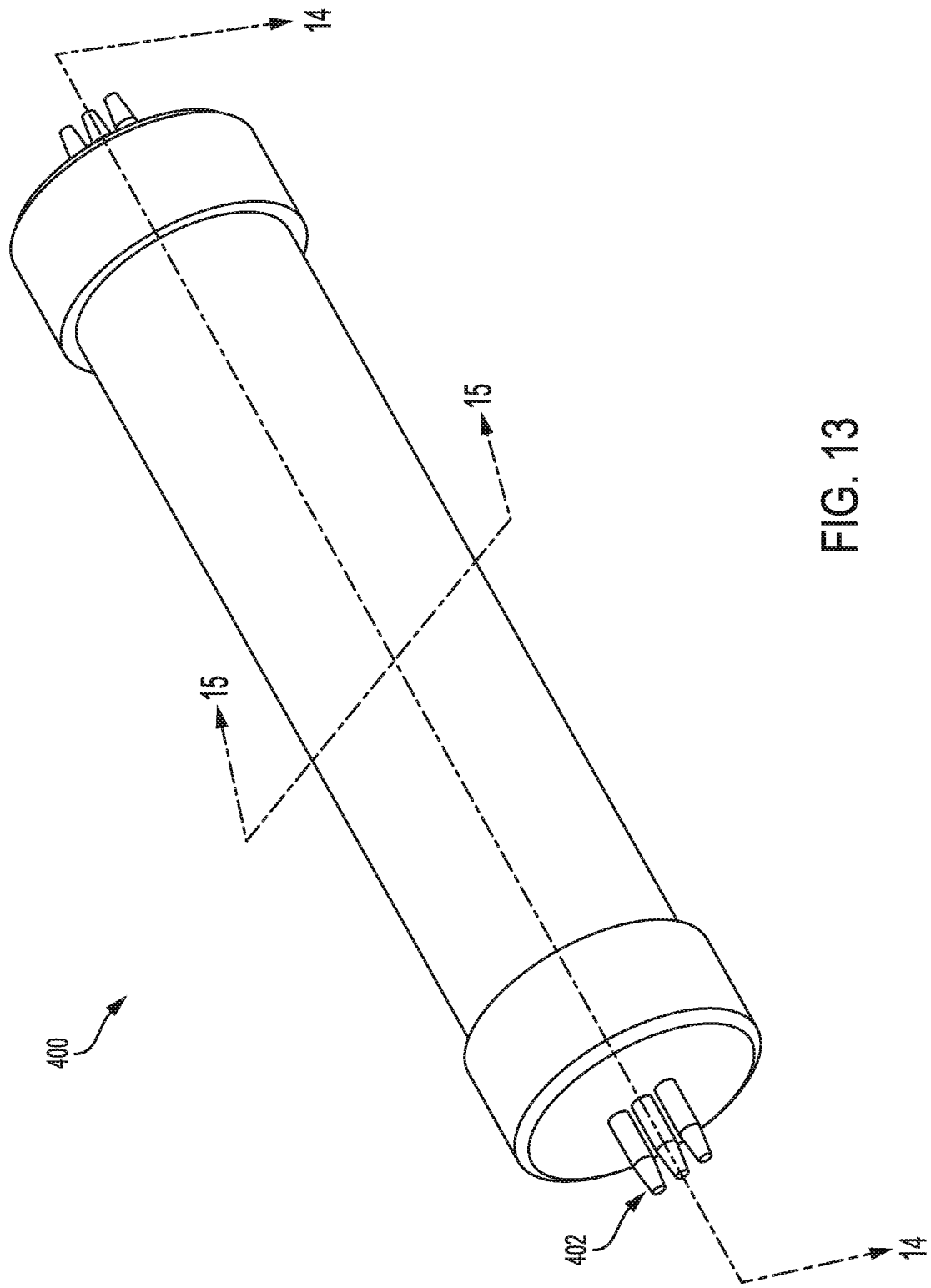
FIG. 13 is a perspective view of a bioreactor with an oxygen gradient configuration.
Figure 14:
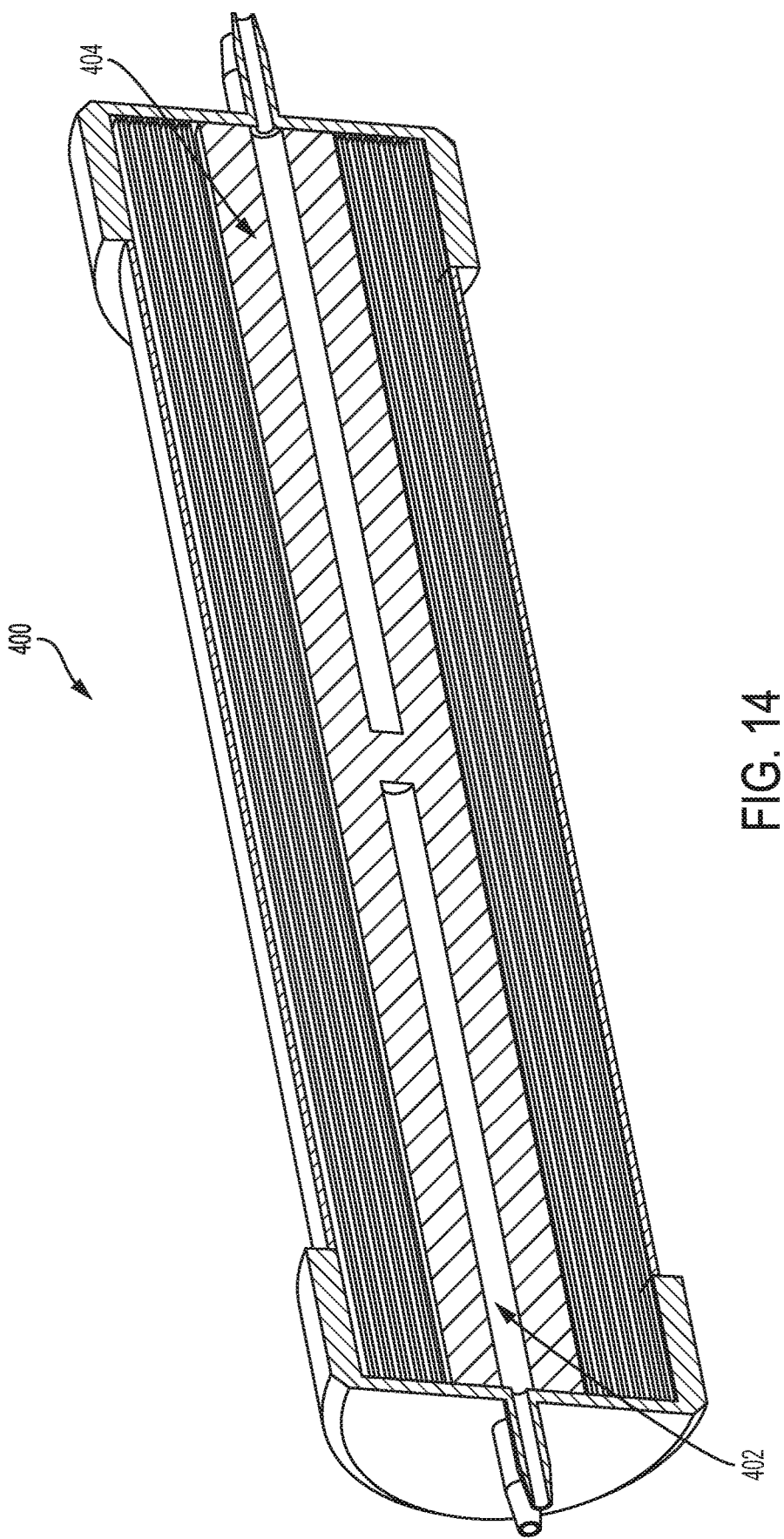
FIG. 14 is a longitudinal cross-sectional view along cross-sectional lines "14-14" of the bioreactor of FIG. 13.
Figure 15:
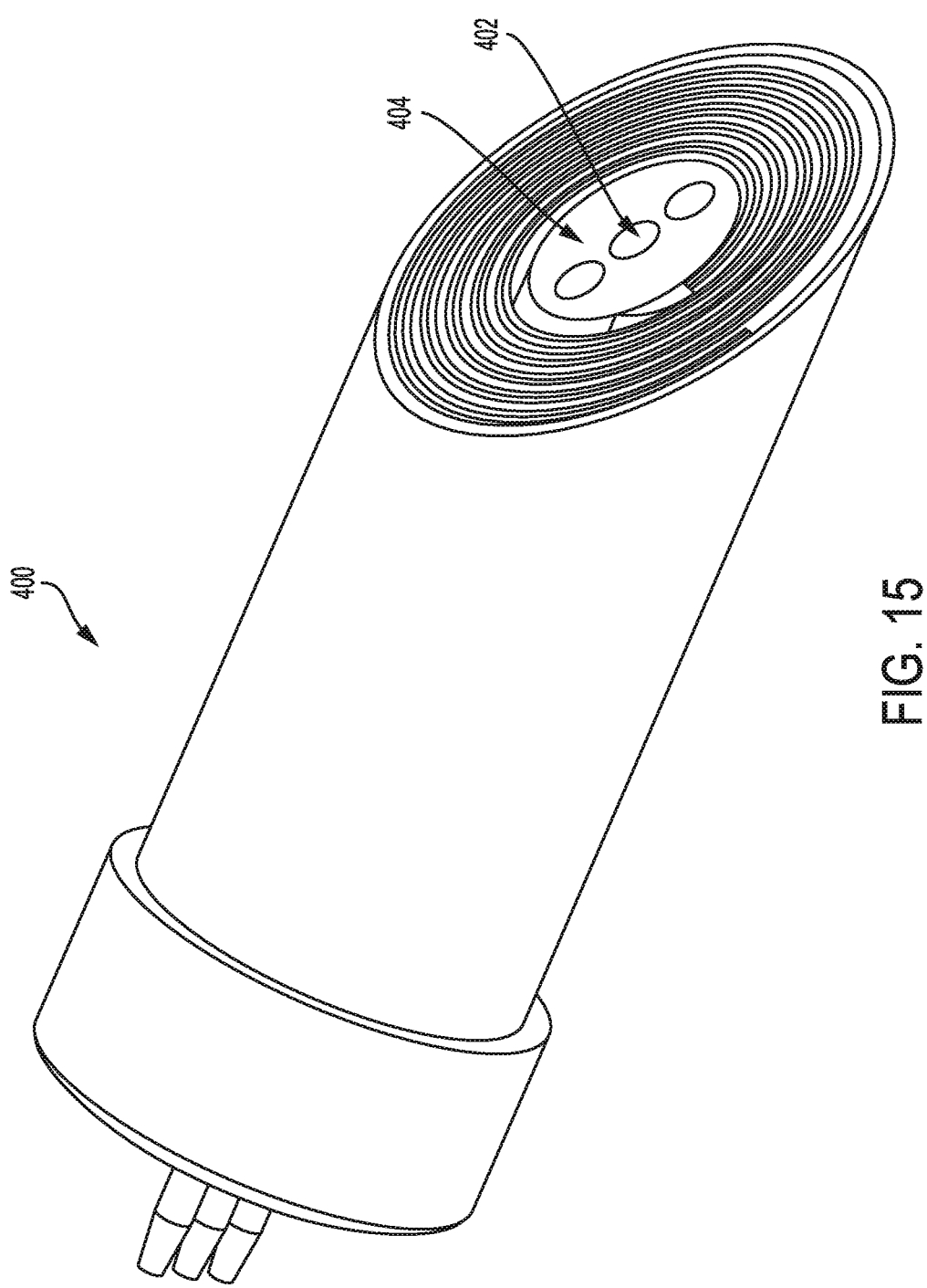
FIG. 15 is a lateral cross-sectional view along cross-sectional lines "15-15" of the bioreactor of FIG. 13.

Referring to FIGS. 13-15, a bioreactor 400 shows a configuration in which an oxygen gradient approach is applied to a non-organ chip design. The bioreactor includes three fluidic channels 402 that are wound around a core 404, with gas permeability properties of each layer being configured to permit or block oxygen diffusion. The fluidic channels 402 contain gas or liquid. According to other example, the bioreactor 400 is any other reactor configured with the oxygen gradient design described in the present disclosure.

Referring to FIGS. 16A-16D, images and data show culture aspects for primary human ileum chips. FIG. 16A shows the DIC microscopic image of the primary human ileum chips. FIG. 16B shows the confocal fluorescence microscopic image of the primary human ileum chips. FIG. 16C shows a graph illustrating the co-culture stably maintained five days on-chip. FIG. 16D shows a table with observed richness of various ileum samples.

Figure 17A:
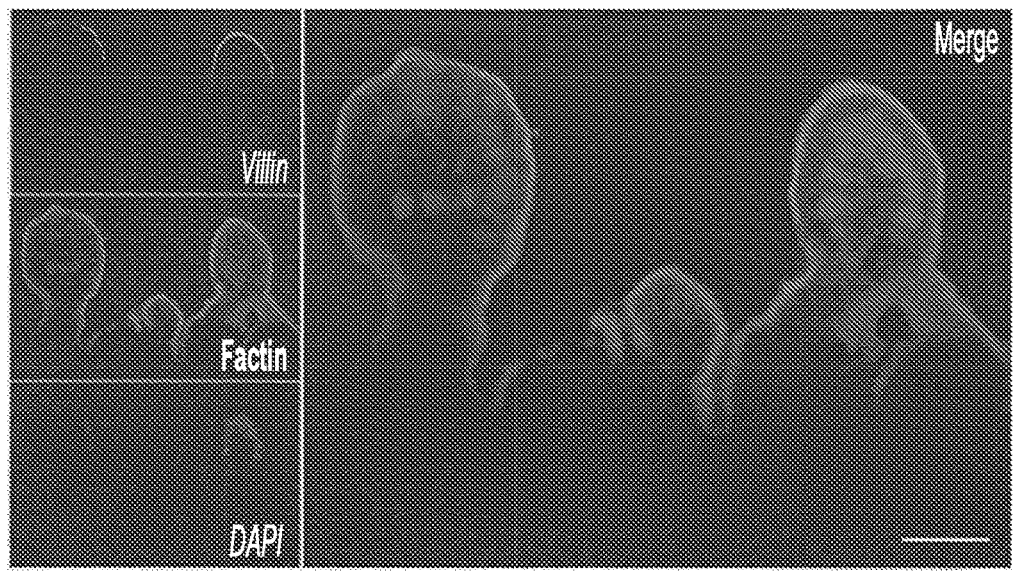
FIG. 17A shows confocal fluorescence microscopic images with villus morphology of a primary ileal epithelium stained for villin, F-actin and DAPI.
Figure 17B:
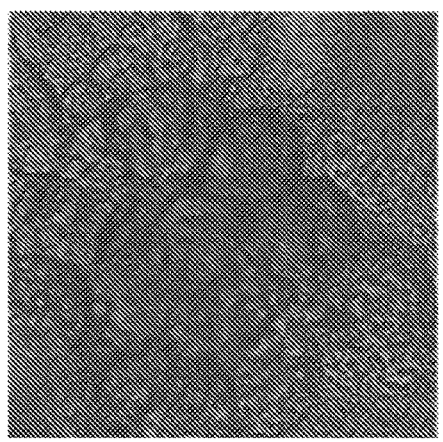
FIG. 17B shows an image of secreted mucus with alcian blue staining.
Figure 17C:
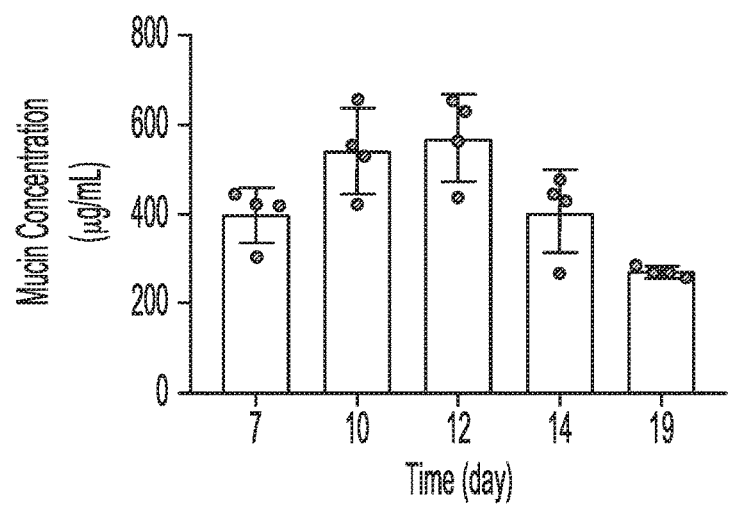
FIG. 17C is a graph with quantitation of alcian blue staining in cultures shown in FIG. 17B.

Referring to FIGS. 17A-17C, villus morphology is illustrated. Specifically, FIG. 17A shows confocal fluorescence microscopic views illustrating the villus morphology of the primary ileal epithelium stained for villin (cyan), F-actin (magenta), and DAPI (blue (bar, 50 µm). FIG. 17B shows phase contrast views of ileum chips stained with alcian blue. FIG. 17C shows quantitation of alcian blue staining in cultures shown in FIG. 17B.

Figure 18A:
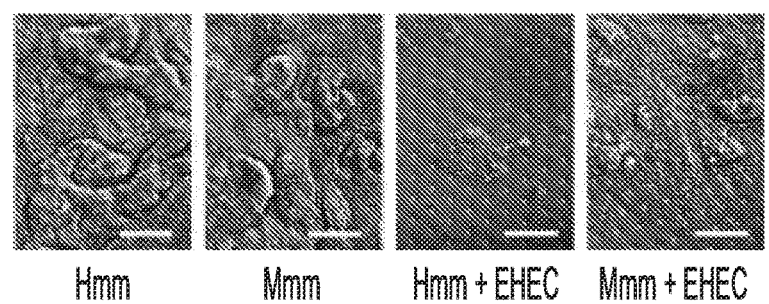
FIG. 18A shows images of differential interference contrast of colonic epithelium.
Figure 18B:
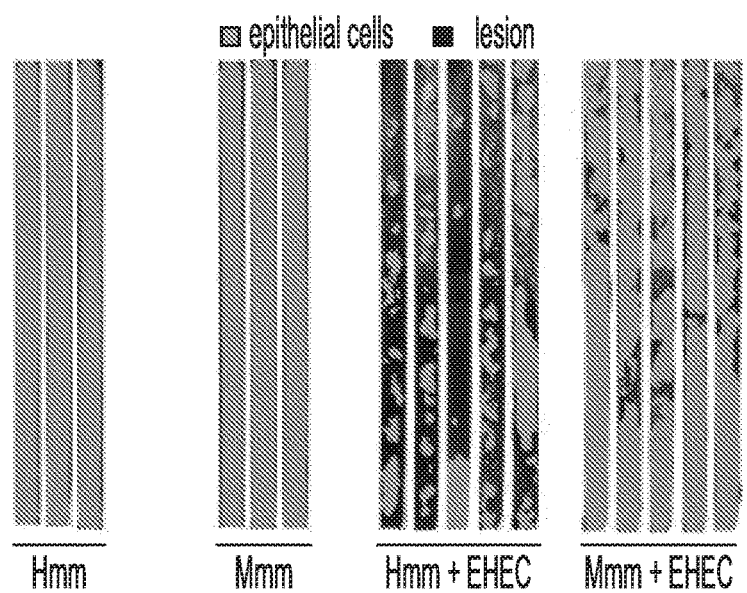
FIG. 18B shows images of an entire colon epithelium.
Figure 18C:
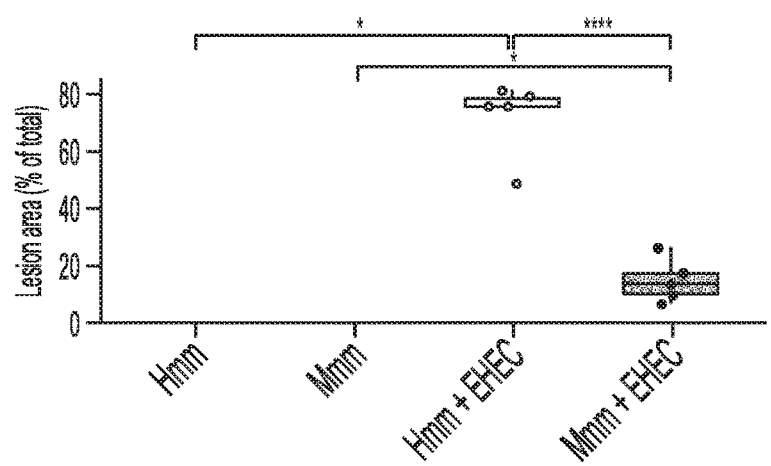
FIG. 18C shows graphs representative of quantification of epithelial lesion areas.

Referring generally to FIGS. 18A-18C, microbiome metabolites recapitulate species-specific tolerance in Colon Chips. Human or mouse intestinal microbiome metabolites (e.g., isolated from specific strains of bacterial or fecal samples incubated in a bioreactor) were added to the intestinal channel of optically clear, human colon chips that are lined by primary human colon epithelial cells and directly opposed to a second parallel vascular microchannel in which HIMVECs are cultured. The two channels are separated by a thin, porous, ECM-coated membrane. Human intestinal epithelium was isolated from resections or endoscopic tissue biopsies. Endoscopic biopsies were collected from macroscopicallynormal (grossly unaffected) areas of the colon undergoing endoscopy for abdominal complaints. Organoids were grown from these tissue samples and seeded into the upper chamber of a two channel closed top microfluidic device. Human intestinal microvascular endothelial cells (HIMECs) were obtained from ScienCell (Cat #2900). The intestinal luminal channel medium was switched to 5% (vol vol-1) human (Hmm) or mouse (Mmm) gut microbiome metabolites isolated from PolyFermS bioreactors, diluted in phosphate-buffered saline (PBS) containing calcium and magnesium (final osmolarity=300 mOsm kg-1), filtered through a 0.2 µm filter (Corning), and stored at −80° C.

Further referring generally to FIGS. 18A-18D, an analysis of EHEC-induced epithelial injury on-chip is shown. Referring specifically to FIG. 18A, representative differential interference contrast (DIC) images show the colonic epithelium in the presence of Hmm or Mmm in the presence or absence of EHEC (bar, 100 µm). Referring specifically to FIG. 18B, pseudo-colored images show the entire colon epithelium within the upper channel of the colon chip (yellow or bright region) cultured in the presence of Hmm or Mmm with or without EHEC (dark regions indicate lesion areas).

Figure 18D:
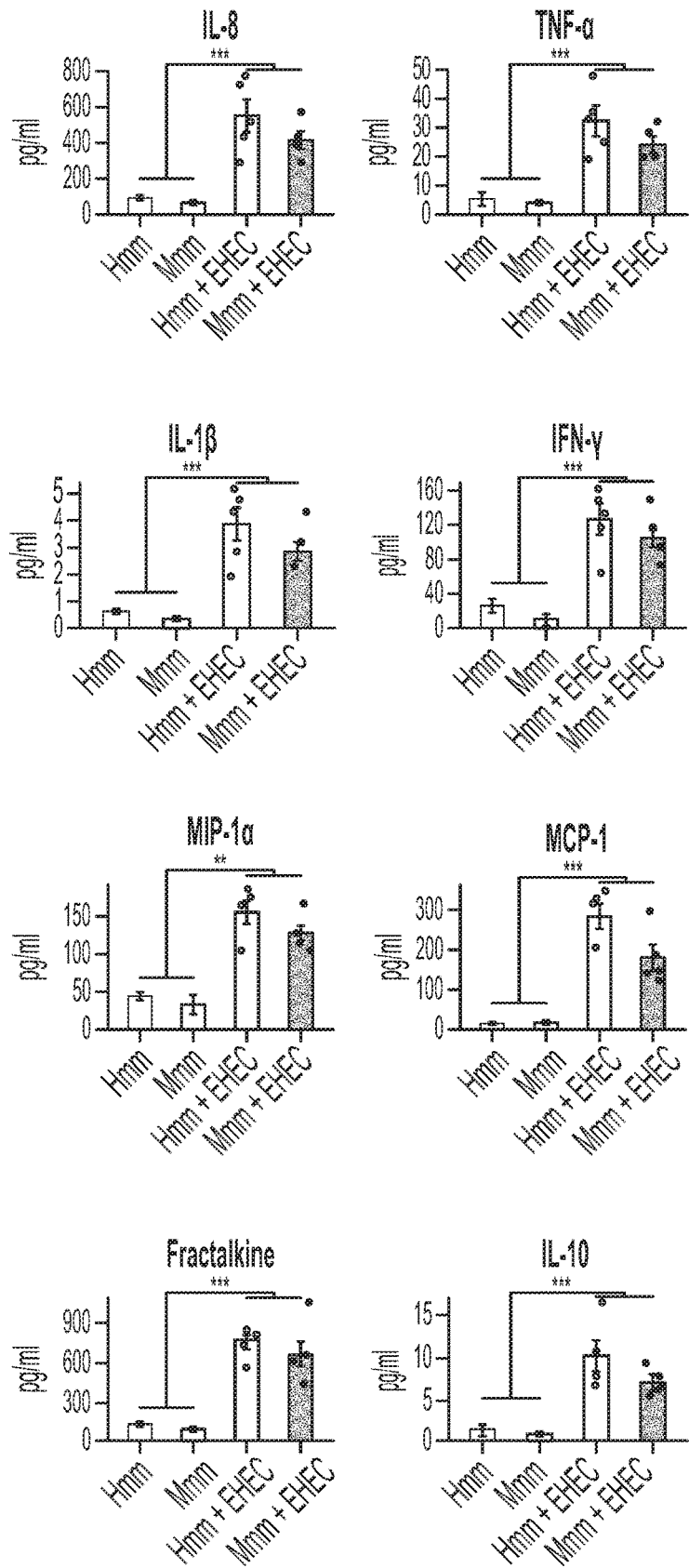
FIG. 18D shows graphs representative of changes in levels of various indicated cytokines released into a vascular channel of colon chips.

Referring specifically to FIG. 18C, quantification of epithelial lesion areas is represented based on the experimental conditions of FIGS. 18B and 18C. Epithelial lesion defined as regions in which cells normally contained within a continuous intact epithelium have fully detached from the ECM-coated membrane and their neighboring cells, thus, leaving exposed regions of the membrane below. Referring specifically to FIG. 18D, changes in levels of various indicated cytokines are released into the vascular channel of the colon chips by cells cultured under the conditions described in FIGS. 18B and 18C (*$p<0.05$; $p<0.01$; *$p<0.001$; ****$p<0.0001$).

Figure 19A:
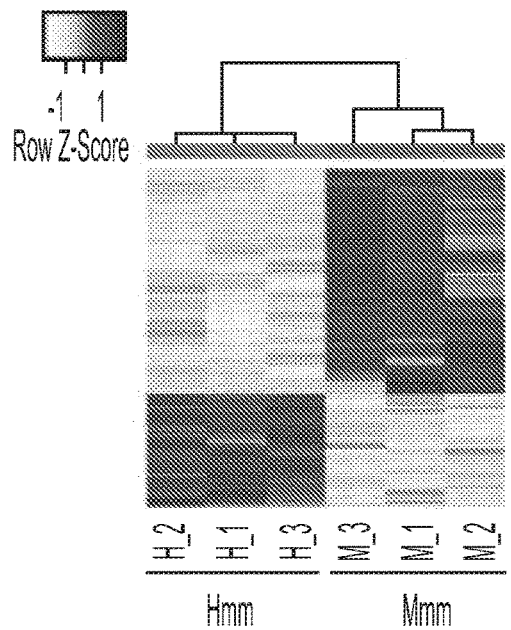
FIG. 19A shows an image of a heat-map of differentially expressed genes.
Figure 19B:
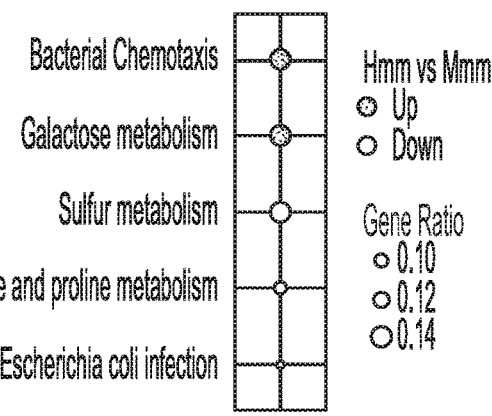
FIG. 19B shows a representative image of a gene enrichment analysis

Referring generally to FIGS. 19A-19I, human microbiome metabolites stimulate bacterial motility. Referring generally to FIGS. 19A-19D, changes in the EHEC transcriptome are induced by exposure to human (Hmm) versus mouse (Mmm) gut microbiome metabolites. Referring specifically to FIG. 19A, a heat-map of differentially expressed genes (red or brighter area indicates higher levels of expression). Referring specifically to FIG. 19B, a gene enrichment analysis is presented.

Figure 19C:
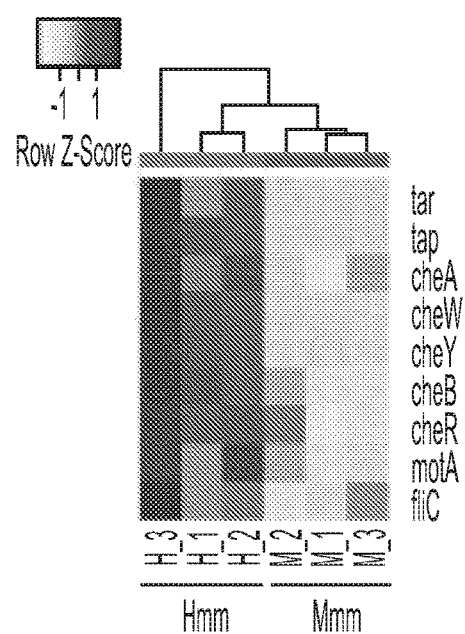
FIG. 19C shows an image of a heat-map of chemotaxis and flagellar assembly pathways.
Figure 19D:
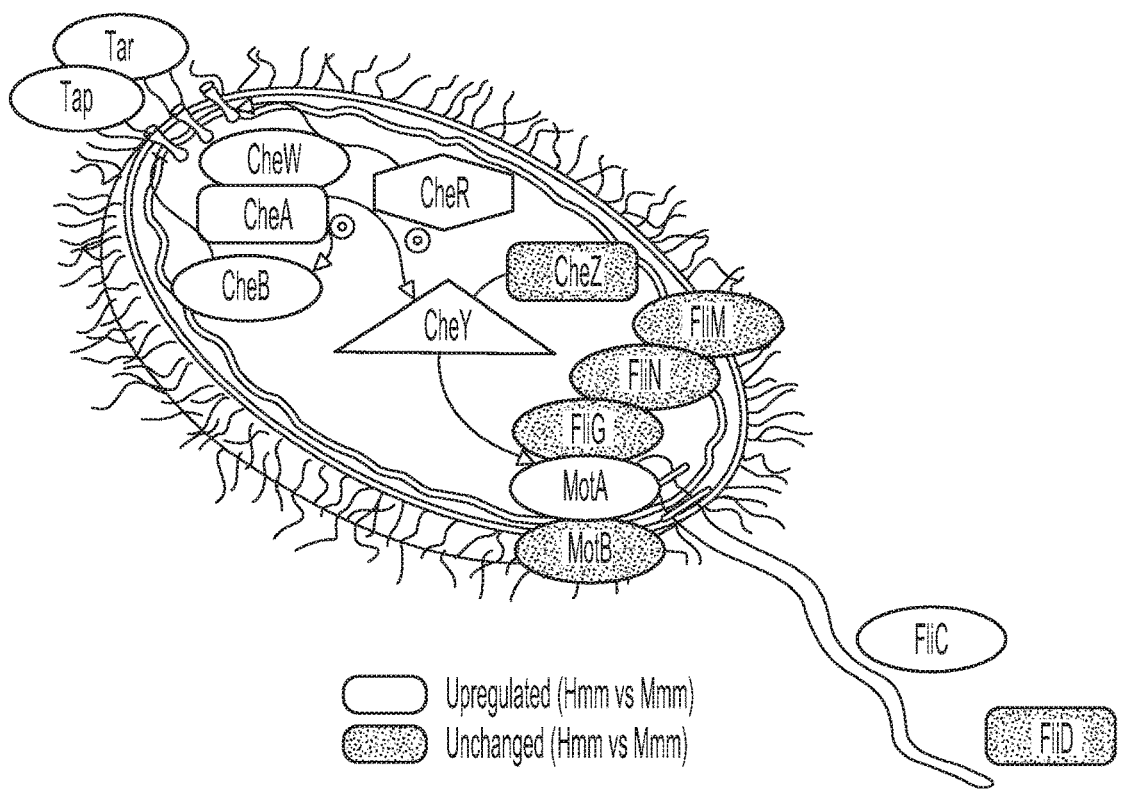
FIG. 19D shows a schematic illustrating key genes critical in regulating chemotaxis and flagellar assembly in EHEC.

Referring specifically to FIG. 19C, a heat-map of chemotaxis and flagellar assembly pathways shows expression levels for relevant motility-related genes in EHEC cultured in the presence of Hmm versus Mmm. Referring specifically to FIG. 19D, a schematic illustrates key genes critical in regulating chemotaxis and flagellar assembly in EHEC. Referring specifically to FIG. 19E, EHEC swimming motility tracking is illustrated (lines: bacterial movement tracks; dots: starting points for all tracked bacteria; bar, 100 μm).

Figure 19F:
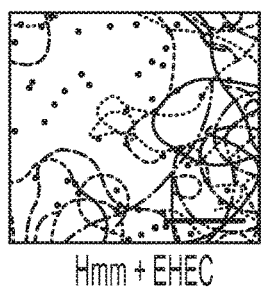
FIG. 19F shows a graph illustrating quantification of a fraction of moving EHEC.
Figure 19F:
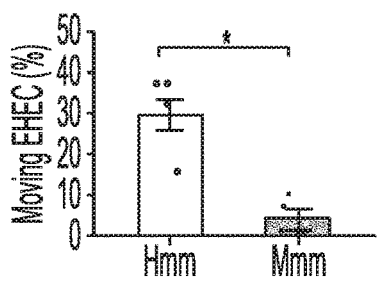
Figure 19G:
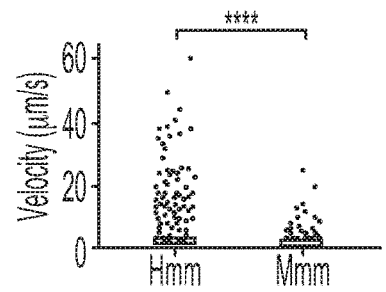
FIG. 19G shows a graph illustrating mean velocity of each tracked bacterium.
Figure 19E:
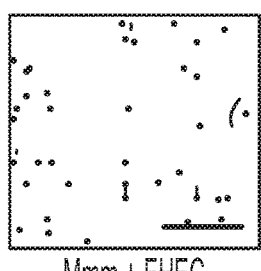
FIG. 19E shows plot images illustrating EHEC swimming motility tracking.
Figure 19H:
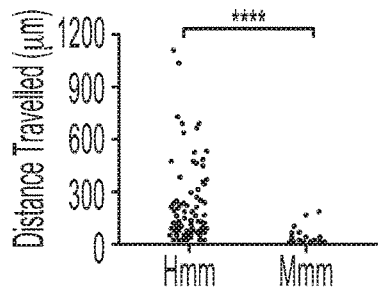
FIG. 19H shows a graph illustrating a distance traveled by a moving bacteria.
Figure 19I:
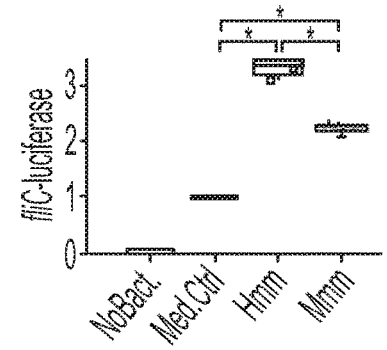
FIG. 19I shows a graph illustrating Fli-C-luciferase expression levels.

Referring specifically to FIG. 19F, quantification of the fraction (%) of moving EHEC is illustrated. Referring specifically to FIG. 19G, mean velocity of each tracked bacterium (red and black: velocity < or >3 μm s-1, respectively) is illustrated. Referring specifically to FIG. 19H, a distance traveled (μm) by the moving bacteria is illustrated. Referring specifically to FIG. 19I, Fli-C-luciferase expression levels are illustrated in medium supplemented with Hmm or Mmm (determined by quantifying area under the curve (AUC), and normalizing for the medium control) ($*p<0.05$; $****p<0.0001$).

Figure 20A:
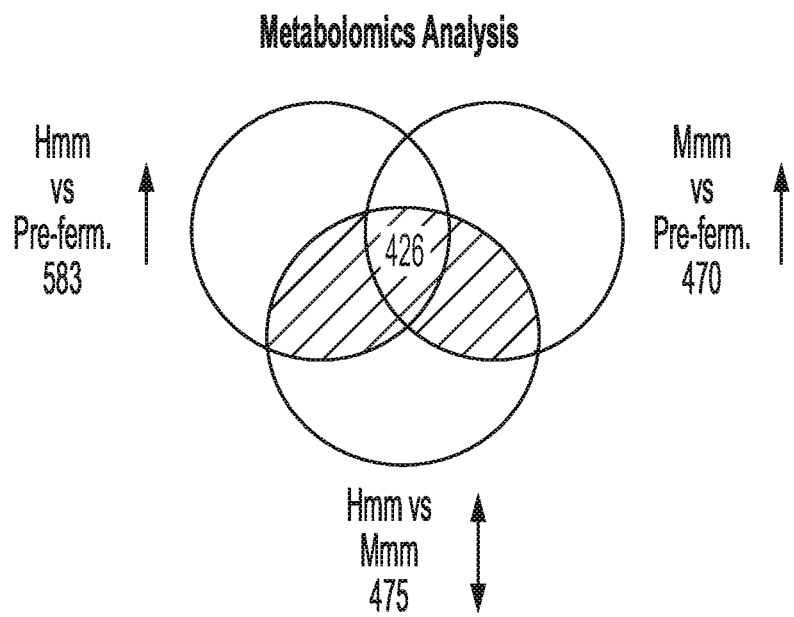
FIG. 20A shows a Venn-diagram illustrating metabolomics analysis workflow.
Figure 20B:
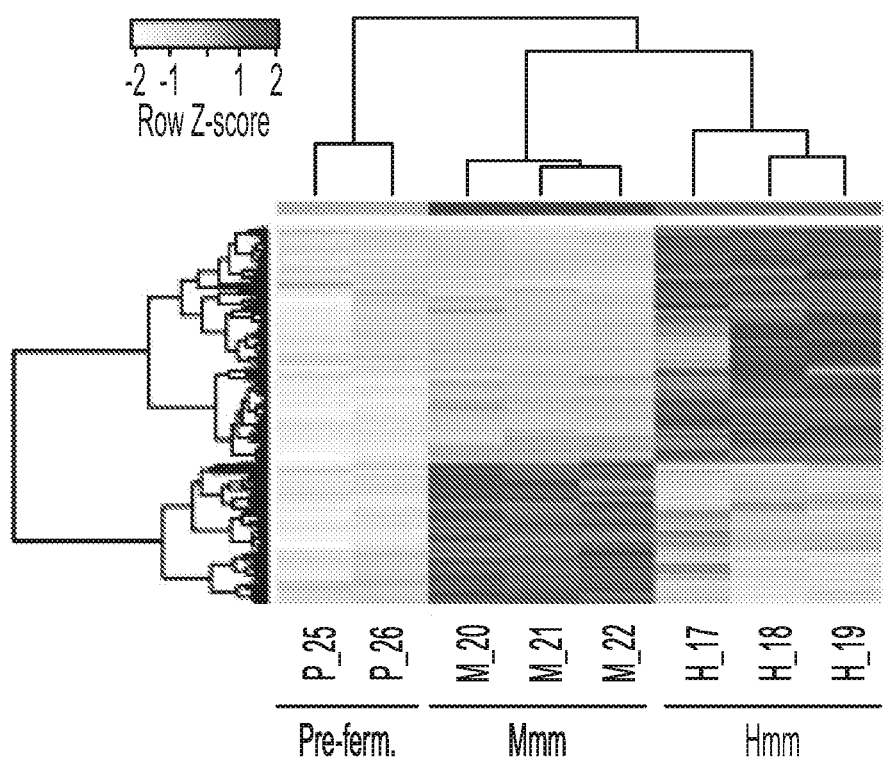
FIG. 20B shows a heat-map with 426 compounds produced by commensal bacteria.
Figures 20C, 20D:
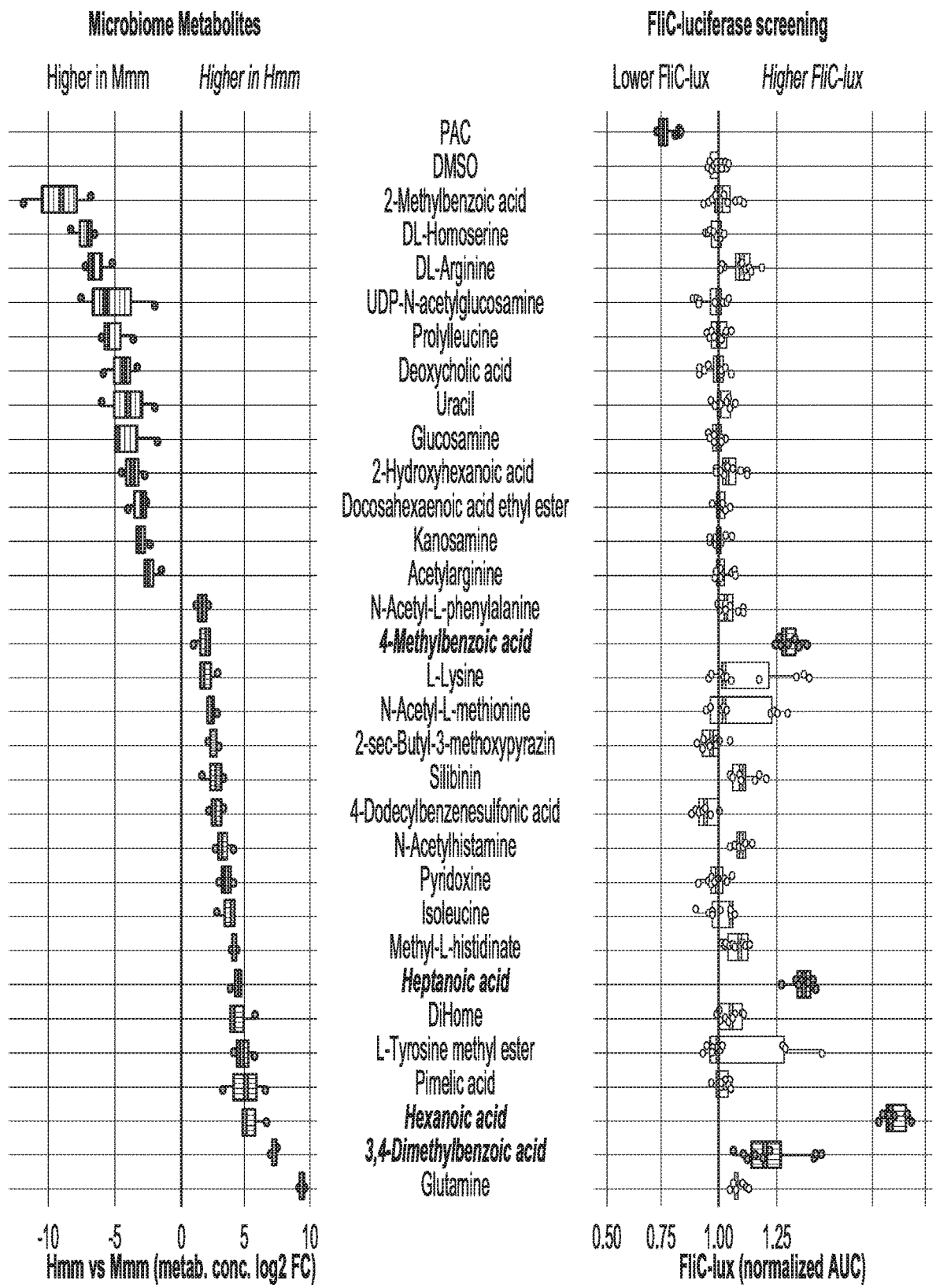
FIG. 20C shows a plot of relative abundance for 30 microbiome metabolites that were tested.
FIG. 20D shows a plot with results for FliC-luciferase (FliC-lux) screening for the 30 selected metabolites.

Referring generally to FIGS. 20A-20D, identification of specific metabolites that mediate EHEC motility is illustrated. Referring further generally to FIGS. 20A-20C, results of metabolomics analysis of human versus mouse gut microbiome metabolites are illustrated.

Referring specifically to FIG. 20A, a Venn-diagram illustrates metabolomics analysis workflow and total numbers of compounds identified in the Hmm and Mmm samples compared to the pre-fermentation medium (Pre-ferm.; label p_25: human pre-fermentation medium; label p_26 murine pre-fermentation medium). Referring specifically to FIG. 20B, a heat-map shows 426 compounds produced by commensal bacteria that were differentially abundant in human (Hmm) versus mouse (Mmm) microbiome metabolites.

Referring specifically to FIG. 20C, relative abundance shows 30 microbiome metabolites that were tested (blue and red: higher levels in Mmm or Hmm, respectively). Referring specifically to FIG. 20D, results show FliC-luciferase (FliC-lux) screening for the 30 selected metabolites (FliC-lux levels are presented based on quantification of the AUC; grape seed oligomeric proanthocyanidins (PAC) was used as a negative control; the 4 active metabolites that induced higher FliC levels are highlighted in red/brighter color; all values were normalized against the DMSO control).

Figure 21A:
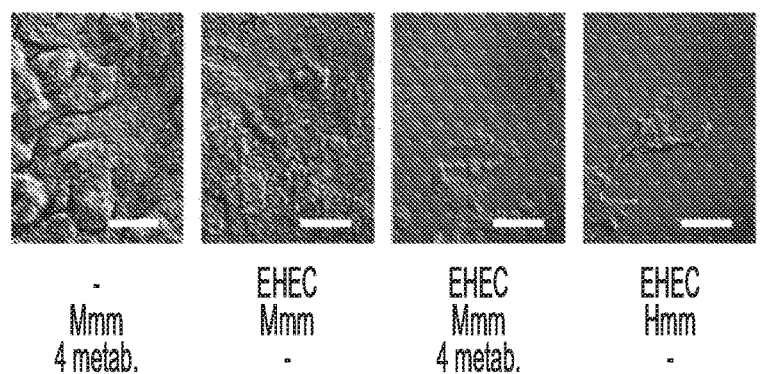
FIG. 21A shows representative DIC images of a colon epithelium under various experimental conditions.
Figure 21B:
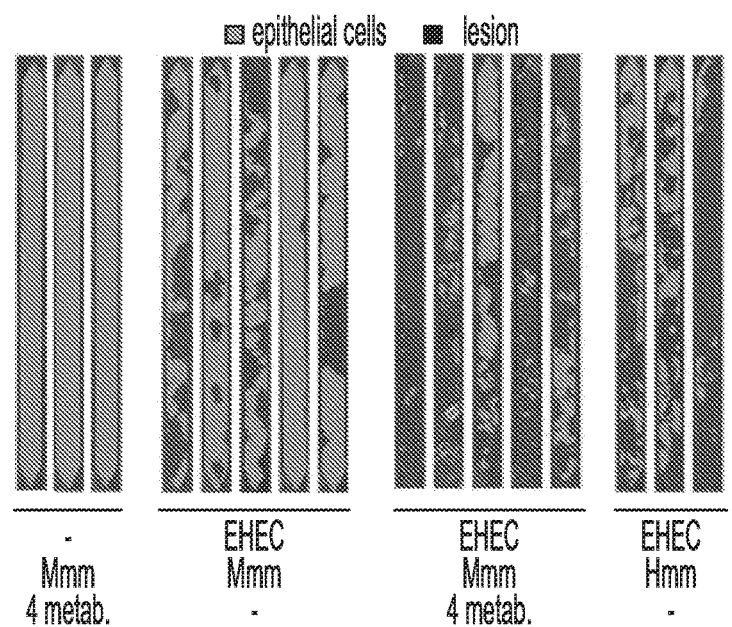
FIG. 21B shows images of an entire epithelial layer in a colon chip under the same conditions.
Figure 21C:
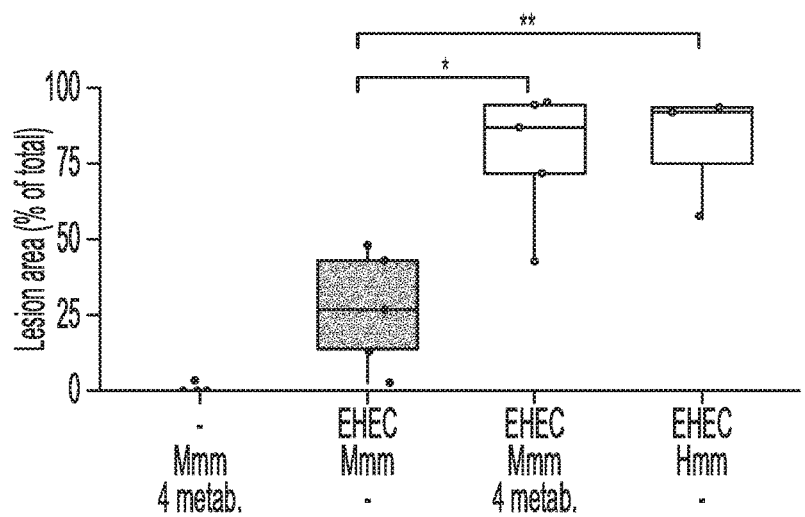
FIG. 21C shows a plot representing quantification of an epithelial area sized under conditions shown in FIG. 21B.

Referring generally to FIGS. 21A-21C, identified active metabolites mediate increased pathogenicity. Effect of 3,4-dimethylbenzoic acid, 4-methylbenzoic acid, hexanoic acid, and heptanoic acid (4 metab.) on epithelial injury in the colon chip is in the presence or absence of EHEC, with or without Mmm, compared to the effects of Hmm with EHEC.

Referring specifically to FIG. 21A, representative DIC images of the colon epithelium are shown under various experimental conditions (bar, 100 μm). Referring specifically to FIG. 21B, a pseudo-colored view of the entire epithelial layer in the colon chip (yellow or bright area) is shown under the same conditions. Referring specifically to FIG. 21C, quantification is shown of an epithelial lesion area sized under conditions shown in FIG. 21B. Epithelial lesion is defined as regions in which cells normally contained within a continuous intact epithelium have fully detached from the ECM-coated membrane and their neighboring cells, thus, leaving exposed regions of the membrane below ($*p<0.05$; $**p<0.01$).

In accordance with the disclosure provided above, the oxygen gradient is established across a lumen of the Gut Chip. To recapitulate a physiologically relevant intestinal oxygen gradient profile inside Organ Chips (shown in FIG. 1A), an oxygen-sensing, dual channel, human Gut Chip is fabricated that is composed of optically clear and flexible poly(dimethyl siloxane) (PDMS) polymer (FIGS. 1B and 5A), as well as a hypoxic chamber (FIGS. 6A and 6B). For real-time, non-invasive, monitoring of oxygen tension, six sensor spots containing oxygen-quenched fluorescent particles are embedded in the top and bottom portions of the Gut Chip beneath central microchannels (FIGS. 1B and 5A). Changes in the fluorescent intensities of these sensors in response to oxygen tension are captured by a Visisens camera (FIGS. 5B and 6A), and translated into oxygen concentrations by comparison with a standard Oxy-4 probe system (FIG. 5C). As both the chips and sensors are composed of highly gas-permeable PDMS, the sensors respond rapidly (e.g., <30 seconds) to changes in oxygen concentrations (FIG. 1C).

To simultaneously provide adequate oxygen for maintaining human cells and an anaerobic microenvironment suitable for culturing complex human microbiota while establishing a functional host-microbiome interface, the custom hypoxic chamber is flushed continually with humidified 5% $CO_2$ in nitrogen gas (FIG. 5B). This setup enables maintaining low oxygen levels within the lumen of the upper chamber (FIG. 1D), while the epithelium is sustained via diffusion of oxygen through the permeable PDMS membrane from the well-oxygenated medium flowing through the lower endothelium-lined vascular channel from external oxygenated medium reservoirs (FIG. 6B). Using this method, anaerobic conditions (<0.5%) are generated within less than 30 minutes at 243 milliliters min' of nitrogen flow into the hypoxic chamber (FIG. 1D). The chamber also sustains these low oxygen levels (e.g., <5.0%) for about 15 minutes after it is disconnected from the nitrogen source (FIG. 1D). This allows the chamber to be temporarily moved from the incubator for imaging or into a bacterial glove box (e.g., to replenish culture medium or add microbiota) without significantly disturbing the low oxygen environment.

When human Caco-2 intestinal epithelial cells are cultured for 5 to 7 days under aerobic conditions and dynamic flow, they undergo villus differentiation and express multiple features of the ileum portion of the human small intestine, including secretion of a mucus layer overlying the apical surface of the epithelium and establishment of barrier function. Endothelial cells are also co-cultured on the bottom of the central porous membrane in the lower channel of the same device, where they form a hollow vascular lumen lined by cells joined by VE cadherin-containing cell-cell junctions under aerobic conditions. The co-culture of endothelium has been shown to enhance barrier function and mucus production (e.g., expression of MUC2 and MUC5AC), as well as influence villi development and cytokine production by intestinal Caco2 epithelium under these conditions. When Gut Chips are cultured lined by these same two human intestinal cell types under a hypoxia gradient using the chamber, differential interference contrast (DIC) and immunofluorescence microscopic analysis confirms the cells again formed a villus intestinal epithelium containing polarized cells joined by ZO-1-containing tight junctions (FIG. 1E, top) and a confluent HIMEC monolayer with cells linked by VE-cadherin-containing tight junctions even under these anaerobic culture conditions (FIG. 1E, bottom). Both cell types also remain viable under these conditions, as measured by quantifying release of the intracellular enzyme lactate dehydrogenase (LDH), which remained relatively unchanged compared to the aerobic control during one week of anaerobic culture (FIG. 7A).

Measurements of apparent permeability ($P_{app}$) of the intestinal epithelial barrier similarly reveals no changes in the paracellular barrier function, and these human Gut Chips display $P_{app}$ values of about $1\times10^{-7}$ centimeters $s^{-1}$ after 7 days (FIG. 7B), which are similar to those previously reported. Importantly, the present disclosure confirms that both the human intestinal epithelium and endothelium experience these oxygen gradients by demonstrating that expression of hypoxia-inducible factor 1α (HIF-1α), a key mediator of oxygen hemostasis and intestinal epithelial cell adaptation to oxygen deprivation (which is stabilized in a graded fashion in response to decreasing oxygen concentrations), is significantly higher (~3-fold) in the anaerobically-cultured epithelium lumen where the sensors indicate a maintenance of a hypoxic environment for up to 7 days in culture (FIG. 1F), than in the adjacent oxygenated endothelium (FIGS. 8A and 8B).

The co-culture of human intestinal epithelium is disclosed below with an obligate anaerobe on-chip. Specifically, a hypoxic environment is explored to determine if it can support co-culture of the intestinal epithelium with the obligate anaerobe, Bacteroides fragilis (B. fragilis; strain NCTC 9343), which is a human commensal symbiotic bacterium that cannot grow under aerobic conditions. B. fragilis bacteria ($2.5 \times 10^5$ CFU; fluorescently labeled with HADA[25]; FIG. 9A) is introduced into the lumen of the intestinal epithelium-lined upper channel (FIG. 9B) and subsequently cultured under either aerobic or anaerobic conditions, while being flushed daily to carry out CFU counts by plating. Continuous monitoring of oxygen concentration from inoculation to day 3 of co-culture reveals that the anaerobic chip setup maintains a low oxygen environment that decreases from ~1% oxygen levels to 0.3% in the presence of B. fragilis (FIG. 2A). Yet, the intestinal epithelium maintains its ZO-1-containing tight junctions and apical brush border polarity when co-cultured in direct contact with B. fragilis under these conditions (FIG. 2B). Interestingly, the presence of this obligate anaerobe enhances barrier function (reduced $P_{app}$ by 1.8-fold compared to aerobic conditions; FIG. 2C) after 3 days in anaerobic culture and maintains the barrier for up to 8 days in culture. As expected, the B. fragilis bacteria continues to grow in the anaerobic chips over 3 days, whereas they die off and remain at significantly lower levels under aerobic culture conditions (FIG. 2D). This data confirms that the hypoxic chips support the growth of an anaerobic bacterial species in direct contact with living human intestinal epithelial cells. This bacteria would have otherwise died in a conventional aerobic microfluidic system.

A mucus layers separates the commensal microbes from the epithelium. One of the characteristic features of host-microbiome interactions in the living intestine is that they are mediated through an intervening mucus layer that is secreted by the epithelium along its apical surface. Live staining using Wheat Germ Agglutinin (WGA), which has been previously used for mucus visualization in vitro and in vivo, confirmed that B. fragilis resides on top of the mucus layer (FIG. 2E), which is secreted by the intestinal Caco2 epithelium. This was independently confirmed by scanning electron microscopic (SEM), which clearly revealed a continuous and dense mucus blanket that completely covered the surface of the differentiated villus epithelium separating it from overlying bacteria after 12 days of culture (FIG. 2F), much as is observed in vivo. This was in contrast to SEM analysis of Caco2 intestine chips that were only cultured for 4 days before full differentiation occurred and mucus had accumulated where the microvilli-lined surface of the apical epithelium remained clearly detectable (FIG. 2F). Based on these images, the thickness of mucus layer was estimated at ~10 μm, which is similar to that reported with 30-day old mouse ileum.

A complex human intestinal microbiome is sustained in vitro. The hypoxic Gut Chips are inoculated with a sample of complex gut microbiome originally isolated from human feces, which has been stably maintained in gnotobiotic mice (Hmb mice) in isolators for over 30 generations. To identify a medium composition that would promote the growth of a complex set of commensal bacteria, the microbiome stock is first inoculated into 13 different types of culture medium in standard culture tubes, then the cultures are laced in an anaerobic chamber at 37° C., and then 16s rRNA are carried out sequencing after 3 days of culture (FIG. 10A). Samples of these 13 types of medium are also added to cultured human intestinal epithelial cells to test for toxicity (FIG. 10B). The medium that promotes the most diverse set of viable microbes without injuring the epithelium contains DMEM, 20% FBS, 1% glutamine, 1 mg·ml$^{-1}$ pectin, 1 mg·ml$^{-1}$ mucin, 5 Hemin and 0.5 μg·ml$^{-1}$ Vitamin K1. The microbiome stock is introduced into this medium (0.1 mg·ml$^{-1}$) and perfused through the upper epithelium-lined channel of the Gut Chip while oxygenated endothelial culture medium is flowed through the lower channel. Chips are flushed daily and 16S rRNA sequencing is carried out using samples from the effluent of the epithelial channel to assess the bacterial diversity in each condition over 3 days of culture.

After data processing, a total of 938 OTUs are identified among all samples, which corresponded to approximately 200 unique OTUs shared between samples of each chip after filtering and removing singletons. Analysis of the alpha diversity between the two conditions shows that the species diversity in anaerobic chips is statistically different from aerobic chips (PERMANOVA, p<0.001), with the trend being maintained across all 3 days of co-culture (FIG. 3A). Interestingly, co-culturing of these diverse microbiota under hypoxic conditions for 2 days in direct contact with the human intestinal epithelium does not compromise intestinal barrier function, and instead, it increases barrier function by almost 2-fold (i.e., decreases the $P_{app}$ from $3.1 \times 10^{-7}$ centimeters s$^{-1}$ to $1.6 \times 10^{-7}$ centimeters s$^{-1}$ in aerobic versus anaerobic chips) (FIG. 3B). In contrast, epithelial barrier function actually decreases by day 3 of co-culture under aerobic conditions when co-cultured with complex gut microbiome.

To further assess the physiological mimicry obtained using the hypoxic Gut Chip, the bacterial genera of the present disclosure is compared with publicly available data from studies of human stool generated by the Human Microbiome Project (FIG. 3C). The results show that the anaerobic culture system provides an environment for complex gut microbiome that sustains a diverse bacterial community that is more similar to human stool than the aerobic system. The relative abundances of the phyla Bacteroidetes and Firmicutes (Blautia, Oscillospira, and Suterella species) in the anaerobic Gut Chips are similar to those previously observed in human stool, and they are all higher than the levels detected under aerobic conditions (FIG. 3C). Interestingly, Akkermansia muciniphila, which has been recently implicated as an enhancer of gut barrier function, is more abundant in the anaerobic culture system than in stool while Parabacteroides is lower in both culture systems indicating some gut microbial species stabilize at different ratios in the Gut Chip cultures compared to stool. Nevertheless, this data confirms that this hypoxic human Gut chip system enables living human intestinal epithelium to be co-cultured in direct contact with complex human gut microbiome containing a range of bacterial genera that comes much closer to what is observed in healthy human volunteers than has ever been possible before.

To determine if the microbial communities in the anaerobic Gut Chip system are stable, growing, or dying during culture on-chip, their relative abundance is analyzed over the 3 days of co-culture with human intestinal epithelium and underlying endothelium (FIG. 4A). It was found that genera composed of obligate anaerobes, such as *Akkermansia, Oscillospira, Blautia*, and *Suterella*, actually increased over time, presumably due to maintenance of low oxygen concentrations, whereas facultative anaerobic bacterial genera, such as *Enterococcus*, decreased (FIG. 4A). *Bacteroides*, which is the highest abundance genus in the anaerobic Gut Chips, remain relatively stable over time and are maintained at higher levels than in aerobic chips (FIGS. 4B, 4C, and 11), again confirming that the hypoxia gradient system provides a preferential environment for culture of both *Bacteroides* and various Firmicutes genera.

When comparing the microbiome in the 3-day hypoxic Gut Chip co-cultures with the microbiota cultured for a similar time in conventional liquid medium culture in an anaerobic chamber, some genera are found to grow better in the Gut Chip, whereas other genera displayed the opposite behavior (FIG. 4B). Notably, *Akkermansia mucinophila* grows better in the anaerobic Gut Chip, presumably because the intestinal epithelium produces mucin, which can help fuel its growth. On the other hand, the Gram-negative obligate aerobe, *Citrobacter*, is less abundant on-chip compared with liquid culture. Finally, the differential abundance of genera is compared over time in the anaerobic versus aerobic Gut Chips. As expected, an increase is observed in abundance of obligate anaerobes, such as *Sutterella, Bilophila, Blautia, Oscillospira* and *Akkermansia*, as well as a concomitant decrease in the abundance of *Citrobacter*, in the anaerobic chips compared to the aerobic chips (FIG. 4C).

The feasibility of using the present anaerobic co-culture method with patient derived specimens was demonstrated by inoculating recently developed primary human Small Intestine-on-a-chip (Small Intestine chip) with microbiota from human fecal samples. The Small Intestine chip utilizes organoids established from intestinal biopsy specimens or tissue resections of living human intestine to create 3D intestinal villus-like structures which exhibit epithelial barrier function, multi-lineage differentiation, enzymatic activity of brush border enzymes and mucus production. For this study, ileal biopsies were initially used because this region has the highest bacteria concentration in the small intestine and is of interest in disease pathologies such as Crohn's and necrotizing enterocolitis. DIC and confocal fluorescence microscopic analyses of primary human ileal chips confirmed the presence of a continuous, polarized, epithelial cell monolayer with an apical F-actin-containing brush border and basal nuclei aligned along the boundary of each villin-stained extension into the lumen of the epithelial microchannel of the chip. Fecal samples from neonatal intensive care patients (1 mg·ml$^{-1}$) were introduced to the apical surface of the ileal chip in differentiation media containing microbial supplements while oxygenated expansion media was flowed through the basal channel. Chips were co-cultured with microbiota for 5 days during which time they maintained epithelial harrier function (up to $P_{app} \sim 1 \times 10^{-6}$ cm·s$^{-1}$) while supporting an average bacterial richness of 124 OTUs corresponding to 32 unique genera. While there is limited data on human neonatal ileum microbiota, it is likely to be less rich than the adult ileal mucosa which exhibits a richness varying from 131 MTh up to 907 OTU. Similar studies were also carried out on duodenal chips with a lower density of bacteria (0.01 mg·ml$^{-1}$) to reflect the lower density of bacteria present in this segment of the small intestine in vivo. The lower optical density of the bacteria allowed for real time visualization of bacteria surrounding villi and penetrating regions above crypts, which is similar to the spatial organization observed in vivo.

An experimental approach is further directed to culture of fresh microbiome with primary intestinal epithelium on-chip. This experimental approach is directed to co-culture complex gut microbiome obtained from fresh human stool specimens in direct contact with primary human intestinal epithelium (i.e., rather than using the established Caco2 intestinal cell line). To do this, human intestine chips are engineered and lined with intestinal epithelial cells isolated from organoids derived from normal regions of surgical biopsies of human ileum, which exhibit multi-lineage differentiation, villi formation, and mucus production when grown on-chip. The epithelial channels of 4 different chips are inoculated with complex microbiome isolated from fresh human stool samples collected from four different infants (one with a corrected gestational age of 30 weeks and three with an age of 36 weeks). DIC (FIG. 16A) and confocal fluorescence microscopic (FIG. 16B and FIG. 17A) imaging of the primary human ileum chips confirmed the presence of a villus intestinal epithelium lined by a continuous polarized epithelium with F-actin- and villin-containing brush borders along its apical membrane, MUC2-producing cells, and basal nuclei. Of note, when production of secreted mucus is measured using alcian blue staining (FIG. 17B), blue stained mucus is observed over the apical surface of the epithelium, and up to 600 ug·ml-1 of mucin is detected in the chip outflow (FIG. 17C). As expected, the bacterial richness is reduced in the infant stool stock (586 OTUs) compared to adult human-derived stool (938 OTUs) at the same dilution per gram of materials, and these differences in richness are accurately recapitulated on-chip. The primary human intestinal epithelium is co-cultured in direct contact with this complex gut microbiome without compromising epithelial barrier function, and this co-culture is stably maintained for up to at least 5 days on-chip (FIG. 16C), much as observed with the Caco2 epithelium. Of further mote, the microbiome cultured in these primary intestine chips also maintains a high bacterial richness, ranging from 118 to 135 OTUs (FIG. 16D) corresponding to 6 phyla (Actinobacteria, Bacteroidetes, Cyanobacteria, Firmicutes, Proteobacteria and Tenericutes) and 32 unique genera. Thus, the hypoxic intestine chip method is used to sustain a complex community of human microbes in direct contact with normal, patient-derived, human intestinal epithelial cells for many days in culture, which is valuable for personalized medicine in the future.

Based on the importance of commensal gut microbiome for human health and the lack of any in vitro model that can faithfully mimic the complex gut-microbiome interface, human Organ Chip technology is leveraged to develop a device that enables human intestinal epithelium to be co-cultured with the highly diverse community of commensal microbes that comprises the human gut microbiome under aerobic and anaerobic conditions. The results show that the hypoxic human Gut Chip model offers a robust modular platform for recapitulating the human intestinal-microbiome interface in vitro. Using this method, for the first time, it is possible to stably co-culture a complex living microbiome with living mammalian cells for days in vitro. This model accurately recapitulates in vivo behaviors, including the maintenance of an abundance of obligate anaerobic bacteria with ratios of Firmicutes and Bacteroidetes similar to those observed in humans feces. These studies also reveal that commensal gut microbiota cultured under anaerobic conditions enhance intestinal barrier function, which is also consistent with in vivo findings.

Using a custom-designed hypoxic chamber and chips containing oxygen sensors that enable monitoring of local oxygen concentrations on-chip, in vivo-like oxygen gradients are recapitulated that demonstrate morphological and functional changes in the intestinal epithelium in response to these altered oxygen levels. When the epithelium on-chip is co-cultured with either the obligate anaerobe, *Bacteroides fragilis*, or complex human microbiome isolated from human feces under anaerobic conditions, increased bacterial growth is observed compared to aerobic conditions. This observation is further accompanied by enhanced intestinal barrier function. Importantly, providing a physiologically-relevant oxygen microenvironment also sustains a high level microbial diversity (~200 unique OTUs), increases abundance of obligate anaerobic microbiota compared to aerobically-cultured chips, and maintains a diverse community of commensal microbe that closely resembles that of the human gut microbiome in vivo.

Oxygen tension is one of the main regulators of intestinal function and pathogenesis of GI diseases. By integrating non-toxic oxygen sensors into the devices of the present disclosure, oxygen levels are measured throughout the microfluidic Gut Chips without interference with microscopy imaging, device fabrication or cell culture. Use of these sensors, rather than incorporating multiple external oxygen-detecting probes, enables this approach to be more easily scaled to create many miniaturized Organ Chip platforms. The disclosed engineered hypoxic chamber also generates radial oxygen gradients across the endothelium-epithelium-microbiome interface that allows oxygenation of the human tissues while providing an anaerobic environment for growth of the obligate anaerobes. Anaerobic incubators or glove boxes are used to maintain hypoxic conditions for bacterial cultures, but they commonly provide a single uniform low oxygen concentration, rather than physiologically-relevant oxygen gradients directed across tissue-tissue interfaces. In contrast, the disclosed hypoxic chamber is portable, highly customizable, compatible with imaging, and most importantly, capable of engineering oxygen gradients across the endothelial-epithelial interface of any Organ Chip on demand.

Oxygen concentrations in the lumen of the human intestine are known to affect the spatial distribution and metabolism of gut flora, and most intestinal bacteria are obligate anaerobes that fail to grow at oxygen concentrations greater than ~0.5%. Any culture systems that is designed to recapitulate the host gut-microbiome interface must therefore be able to achieve and sustain oxygen concentrations at these low levels. A past microfluidic-based anaerobic culture system maintained oxygen levels as low as 0.8% using oxygen scavengers, but this level is still too high to support obligate anaerobes. Using the disclosed custom hypoxic chamber, an oxygen concentration is attained that is less than 0.3% in the epithelial channel where the commensal microbes are cultured. This is much closer to that found in the gut lumen in vivo. Most importantly, the relevance of these hypoxic culture conditions is validated by showing that they support the growth of the obligate anaerobe *B. fragilis* that cannot grow in the presence of greater than ~0.5% dissolved oxygen, whereas most of these bacteria died off after 3 days of in vitro culture under conventional aerobic conditions. Furthermore, the finding that co-culture of the human intestinal epithelium with *B. fragilis* under anaerobic conditions also increases (rather than decreasing) intestinal barrier function on-chip is consistent with the finding that oral delivery of *B. fragilis* corrects intestinal permeability defects in a mouse autism model.

More importantly, the hypoxic human Gut Chip model supports co-culture of complex human microbiota composed of over 200 unique OTUs and at least 11 different genera of bacteria for at least 3 days in co-culture. Bacterial members of the Bacteroidetes and Firmicutes phyla, and to a lesser degree Verrucomicrobia and Proteobacteria, which dominate human intestinal microbiome in vivo, also dominate the disclosed Gut Chips. In addition, growth of other species is supported, such as *Coprococcus, Anaerobacillus, Bifidobacterium*, and *Peptoniphilus*, only in the anaerobic chips, whereas Proteobacteria that accumulate mainly at more oxygenated regions of the proximal GI tract dominates the aerobic chips.

There remains a need to dilute the complex microbiome inoculum to avoid rapid unrestrained bacterial overgrowth. This may result in exclusion of some rare bacteria; however, this is ameliorated by using larger Gut Chips, optimizing the lumen perfusion rate, applying cyclic (peristalsis-like) mechanical deformations, or altering medium conditions to limit bacterial overgrowth. Nevertheless, this data shows that the anaerobic system promote more bacterial diversity than the aerobic system. Moreover, the anaerobic human Gut Chip supports a wide range of bacterial genera similar to those found in human stool, which is much more complex than any microbiome community that has been previously cultured stably for days directly in contact with mammalian cells in vitro.

Others have previously maintained complex microbiota in test tube cultures, however, the results of the present disclosure indicate that the presence of a more in vivo-like intestinal tissue microenvironment significantly influences the composition of the microbial community. For example, the mucus requiring, obligate anaerobe *Akkermansia muciniphila* is found in higher abundance in the anaerobic gut chips containing human intestinal epithelial cells that secrete mucus than in similarly anaerobic liquid cultures that are artificially supplemented with mucin. In contrast to liquid cultures, the hypoxic Gut Chip also enables identification of effects of commensal microbes on the host epithelium and vice versa. For example, it is interesting that the enhanced growth of *Akkermansia* muciniphila in the anaerobic Gut Chip is accompanied by increased intestinal barrier function because the high abundance of this organism has been suggested to enhance gut barrier function in vivo. HIF-1α is also believed to control barrier integrity by regulating multiple barrier-protective genes, and its dysregulation may be involved in GI disorders. Interestingly, although elevated HIF-1α expression in anaerobic Gut Chip is observed, no changes are detected in barrier function unless co-culturing complex microbiota.

The purpose of this disclosure is to describe an anaerobic method for co-culturing human epithelial cells with complex human microbiome in an organ-relevant microenvironment in vitro. Although this capability is demonstrated for the human intestine, the same methodology is applicable to study host-microbiota interactions in any Organ Chip (e.g., lung, skin, etc.). Caco2-seeded Gut Chip has been initially chosen because it not only exhibits many functions of normal human intestine but also more closely resembles the ileum than other parts of the intestine. However, in aerobic condition intestinal villi grow high enough to occlude the top channel and thus, interfere with constant medium flow and extended co-culture periods. Because villi in the primary intestinal chips grow more slowly than the Caco2 cells, the co-cultures of complex human microbiome extend for up to 5 days without compromising the epithelial viability and integrity. By integrating primary epithelial cells from intestinal biopsies or patient-derived induced pluripotent stem (iPS) cells, as well as patient-derived microbiomes, it is expected to develop patient-, disease-, and location-specific, host-microbiome co-culture models. The Organ Chip technology also allows for the incorporation of other cell types, such as immune cells and pathogens, which play crucial roles in host gut-microbiome interactions. Thus, this methodology is applicable to unravel complex functional links between intestinal epithelial cells, immune cells, and gut microbes to understand mechanisms of human disease, discover new therapeutics, and advance personalized medicine.

The purpose of this disclosure is further to describe a method for co-culturing a complex living human gut microbiome, including obligate anaerobes which require strict anaerobic conditions (i.e., <0.5-1% $O_2$) to survive, in direct contact with human intestinal epithelial cells and their overlying mucus layer for extended times in vitro. Although no specific region of the gastrointestinal system was modeled using the chips, it is noted that organ chips can be lined by cells from different regions of the intestine (e.g., duodenum, jejunum, ileum, colon) and oxygen tensions appropriate for each region (e.g., from 5% to 0.5% moving from duodenum to colon) can be used, potentially introducing the microbiome aspirates from each of these regions. The primary intestine chip better recapitulates the morphology, multicellular composition, and gene expression patterns of the intestinal segment from which it was derived than other in vitro intestinal culture systems, such as the Caco2 chip and 3D intestinal organoids. Furthermore, by integrating primary epithelial cells from intestinal biopsies as disclosed here, or patient-derived induced pluripotent stem (iPS) cells, in combination with microbiomes obtained from the same patients, it is possible to develop patient-, disease-, and location-specific, host-microbiome co-culture models, and thus, pursue a personalized-medicine approach in the future. That said, the Caco2 intestine chips also recapitulate many features of human intestinal physiology and pathophysiology, and these cells can be obtained commercially (rather than requiring a patient biopsy), which would enable their widespread use by academic and industrial laboratories, as well as regulatory agencies (e.g., FDA).

Oxygen sensing Gut Chip manufacturing includes preparation of oxygen sensor spots by mixing oxygen sensitive and optical isolating particles (PreSens GmbH, Germany) at a weight ratio of 1:1 in methanol (sigma, 50 milligrams $ml^{-1}$) for 2 hours under constant stirring. PDMS prepolymer (Sylgard 184, Dow Corning) is added to the mixture at 1 gram $ml^{-1}$ and solvent is subsequently removed by applying −70 kPa vacuum at 55° C. for 2 hours. PDMS prepolymer is then mixed with a curing agent (Sylgard 184, Dow Corning) at a weight ratio of 10:1 for 4 minutes under vacuum, spin-coated (150 µm thick) onto a 5 centimeter silanized silicon wafer at 800 rpm for 2 minutes and cured at 60° C. for at least 30 minutes. The wafer is removed and the 150 µm thick film is punched into 1-millimeter diameter sensor discs using a biopsy punch. The sensor discs are dip-coated in an uncured PDMS (PDMS prepolymer; curing agent 10:1) and embedded into the PDMS channels of the Gut Chip by placing them in molds at the inlet, middle and outlet of both upper (epithelium) and lower (endothelium) channels, and cured in place at 60° C. for 30 minutes. Gut Chip fabrication is then followed as described previously. Using this two-step molding process, these sensors are placed directly on the surface of both the vascular and epithelial channels of the Gut Chips at their inlet, middle and outlet regions (FIGS. 1B and 5A). The chip fabrication and sensor integration steps involving plasma treatment do not interfere with sensor function or the functionality of the microfluidic chips (FIG. 5D), and the thickness of the sensors does not affect the oxygen readouts when maintained between 150 to 300 µm in height (FIGS. 5E and 5F).

Hypoxic chamber fabrication and validation includes having acrylic parts cut using a laser cutter (Epilog) and assembled together with an acrylic solvent (SciGrip Acrylic Cement). Gaskets are lasercut from adhesive-backed silicone rubber sheets (20 Shore A hardness, McMaster-Carr) and magnetic clasps are attached using adhesive backed magnets. The hypoxic chamber is tested using a calibrated Oxy-4 optical probe system (PreSens GmbH, Germany) to verify the hypoxic conditions. To do so, the chamber is purged with 5% $CO_2$ in $N_2$ bubbled through deionized water at 81 mL $min^{-1}$, 162 mL $min^{-1}$, or 243 mL $min^{-1}$ for 1 h at which point $N_2$ flow is stopped and the chamber allowed (3 h) to recover to atmospheric oxygen.

Oxygen sensing in the Gut Chip includes visualizing and quantifying the concentration of oxygen throughout the chip. Oxygen measurements are performed through non-invasive fluorescence read-out using VisiSens-system (PreSens GmbH, Germany). Using a CCD-camera and the VisiSens software (V1.1.2.10), oxygen amount is detected at sensor spots and displayed using a computer code in pseudo colors. The software is designed to calculate oxygen levels on the sensor spots via calibration of fluorescence reading with defined oxygen levels at 0 and 100% air saturation (i.e., 20.9% $O_2$ of all dissolved gas by volume). In all experiments, oxygen levels are quantified after comparing the readings with the calibration values. Air-saturated water and oxygen-free solution (Oakton, WD-00653-00) are used to calibrate the sensor spots. Because the field-of-view of the VisiSens camera is inherently small, a linear positioning system is designed (FIG. 5A) that positions the camera directly beneath the Gut Chips in the hypoxia chamber (FIG. 6A). This allows indexed motions of the camera to any sensor spot along the chip or between the chips and thus, facilitates reproducibly imaging multiple chips in one run. The sensors do not obscure regular imaging of the chips as they only cover a small portion of the culture area (~3 $mm^2$), allowing for regular monitoring of cultures throughout the experiment. A black opaque box is designed to cover the entire chip culture chamber and VisiSens camera, for blocking extraneous light. To analyze the accuracy of sensor spots inside the chips, custom gas mixtures are used with known oxygen concentration, i.e., 0, 1, and 12.5% $O_2$. The VisiSens imaging system is validated using an Oxy-4 optical probe system (PreSens) with optical fibers (POF-L2.5, PreSens, Germany).

For oxygen sensor analysis, images of oxygen sensors are processed in MATLAB (Mathworks). The images are binarized using Otsu's method. Morphological erosion and dilation is preformed to eliminate any spurious artifacts created during binarization. Simulated annealing is applied to find the correct assignment of sensors in each image regardless of the chip alignment. The sum of the distance of each of the sensor's centroids in the current image between the nearest sensor's centroid in the original image is minimized. After aligning the images, the sensors in the current image are registered consistently with the sensors in the former image, and colorimetric analyses are computed. The average intensities are calculated for each of the red, blue, and green channels, in each sensor. The uncalibrated signal from each sensor is taken to be the average green intensity divided by the average red intensity. The uncalibrated signal is then fit to a calibration curve.

A modified Michaelis-Menten two-point calibration is used as the most generalizable model, $C_{oxy}=k_{min}+(k_{max}-k_{min})\times[x_{g:r}/(k_{rate}+x_{g:r})]$; $k_{max}=a\times k_{atm}$, where $x_{g:r}$ denotes the ratio of average green intensity to average red intensity, $C_{oxy}$ is the fraction of atmospheric oxygen, $k_{min}$ is the sensor signal at anaerobic conditions, $k_{max}$ is the sensor signal when saturated with oxygen, and the concentration of oxygen is given as $C_{oxy}$. $k_{rate}$ explains the effect that the observed signal, $x_{g:r}$, has on the concentration of oxygen. The atmospheric oxygen concentration does not fully saturate the sensor with oxygen. To overcome this, actual maximum possible signal from a sensor, $k_{max}$, is estimated by multiplying the uncalibrated signal at atmospheric concentration, $k_{atm}$, by a scale factor α. The Michaelis-Menton curve is approximately linear between $x_{g:r}=k_{atm}$ and $x_{g:r}=k_{max}$, scaling by a linear coefficient does not hamper the equation's ability to generalize between sensors. The curve is fit using images acquired at known oxygen concentrations. The known concentrations are measured by Oxy-4 optical probe system (PreSens GmbH, Germany). The oxygen concentrations is also validated by flowing oxygen at known concentrations over the probe and sensor. Both $k_{rate}$ and a are fit using the data. The model produces a suitable fit for the data ($R^2$=0.990 training, $R^2$=0.997 and 0.998 for testing) (FIG. 6A). The fitted model generalized well for trials is repeated in different chips and on different days (FIG. 6B).

For cell culture procedures, prior to cell seeding, microfluidic sensor chips are activated using oxygen plasma (Diener ATTO) and functionalized with (3-Aminopropyl) trimethoxysilane (Sigma, 281778) as reported previously. Chips are then washed with ethanol, oven-dried at 80° C. and coated with 30 μg ml$^{-1}$ Collagen (Gibco, A10483-01) and 100 μg ml$^{-1}$ Matrigel (BD Biosciences, 356237) in the serum-free Dulbecco's Modified Eagle Medium (DMEM; Gibco, 10564011) for 1 hour at 37° C. Afterwards, human intestinal microvascular endothelial cells (HIMECs; ScienCell) are seeded (1.5×10$^5$ cells cm$^{-2}$) in the bottom channel of the chips, on opposite side of the porous membrane. Chips are then placed in a 37° C. incubator for 1.5 hours. For HIMECs culture, endothelial growth medium (EGM2-MV) containing human epidermal growth factor, hydrocortisone, vascular endothelial growth factor, human fibroblastic growth factor-B, R3-Insulin-like Growth Factor-1, Ascorbic Acid and 5% fetal bovine serum (Lonza Cat. no. CC-3202) is used.

Human intestinal epithelial cells (Caco2 BBE human colorectal carcinoma cell, Harvard Digestive Disease Center) are then seeded into the top microchannel of the chip (1.5×10$^5$ cells cm$^{-2}$) and incubated for 1.5 hours. Epithelial cells are fed with DMEM (Gibco, 10564011) containing Pen/Strep and 20% Fetal Bovine Serum (FBS; Gibco, 10082-147). After washing with 200 μl of medium, chips are cultured statically overnight to allow cells to form monolayers on both sides of the membrane. A day after seeding, top and bottom channels are perfused (60 μL h$^{-1}$) with epithelial medium and reduced-FBS endothelial medium, respectively. Chips are kept in this condition until villus-like intestinal epithelium spontaneously appears. For anaerobic culture, the same procedure is followed except that after 1 day of perfusion in aerobic conditions, chips are placed in a hypoxic chamber and continuously perfused with 5% $CO_2$ in $N_2$ flowed at 243 mL min$^{-1}$.

Referring to organoid culture procedure, for human intestinal organoids, de-identified endoscopic tissue biopsies were collected from grossly unaffected (macroscopically normal) areas of the ileum and duodenum in 10-14-year-old patients undergoing endoscopy for gastrointestinal complaints. Informed consent and developmentally-appropriate assent were obtained at Boston Children's Hospital from the donors' guardian and the donor, respectively. All methods were carried out in accordance with the Institutional Review Board of Boston Children's Hospital (Protocol number IRB-P00000529) approval. Tissue was digested in 2 mg·ml$^{-1}$ collagenase I for 40 min at 37° C. followed by mechanical dissociation, and isolated crypts were re-suspended in growth factor-reduced Matrigel (Becton Dickinson) and polymerized at 37° C. Organoids were grown in expansion medium (EM) consisting of Advanced DMEM/F12 supplemented with L-WRN conditioned medium (50% v/v, ATCC), glutamax, HEPES, murine epidermal growth factor (50 ng·ml$^{-1}$), $N_2$ supplement, B27 supplement, human [Leu15]-gastrin I (10 nM), n-acetyl cysteine (1 mM), nicotinamide (10 mM), SB202190 (10 μM) and A83-01 (500 nM). Differentiation medium (DM) is EM without L-WRN conditioned medium, nicotinamide and SB202190, but supplemented with human recombinant R-spondin 1 (Peprotech; 1 μg·ml$^{-1}$), human recombinant Noggin (Peprotech; 100 ng·ml$^{-1}$) and γ-secretase inhibitor DAPT (10 μM). Organoids were passaged periodically by incubating in Cell Recovery Solution for 40 min at 4° C., followed by mechanical dissociation. Organoids were seeded on chips between passage number 5 and 25.

Referring to primary small intestine chip culture, microfluidic chips were obtained from Emulate Inc. (Boston, MA). Chips were chemically activated using Emulate ER1 and ER2 solutions. Type I collagen (200 μg·ml$^{-1}$) and Matrigel (1% in PBS) were then introduced into the channels, and incubated in a humidified 37° C. incubator for 2 h before washing with PBS. Epithelial organoids were isolated from Matrigel and the cells dissociated with TrypLE supplemented with 10 μM Y-27632. Epithelial cells were then re-suspended in EM (6×10$^6$ cells·ml$^{-1}$; of which 30 μl is used to fill the apical chamber of each chip resulting in ~180,000 cells·chip$^{-1}$), infused into the top channel, and incubated overnight in static at 37° C. The following day EM was perfused at 60 μl·h$^{-1}$ through the top and bottom channels and a peristalsis-like stretch (10% cell strain, 0.15 Hz frequency) was applied using a vacuum pump controlled by an electronic vacuum regulator (ITV009, SMC Corp.) and an Arduino microcontroller. Chips were maintained under these conditions until the visual development of villus like structures (~14 days). The apical media was then replaced with antibiotic free DM containing microbial supplements (1 mg·ml$^{-1}$ pectin, 1 mg·ml$^{-1}$ mucin, 5 μg·ml$^{-1}$ Hemin and 0.5 μg·ml$^{-1}$ Vitamin K1) and the basal media was replaced with antibiotic free EM.

Bacterial and microbiota culture includes *B. fragilis* (9343 strain) grown overnight at 37° C. under anaerobic conditions (80% $N_2$, 10% $H_2$, 10% $CO_2$) in rich media containing yeast extract (5 g L$^{-1}$), proteose peptone (20 g L$^{-1}$), NaCl (5 g L$^{-1}$), hemin (5 mg L$^{-1}$), vitamin K1 (0.5 mg L$^{-1}$), $K_2HPO_4$ (5 g L$^{-1}$) and HADA (HCC-amino-D-alanine, $\lambda_{em}$~450 nm; 0.8 mM). Hemin, vitamin K1, $K_2HPO_4$, and HADA[25] are added through a 0.22 μm filter after autoclaving the other ingredients. *B. fragilis* is pelleted at 5000 g, washed once in DMEM, and re-suspended in Caco2 media (DMEM 20% FBS, 1% glutamine, 1 mg ml$^{-1}$ pectin, 1 mg ml$^{-1}$ mucin, 5 μg ml$^{-1}$ Hemin, 0.5 μg ml$^{-1}$ Vitamin K1) at 1×10$^7$ CFU ml$^{-1}$. For microbiota co-culture, colon and cecum content from five mice colonized with healthy human microbiota[18] is collected and re-suspended in sterile PBS inside an anaerobic chamber (100 mg of content ml$^{-1}$). The slurry is then filtered (40 μm) and aliquoted and stored at −80° C. as the human microbiome stock, which is diluted 1:100 in epithelial medium when added to Gut Chips. For microbiota co-culture with patient-derived specimens, fecal samples were collected from infants born at Brigham and Women's Hospital in Boston, MA and cared for in a single-center Newborn Intensive Care Unit (NICU). Parental consent was obtained and all study procedures followed a protocol that was approved by the Partner's Human Research Committee for Brigham and Women's Hospital and Massachusetts General Hospital (Protocol number 2012-P-002453). Fecal samples were collected from preterm infants born prior to 32 weeks of gestation from birth until discharge. Briefly, diapers with fecal samples were collected daily by the bedside nurse, placed in a specimen bag, and stored at 4° C. for no more than 24 hours. Fecal material was extracted from diapers using sterile procedures and immediately frozen at −80° C. Selected samples were suspended in Brain Heart Infusion media (100 mg·ml$^{-1}$) to create a stock solution.

Gut-microbiota co-culture in Gut Chips includes washing media reservoirs with PBS 24 hours before adding bacteria. Antibiotic-free media is then added to Gut Chips in a tissue culture hood (aerobic conditions) or in an anaerobic chamber (anaerobic conditions). The next day, 25 µl of *B. fragilis* (1×10$^7$ CFU ml$^{-1}$) or microbiota stock (1:100) is added to the apical side of differentiated Gut Chips in a tissue culture hood (aerobic conditions) or in an anaerobic chamber (anaerobic conditions). Chips are left static for 30 minutes and then perfused at 1 µl min$^{-1}$. Every 24 hours, a 2-minute flush at 50 µl min$^{-1}$ is performed and the flush outflow is collected and serial dilutions are plated on *Brucella* plates incubated at 37° C. in an anaerobic chamber (*B. fragilis* cultures) or sent to Diversigen, Inc. (complex microbiota cultures) for 16S rRNA sequencing.

Morphological analyses include, for each experiment, analysis of 3 independent gut chip samples at each interval. The intestinal epithelium villus structures are evaluated using differential interface contrast (DIC) microscopy (Zeiss Axio Observer Z1 2, AXIO2). Immunofluorescence microscopy with a laser scanning confocal microscopes (Leica SP5 X MP DMI-6000 and Zeiss TIRF/LSM 710) is used to study the villus microarchitecture. High-resolution horizontal or vertical cross-sectional images are obtained using deconvolution (Huygens) followed by a 2D projection process. IMARIS (MARIS 7.6 F1 workstation; Bitplane Scientific Software) and ImageJ ae used for analyzing the obtained images.

For immunofluorescence microscopy, epithelial and endothelial cells are washed with PBS, fixed with paraformaldehyde (20 min; PFA, 4%; Electron Microscopy Sciences, 157-4) and subsequently washed with additional PBS. Permeabilization of cells is done with 0.25% Triton X-100 (20 minutes; 0.25%; Sigma, T8787), followed by incubation in blocking buffer containing 1% BSA (Sigma, A4503) and 10% donkey serum (Sigma, D9663) for 30 minutes at room temperature. Primary antibodies against ZO1 (Life Technologies, 33-9100, dilution 1:200), VE-cadherin/CD144 (BD Biosciences, 555661, dilution 1:200), Villin (Life Technologies, PA5-29078, dilution 1:100), HIF-1α (Abcam, ab16066, dilution 1:100) or Cleaved Caspase-3 (Cas-3, Cell Signaling, 9661, dilution 1:100) are added and incubated overnight at 4° C., followed by 6 PBS washes (5 min each).

Cells are then incubated with secondary antibodies (Life Technologies) for 1 hour at room temperature and washed with PBS afterwards. Cells are co-stained with DAPI (Invitrogen, D1306). For terminal deoxynucleotidyl transferase-mediated dUTP-biotin nick-end labeling (TUNEL) immunostaining, Click-iT TUNEL Alexa Fluor Assay Kit (Invitrogen, C10247) is used according to the manufacturer's protocol. Chips are co-stained with DAPI (Invitrogen, D1306) as the nuclear DNA marker. Apoptotic cells are counted from 20 different fields (10 fields each from 2 replicates) to get an average number of TUNEL- and Cas-3-positive cells per field. To induce apoptosis, chips are treated with 1 unit of DNase I solution for 30 min at room temperature. Microscopy is performed with a laser scanning confocal microscope (Leica SP5 X MP DMI-6000 or Zeiss TIRF/LSM 710).

Referring to mucus detection and visualization, Wheat Germ Agglutinin (WGA) Alexa Fluor 488 conjugate (Thermo Fisher Scientific) was used for live cell imaging. Briefly, WGA solution (25 µg·ml$^{-1}$ in culture medium) was flowed through the epithelium channel for 30 min. The top channel was washed subsequently with PBS in the dark and counter-stained with DAPI to visualize nuclei. To stain acidic mucopolysaccharides within the intestinal mucus, intestine chips were stained with 0.1% (w/v) alcian blue solution (pH 2.5; 8GX, Sigma) in 3% acetic acid (Sigma) by flowing the solution into the microchannels at 50 µL·h$^{-1}$ for 12 h, and then washing with PBS.

Referring to paracellular permeability measurements, 50 µg ml$^{-1}$ of cascade blue (5.9 kDa; ThermoFisher, C687) are introduced to the epithelium channel (60 mL hr$^{-1}$) and fluorescence intensity (390 nm/420 nm) of top and bottom channel effluents are measured using a multi-mode plate reader (BioTek NEO). Apical-to-basolateral flux of the paracellular marker is calculated based on the following equation: $P_{app}=(dQ/dt)/A·dC·P_{app}$ (cm s$^{-1}$) denotes the apparent permeability coefficient, dQ/dt (g s$^{-4}$) is molecular flux, A (cm$^2$) is the total area of diffusion and dC (mg mL$^{-1}$) is the average gradient.

Referring to cellular toxicity, CytoTox 96 Non-Radioactive Cytotoxicity Assay (LDH; Promega, G1780) is used according to the manufacturer's instructions to measure epithelium and endothelium death rate at different intervals in both aerobic and anaerobic culture conditions. Effluents are collected from top and bottom channels, mixed with LDH substrate reagent and incubated for 30 minutes. The enzymatic reaction is terminated using stop solution (containing acetic acid) and the absorbance at 492 nm is recorded using a multi-mode plate reader (BioTek NEO). The LDH activity is assessed using quadruplicate of each group, calculated after subtracting the background absorbance values and reported as a fold change of the total LDH values of control group.

Referring to rRNA sequencing analysis, raw reads are analyzed using QIIME 1.0 under standard protocols and resulting joined reads are aligned to the Greengenes database. A total of 938 operational taxonomy units (OTUs) are identified. As one of the steps in the disclosed analyses of the 16S sequencing data, OTUs that did not meet certain criteria in terms of representation across all the samples are removed. The data is loaded into R and the phyloseq package is used for further processing. After performing diversity analyses, all singletons are removed from the data set and the OTUs are summarized to the genus level, resulting in a total 42 unique genera. Differential abundance of these genera between the two culture conditions, i.e., aerobic and anaerobic, is done using the DESeq2 package. OTUs showing a differential abundance with an FDR corrected p-value q<0.05 are considered significant. The PERMANOVA test is run in R using the adonis function in the vegan package between aerobic and anaerobic conditions, as well as between the two oxygen conditions across the different days.

Referring to statistical analysis, all experiments are carried out at n=3-6 (see captions of respective figures), and results and error bars indicate mean±standard error of the mean (s.e.m). Data analysis is performed with a one-way analysis of variance (ANOVA) with Tukey HSD post hoc tests using Graphpad Prism software. Statistical analysis between two conditions is performed by an unpaired student's t-test. P values of less than 0.05 are considered to be statistically significant (*P<0.05, P<0.01, *P<0.001).

According to other embodiments, a two-channel design is expanded to bioreactors, including a parallel plate reactor or a rolled-up plate reactor. One of the benefits of the oxygen gradient, which enables co-culture of mammalian and bacterial cells, is the permeability of the membrane and the top of the device to oxygen. As such, the oxygen necessary for human cells is delivered from the bottom channel but, then, it is consumed by cells or it quickly diffuses-out through the top channel Chip body and through the perfuse channel itself. This aspect is maintained in large systems as long as there are two or more chambers or channels that enable the oxygen flux path.

According to other aspects of the present disclosure, it is further disclosed that endoscopic analysis of human patients infected with EHEC has revealed acute inflammation of the colon and ex vivo infection experiments similarly demonstrated colonization as well as attaching and effacing (A/E) lesions in human colonic biopsies. Humans are susceptible to EHEC infection at a very low dose (102) whereas the dose required to induce infections in mice is 100,000-fold higher.

Surprisingly, the present disclosed studies have discovered that human microbiome metabolites increased enterohemorrhagic *Escherichia coli* (EHEC)'s ability to induce epithelial damage. In fact, greater epithelial injury is observed when human metabolites are present, while EHEC does not induce lesion formation in the absence of microbiome metabolites. Epithelial damage is also associated with an increase in expression of EHEC genes related to known virulence pathways related to chemotaxis and motility.

In contrast, mouse microbiome metabolite product protects against the damaging effects of this infectious pathogen. Thus, in some embodiments, metabolites from samples of human gut biomes enhance epithelial injury during pathogenic bacteria infections of the gut.

Human microbiome metabolites including 4-methyl benzoic acid, 3,4-dimethylbenzoic acid, hexanoic acid, and heptanoic acid, added individually to a colon-chip enhance epithelial injury during a EHEC infection of the chip. Moreover, addition of these four identified human microbiome metabolites is sufficient to convert the tolerant murine microbiome phenotype into an injury response that mimics than produced by addition of the human microbiome products.

For example, on day 8 of a colon chip culture, the luminal culture medium is replaced with the same medium supplemented with human or murine microbiome metabolites (diluted 1:20 in a PBS-water based solution to 300 mOsm kg-1), while continuing to flow the same endothelial culture medium through the vascular channel. Perfusion is continued for 24 hours, followed by introduction of EHEC (1.7× 105; serotype O157:H7) into the apical lumen in the same medium for 3 hours under static conditions to allow for bacterial cell attachment; medium flow is then re-established and continued for 24 additional hours.

Although metabolic analysis is used to pursue the mechanism by which Hmm and Mmm produce different effects on EHEC-induced epithelial injury, the focus is on known metabolites because these compounds could be obtained commercially and tested experimentally to validate their effects. Other unknown microbiome-derived metabolites present in the Hmm sample may have additional modulating activities, which could be explored in the future using fractionation of the Hmm sample and in-depth mass spectrometry analysis.

A similar experimental approach can identify microbiome-derived modulators of other enteropathogens that exhibit species-specific differences in pathogenicity in the future. Further, the methods described herein are contemplated to offer new mechanistic insights into why certain individuals or species are more tolerant to specific infectious pathogens than others.

TABLE 1

List of exemplary 30 known metabolites enriched in Hmm compared to Mmm that are selected for fliC -luciferase screening (CAS n: Chemical Abstracts Service number; "name": metabolites with a known name; "similarity": closest MSMS spectrum in the reference database to the to the analyte, with a 95% confidence in identification).

| Compound Name | ID (weight_retention time) | CAS n | Identification |
| --- | --- | --- | --- |
| DiHome | 260.19857_2.219 | 263399-35-5 | similarity |
| 2-Hydroxyhexanoic acid | 132.07856_2.024 | 6064-63-7 | name |
| 2-Methylbenzoic acid | 272.10498_3.508 | 118-90-1 | similarity |
| 2-sec-Butyl-3-methoxypyrazin | 371.17888_4.51 | 24168-70-5 | similarity |
| 3,4-Dimethylbenzoic acid | 150.06795_2.412 | 619-04-5 | name |
| 4-Dodecylbenzenesulfonic acid | 326.22039_2.728 | 121-65-3 | similarity |
| 4-Methylbenzoic acid | 274.18934_2.471 | 99-94-5 | similarity |
| Acetylarginine | 114.07927_3.982 | 155-84-0 | similarity |
| Glutamine | 304.17409_7.141 | 5959-95-5 | similarity |
| Glucosamine | 143.0943_9.55 | 66-84-2 | similarity |
| Deoxycholic acid | 392.2928_2.451 | 83-44-3 | name |
| DL-Arginine | 174.11135_8.207 | 7200-25-1 | similarity |
| DL-Homoserine | 100.01609_3.117 | 1927-25-9 | similarity |
| Docosahexaenoic acid ethyl ester | 409.31776_2.465 | 84494-72-4 | similarity |
| Heptanoic acid | 130.09938_2.145 | 111-14-8 | name |
| Hexanoic acid | 116.08368_2.286 | 142-62-1 | similarity |
| Isoleucine | 187.13167_9.36 | 73-32-5 | similarity |
| Kanosamine | 160.08446_6.8 | 57649-10-2 | similarity |
| L-Lysine | 146.12996_13.781 | 56-87-1 | similarity |
| L-Tyrosine methyl ester | 195.13668_4.829 | 1080-06-4 | similarity |
| Methyl-L-histidinate | 169.0847_5.059 | 332-80-9 | similarity |

TABLE 1-continued

List of exemplary 30 known metabolites enriched in Hmm compared to Mmm
that are selected for fliC -luciferase screening (CAS n: Chemical Abstracts
Service number; "name": metabolites with a known name; "similarity": closest
MSMS spectrum in the reference database to the to the analyte, with
a 95% confidence in identification).

| Compound Name | ID (weight_retention time) | CAS n | Identification |
|---|---|---|---|
| N-Acetyl-L-methionine | 175.08435_4.076 | 65-82-7 | similarity |
| N-Acetyl-L-phenylalanine | 207.0894_5.157 | 2018-61-3 | name |
| N-Acetylhistamine | 153.0898_7.032 | 673-49-4 | name |
| Pimelic acid | 116.12072_2.346 | 111-16-0 | similarity |
| Prolylleucine | 228.15808_6.396 | 61596-47-2 | similarity |
| Pyridoxine | 168.98662_5.97 | 58-56-0 | similarity |
| Silibinin | 178.11017_3.861 | 22888-70-6 | similarity |
| UDP-N-acetylglucosamine | 98.04821_6.285 | 91183-98-1 | similarity |
| Uracil | 111.99201_6.581 | 66-22-8 | name |
| Dimethyl sulfoxide (DMSO) | NA | 67-68-5 | NA |
| Proanthocyanidin (PAC) | NA | 222838-60-0 | NA |

The following are exemplary materials and methods. Bioreactor cultures include soluble metabolites isolated from bioreactor cultures of complex populations of murine or human intestinalcommensal microbes. Human microbiome metabolites (Hmm) or mouse microbiome metabolites (Mmm) are collected from PolyFermS continuous intestinal fermentation bioreactors in which complex mouse or human microbiome samples are cultured for two weeks under conditions that mimic the internal milieu of the large intestine; the commensal bacterial content of the cultures was defined at the phylum and genus levels using 16S rRNA gene sequencing.

For metabolomics, samples are centrifuged at 10,000×g for 5 min followed by biphasic chloroform-methanol extraction. All samples are run for untargeted mass spectrometry on a ThermoFisher Q-exactive mass spectrometer. Compound Discovery Software is utilized to assign compound names (95% confidence). If the parent ion is not found, the compound with the closest spectrum is used as an identifier, thus indicating a potential substructure of the original metabolite. In the case of multiple metabolites matching to the same identifier, priority is given to the metabolite identified with the highest average area value. In one analysis, 426 metabolites are identified enriched in either Hmm or Mmm, and all the metabolites with an assigned compound name are selected. Within these metabolites, all 30 commercially available compounds are selected, while known synthetic prescription drugs, antimicrobial agents, or potential chemical contaminants (Table 1, examples) are excluded and screened them for their effect on EHEC flagellar motility. Some readouts include the following: 16S rRNA gene sequencing, using known methods; bacterial motility tracking; fliC-luciferase reporter assay; genomic DNA analysis, e.g. in biomes before, during and after incubation in a PolyFermS device, before, during (collected from effluent) and after incubation on-chip.

Referring to colon chip infection, colon chips were cultured in the intestinal lumen channel of a chip in 5% (vol vol-1) human or mouse gut microbiome metabolites isolated from PolyFermS bioreactors, diluted in phosphate-buffered saline (PBS; final osmolarity=300 mOsm kg-1) or 24 hours. The following day, the intestinal channel was infected with 1.7×105. EHEC-GFP or EHEC A fliC (both generated from NR-3 $E.$ $coli$/EDL931; serotype O157:H7), by adding the bacteria into the channel lumen in medium again with or without Hmm or Mmm. Chips were maintained under static conditions for 3 hours to promote EHEC colonization, and then perfused at 60 µl h-1.

For epithelial lesion analysis, one day post-infection, colon chips were washed with PBS and fixed with 4% paraformaldehyde in PBS for 2 hours. The chips were imaged using a Leica DM IL LED microscope and images were stitched together with Basler Phylon Software. The area occupied by cells and the total area of the chip were measured using Fiji software.

For bacteria viability, bacteria were grown 6 hours at 37° C. in medium, in some embodiments, containing Hmm or Mmm, then propidium iodide solution was added at a final concentration of 10 mg ml-1 for 5 min at room temperature.

For bacteria swimming plate assay, swimming motility was assessed using 0.25% agar LB plates. Overnight cultures of EHEC or EHEC-GFP bacteria were standardized at 1 OD600 and 1.5 µl of the culture medium was added to the center of the agar plate with a sterile pipette tip. Bacterial swimming was quantified at 12 hours, imaging the plates using a FluorChem M imaging system (ProteinSimple). The area occupied by bacteria was then measured using Fiji.

TABLE 2

Exemplary Reagents and resources.

| REAGENT OR RESOURCE | SOURCE | IDENTIFIER |
|---|---|---|
| Bacterial Strains | | |
| NR-3 *Escherichia coli*, EDL931, serotype O157: H7 | bei Resources | EDL931 (Serotype O157: H7) |
| NR-96 *Escherichia coli*, B2F1 (Serotype O91: H21) | bei Resources | B2F1 (Serotype O91: H21) |

TABLE 2-continued

Exemplary Reagents and resources.

| REAGENT OR RESOURCE | SOURCE | IDENTIFIER |
|---|---|---|
| EHEC fliC-luciferase (Serotype O157: H7) | This study | |
| EHEC fliC-luciferase (serotype O91: H21) | This study | |
| EHEC-GFP | This study | |
| EHEC ΔfliC | This study | |

Experimental Models: Cell Lines

| | | |
|---|---|---|
| Human Intestinal Microvascular Endothelial Cells (HIMEC) | ScienCell | Cat#2900 |
| Human Colonic Organoids | | |
| L-WRN | ATCC | Cat#CRL-3276 |

Chemicals, Peptides, recombinant proteins

| | | |
|---|---|---|
| Pectin (citrus) | Sigma-Aldrich | Cat#P9135 |
| Xylan (beechwood) | Chemie Brunschwig AG | Cat#APOBI3856 |
| Arabinogalactan (larch) | Lonza | Cat#189452 |
| Guar gum | Sigma-Aldrich | Cat#G4129 |
| Inulin | Cosucra | Cat#FIBRULOSE-F97 |
| Soluble potato starch | Sigma-Aldrich | Cat#S2004 -1KG |
| Soluble corn starch | Sigma-Aldrich | Cat#S9679 |
| Mucine | Sigma-Aldrich | Cat#M2378 |
| Casein acid hydrolysate | Sigma-Aldrich | Cat#A2427 |
| Peptone water | Thermo Fisher Diagnostics AG | Cat#CM0009B |
| Bacto tryptone | Becton Dickinson | Cat#211705 |
| Yeast extract | VWR International | Cat#1.11926.1000 |
| L-cysteine HCl | Sigma-Aldrich | Cat#W778567 |
| Bile salts | Thermo Fisher Diagnostics AG | Cat#LP0055J |
| $KH_2PO_4$ | VWR International | Cat#26923.298 |
| $NaHCO_3$ | Sigma-Aldrich | Cat#13433 |
| NaCl | VWR international | Cat#1000152 |
| KCl | Sigma-Aldrich | Cat#12636 |
| $MgSO_4$ anhydrated | Sigma-Aldrich | Cat#63140 |
| $CaCl_2 \cdot 2 H_2O$ | Sigma-Aldrich | Cat#1000039 |
| $MnCl_2 \cdot 4 H_2O$ | Sigma-Aldrich | Cat#63536 |
| $FeSO_4 \cdot 7H_2O$ | Sigma-Aldrich | Cat#12354 |
| Hemin | Sigma-Aldrich | Cat#H9039 |
| Tween 80 | Sigma-Aldrich | Cat#P8074 |
| Pyridoxine-HCl (Vit. B6) | VWR International | Cat#A8093.0025 |
| 4-Aminobenzoic acid (PABA) | Sigma-Aldrich | Cat#A9878 |
| Nicotinic acid (Vit. B3) | Sigma-Aldrich | Cat#N4126-100G |
| Biotine | Sigma-Aldrich | Cat#14400 |
| Folic acid | VWR International | Cat#A2085.0010 |
| Cyanocobalamin | Sigma-Aldrich | Cat#V2876 |
| Thiamine | Sigma-Aldrich | Cat#T4625 |
| Riboflavin | Sigma-Aldrich | Cat#R4500 |
| Phylloquinone | Sigma-Aldrich | Cat#95271-1G |
| Menadione | VWR International | Cat#ICNA0210225925 |
| Pantothenate | Sigma-Aldrich | Cat#P2250 |
| Advanced DMEM/F12 | Thermo Fisher Scientific | Cat#12634-010 |
| GlutaMAX | Thermo Fisher Scientific | Cat#35050-061 |
| HEPES | Thermo Fisher Scientific | Cat#15630-106 |
| B27 supplement | Thermo Fisher Scientific | Cat#17504-044 |
| N2 supplement | Thermo Fisher Scientific | Cat#17502-048 |
| Nicotinamide | Sigma-Aldrich | Cat#N0636 |
| N-acetyl-1-cysteine | Sigma-Aldrich | Cat#A5099 |
| [Leu15]-gastrin I, human | Sigma-Aldrich | Cat#G9145 |
| Recombinant murine epidermal growth factor | Peprotech | Cat#315-09 |
| Recombinant murine Noggin | Peprotech | Cat#250-38 |
| Recombinant murine R-Spondin-1 | Peprotech | Cat#315-32 |
| Recombinant Murine Wnt-3a | Peprotech | Cat#315-20 |
| Activin-like kinase (ALK) inhibitor (A83-01) | Tocris | Cat#2939 |
| p38 Mitogen-activated kinase (MAPK) inhibitor (SB202190) | Sigma-Aldrich | Cat#S7067 |
| Rho-associated protein kinase (ROCK) inhibitor | Sigma-Aldrich | Cat#Y0503 |

TABLE 2-continued

Exemplary Reagents and resources.

| REAGENT OR RESOURCE | SOURCE | IDENTIFIER |
| --- | --- | --- |
| Microvascular Endothelial Cell Growth Medium-2 BulletKit (EGM-2MV) | Lonza | Cat#CC3202 |
| Human epidermal growth factor | Lonza | Cat#CC3202 |
| Vascular endothelial growth factor | Lonza | Cat#CC3202 |
| Human fibroblastic growth factor-B | Lonza | Cat#CC3202 |
| R3-Insulin-like Growth Factor-1 | Lonza | Cat#CC3202 |
| Ascorbic Acid | Lonza | Cat#CC3202 |
| Primocin | InvivoGen | Cat#ant-pm-1 |
| Bacto Tryptone | BD Biosciences | Cat#211699 |
| Bacto Yeast Extract | BD Biosciences | Cat#212720 |
| Sodium chloride | HAWKINS PC | Cat#10142-840 |
| RPMI Medium 1640 | Life Technologies | Cat#72400-120 |
| Grape seeds oligomeric proanthocyanidins (PAC) | Sigma-Aldrich | Cat#1298208 |
| Dimethyl sulfoxide (DMSO) | Sigma-Aldrich | Cat#D2650 |
| DiHome | Cayman Chemicals | Cat#10009832 |
| 2-Hydroxyhexanoic acid | MedChem Express | Cat#HY-75954 |
| 2-Methylbenzoic acid | MedChem Express | Cat#HY-41494 |
| 2-sec-Butyl-3-methoxypyrazin | MedChem Express | Cat#HY-W017140 |
| 3,4-Dimethylbenzoic acid | MedChem Express and Sigma-Aldrich | Cat#HY-W017434 and D149403 |
| 4-Dodecylbenzenesulfonic acid | MedChem Express | Cat#HY-23059 |
| 4-Methylbenzoic acid | MedChem Express and Sigma-Aldrich | Cat#HY-76547 and T36803 |
| Acetylarginine | MedChem Express | Cat#HY-W014130 |
| Glutamine | MedChem Express | Cat#HY-100587 |
| Glucosamine | MedChem Express | Cat#HY-N0733 |
| Deoxycholic acid | MedChem Express | Cat#HY-N0593 |
| DL-Arginine | MedChem Express | Cat#HY-N0454 |
| DL-Homoserine | MedChem Express | Cat#HY-W012870 |
| Docosahexaenoic acid ethyl ester | MedChem Express | Cat#HY-W011120 |
| Heptanoic acid | MedChem Express and Sigma-Aldrich | Cat#HY-42935 and 75190 |
| Hexanoic acid | MedChem Express and Sigma-Aldrich | Cat#HY-N4078 and 153745 |
| Isoleucine | MedChem Express | Cat#HY-N0771 |
| Kanosamine | MedChem Express | Cat#HY-112176 |
| L-Lysine | MedChem Express | Cat#HY-N0469 |
| L-Tyrosine methyl ester | MedChem Express | Cat#HY-W007671 |
| Methyl-L-histidinate | MedChem Express | Cat#HY-W017006 |
| N-Acetyl-L-methionine | MedChem Express | Cat#HY-W012499 |
| N-Acetyl-L-phenylalanine | MedChem Express | Cat#HY-Y0068 |
| N-Acetylhistamine | MedChem Express | Cat#HY-112175 |
| Pimelic acid | MedChem Express | Cat#HY-Y1139 |
| Prolylleucine | MedChem Express | Cat#HY-112173 |
| Pyridoxine | MedChem Express | Cat#HY-N0682 |
| Silibinin | MedChem Express | Cat#HY-13748 |
| UDP-N-acetylglucosamine | MedChem Express | Cat#HY-112174 |
| Uracil | MedChem Express | Cat#HY-I0960 |
| 4% Paraformaldehyde Phosphate Buffer Solution | Wako Pure Chemical Corporation | Cat#16120141 |
| Dulbecco's phosphate-buffered saline, calcium, magnesium | Thermo Fisher Scientific | Cat#14040182 |
| Dulbecco's phosphate-buffered saline, no calcium, no magnesium | Thermo Fisher Scientific | Cat#14190144 |
| Chloroform | Sigma-Aldrich | Cat#288306 |
| Methanol | Sigma-Aldrich | Cat#1060351000 |
| Trypsin-EDTA (0.25%) | Thermo Fisher Scientific | Cat#25200056 |
| Collagenase, Type IV | Thermo Fisher Scientific | Cat#17104019 |
| Alexa Fluo 647 Phalloidin | Thermo Fisher Scientific | Cat#A22287 |
| 4',6-Diamidino-2-Phenylindole, Dihydrochloride (DAPI) | Thermo Fisher Scientific | Cat#D1306 |
| Anti-green fluorescent protein Alexa Fluor 488 conjugate | Thermo Fisher Scientific | Cat#A21311 |
| Type I collagen | Corning | Cat#354236 |
| TrypLE Express | Life Technologies | Cat#12605-010 |
| Cell recovery solution | BD | Cat#354253 |
| Collagenase I | Thermo Fisher Scientific | Cat#17100-017 |
| FBS | Gibco | Cat#10082-147 |
| Matrigel matrix growth factor reduced | Corning | Cat#356231 |
| ER-1 activation solution | Emulate Inc. | Cat#ER-1 |
| ER-2 activation solution | Emulate Inc. | Cat#ER-2 |

TABLE 2-continued

Exemplary Reagents and resources.

| REAGENT OR RESOURCE | SOURCE | IDENTIFIER |
|---|---|---|
| Critical commercial assays | | |
| MSD U-plex Assay | Meso Scale Diagnostoc | https://www.mesoscale.com |
| Rneasy Mini Kit | Qiagen | Cat#74104 |
| PowerUp SYBR Green Master Mix | Thermo Fisher Scientific | Cat#A25742 |
| SuperScript IV VILO Master Mix | Thermo Fisher Scientific | Cat#11756500 |
| Shiga Toxin 1 ELISA | Abraxis | Cat#542000 |
| Deposited data | | |
| RNA-seq data | Sequence Read Archive (accession: PRJNA497914]) | |
| Oligonucleotides | | |
| Primer: fliC 1259 Forward | (Morgan et al., 2014) | |
| Primer for fliC 1355 Reverse | (Morgan et al., 2014) | |
| Primer for rpoA Forward | (Yin et al., 2011) | |
| Primer for rpoA Reverse | (Yin et al., 2011) | |
| Primer for arcA Forward | (Jandu et al., 2009) | |
| Primer for arcA Reverse | (Jandu et al., 2009) | |
| Primer for Keio Flic knockout Forward | This study | |
| Primer for Keio Flic knockout Reverse | This study | |
| Recombinant DNA | | |
| pGEN-GFP(LVA) CbR plasmid | (Wiles et al., 2009) | |
| F primer FliC 2 | | |
| R promer FliC 2 | | |
| fli C-lux | s28 flagellin gene promoter fusion (AmpR) | Mobley Lab |
| Software and algorithms | | |
| Fiji | (Schindelin et al., 2012) | https://fiji.sc/ |
| StackReg plugin | (Thevenaz et al., 1998) | https://imagej.net/Stack Reg |
| TrackMate plugin | (Tinevez et al., 2017) | https://imagej.net/Track Mate |
| R language and environment for statistical computing | | https://www.r-project.org/ |
| Linear Models for Microarray Data (limma) package | (Ritchie et al., 2015) | 10.18129/B9.bioc.limma |
| R metabolomics package | (Bowne JB, 2014) | https://cran.r-project.org/web/packages/metabolomics/index.html |
| DEseq package | (Love et al., 2014) | 10.18129/B 9.bioc .DESeq |
| ClusterProfiler | (Yu et al., 2012) | 10.18129/B9.bioc.clusterProfiler |
| IMARIS | Bitplane | |

Each of these embodiments and obvious variations thereof is contemplated as falling within the spirit and scope of the claimed invention, which is set forth in the following claims. Moreover, the present concepts expressly include any and all combinations and sub-combinations of the preceding elements and aspects.

What is claimed is:

1. A method for establishing a stable complex community of gut commensal microbes in vitro, the method comprising:
providing cultured cells of an intestinal epithelium and microbiota from a mammalian fecal sample in an environment having a first level of oxygen, the microbiota being in direct and indirect contact with the intestinal epithelium, said fecal sample comprising a diluted fecal slurry and comprising both anaerobic bacteria and aerobic bacteria;
providing cultured cells of a vascular endothelium in an environment having a second level of oxygen, the second level of oxygen having a greater oxygen concentration than the first level of oxygen; and
facilitating the flux of oxygen between the first level of oxygen and the second level of oxygen to form a physiologically-relevant oxygen gradient.

2. The method of claim 1, further comprising providing oxygenation of the cultured cells of the intestinal epithelium and the cultured cells of the vascular endothelium while simultaneously providing an anaerobic environment for growth of obligate anaerobes.

3. The method of claim 1, further comprising achieving an oxygen concentration of less than approximately 0.5-2.0% in the first level of oxygen.

4. The method of claim 1, wherein the fecal sample was not passed through another mammal.

5. The method of claim 1, wherein the fecal sample was not cultured in vitro.

6. The method of claim 1, wherein the cultured microbiota comprises organisms from both the Firmicutes phyla and the Bacteroidetes phyla.

7. The method of claim 1, wherein the cultured microbiota comprises species selected from the group consisting of *Akkermansia, Oscillospira, Blautia* and *Suterella* species.

8. The method of claim 1, wherein the cultured microbiota comprises *Coprococcus, Anaerobacillus, Bifidobacterium*, and *Peptoniphilus* species.

9. The method of claim 1, wherein the cultured microbiome comprises at least 8 different genera of bacteria found in human feces.

10. The method of claim 1, wherein the cultured microbiome comprises at least 11 different genera of bacteria found in human feces.

11. The method of claim 10, wherein said fecal sample is from a human, and said cultured microbiome comprises said obligate anaerobes that contain ratios of organisms from both the Firmicutes phyla and the Bacteroidetes phyla similar to ratios in human feces.

\* \* \* \* \*